US008299046B2

(12) United States Patent
Sporn et al.

(10) Patent No.: US 8,299,046 B2
(45) Date of Patent: Oct. 30, 2012

(54) SYNTHETIC TRITERPENOIDS AND TRICYCLIC-BIS-ENONES FOR USE IN STIMULATING BONE AND CARTILAGE GROWTH

(75) Inventors: Michael B. Sporn, Tunbridge, VT (US); Karen T. Liby, West Lebanon, NH (US); Tadashi Honda, Hanover, NH (US); Gregory Mundy, San Antonio, TX (US); Ross Garrett, Austin, TX (US); Hari Reddi, El Macero, CA (US); Gordon W. Gribble, Lebanon, NH (US); Takahiro Niikura, Kobe (JP)

(73) Assignees: Trustees of Dartmouth College, Hanover, NH (US); Osteoscreen, Inc., San Antonio, TX (US); The Regents of the Universtiy of California, Oakland, CA (US)

( * ) Notice: Subject to any disclaimer, the term of this patent is extended or adjusted under 35 U.S.C. 154(b) by 209 days.

(21) Appl. No.: 11/941,723

(22) Filed: Nov. 16, 2007

(65) Prior Publication Data

US 2008/0233195 A1 Sep. 25, 2008

Related U.S. Application Data

(60) Provisional application No. 60/866,344, filed on Nov. 17, 2006.

(51) Int. Cl.
  *C07D 233/02* (2006.01)
(52) U.S. Cl. ........................................ 514/63; 548/300.1
(58) Field of Classification Search .................... 514/63; 548/300.1
  See application file for complete search history.

(56) References Cited

U.S. PATENT DOCUMENTS

| 4,395,423 | A | 7/1983 | Neumann | 424/304 |
|---|---|---|---|---|
| 4,808,614 | A | 2/1989 | Hertel | 514/45 |
| 5,013,649 | A | 5/1991 | Wang et al. | 435/69.1 |
| 5,064,823 | A | 11/1991 | Lee et al. | 514/198 |
| 5,401,838 | A | 3/1995 | Chou | 536/281 |
| 5,426,183 | A | 6/1995 | Kjell | 536/285.5 |
| 5,464,826 | A | 11/1995 | Grindey et al. | 514/50 |
| 5,521,294 | A | 5/1996 | Wildfeuer | 536/187 |
| 5,597,124 | A | 1/1997 | Kessel et al. | 241/30 |
| 5,603,958 | A | 2/1997 | Morein et al. | 424/489 |
| 5,606,048 | A | 2/1997 | Chou et al. | 536/271.1 |
| 5,972,703 | A | 10/1999 | Long et al. | 435/372 |
| 6,025,395 | A | 2/2000 | Breitner et al. | 514/570 |
| 6,303,569 | B1 | 10/2001 | Greenwald et al. | 514/2 |
| 6,326,507 | B1 | 12/2001 | Gribble et al. | 558/415 |
| 6,485,756 | B1 | 11/2002 | Aust et al. | 424/725 |
| 6,552,075 | B2 | 4/2003 | Gribble et al. | 514/522 |
| 6,974,801 | B2 | 12/2005 | Honda et al. | 514/25 |
| 7,176,237 | B2 | 2/2007 | Honda et al. | 514/519 |
| 7,265,096 | B2 | 9/2007 | Gallop et al. | 514/49 |
| 7,288,568 | B2 | 10/2007 | Gribble et al. | 514/519 |
| 7,435,755 | B2 | 10/2008 | Konopleva et al. | 514/510 |
| 2003/0119732 | A1* | 6/2003 | Konopleva et al. | 514/12 |
| 2005/0276836 | A1 | 12/2005 | Wilson et al. | 424/434 |
| 2005/0288363 | A1 | 12/2005 | Gribble et al. | 558/303 |
| 2007/0155742 | A1 | 7/2007 | Honda et al. | 514/519 |
| 2008/0220057 | A1 | 9/2008 | Gribble et al. | 514/522 |
| 2008/0261985 | A1 | 10/2008 | Honda et al. | 548/400 |
| 2009/0048205 | A1 | 2/2009 | Meyer et al. | 514/49 |
| 2009/0060873 | A1 | 3/2009 | Sporn et al. | 424/85.6 |
| 2009/0093447 | A1 | 4/2009 | Konopleva et al. | 514/510 |

FOREIGN PATENT DOCUMENTS

| DE | 10 2005 041613 | 3/2007 |
|---|---|---|
| EP | 0 272 891 A2 | 6/1988 |
| EP | 0 329 348 B1 | 7/1995 |
| EP | 0 376 518 B1 | 11/1995 |
| EP | 0 576 230 B1 | 4/1996 |
| EP | 0 577 303 B1 | 10/1997 |
| EP | 0 712 860 B1 | 12/2001 |
| WO | WO 91/15498 | 10/1791 |
| WO | WO 96/05290 | 2/1996 |
| WO | WO 98/00173 | 1/1998 |
| WO | WO 98/32762 | 7/1998 |
| WO | WO 99/33483 | 7/1999 |
| WO | WO 99/65478 | 12/1999 |
| WO | WO 00/73253 | 12/2000 |
| WO | WO 01/01135 | 1/2001 |
| WO | WO 01/28579 | 4/2001 |
| WO | WO 02/03996 | 1/2002 |
| WO | WO 02/47611 | 6/2002 |
| WO | WO 03/043631 | 5/2003 |
| WO | WO 03/059339 | 7/2003 |
| WO | WO 2005/042002 | 5/2005 |
| WO | WO 2005/046732 | 5/2005 |
| WO | WO 2006/029221 | 3/2006 |
| WO | WO 2007/005879 | 1/2007 |
| WO | WO 2007/069895 | 6/2007 |
| WO | WO 2008/111497 | 9/2008 |
| WO | WO 2008/136838 | 11/2008 |
| WO | WO 2009/023232 | 2/2009 |

OTHER PUBLICATIONS

Leach et. al. (Expert Opinion on Biological Therapy (2004) 4:1015-1027).*
Sun (Expert Opinion on Therapeutic Targets (2008) 12:239-251).*
Yan et. al. (Molecular Cancer (2006) 5:1452-1458).*
Honda et. al. (Bioorganic and Medicinal Chemistry letters (2002) 12:1027-1030).*
"CDDO in treating patients with metastatic or unresectable solid tumors or lymphoma," http://www.clinicaltrials.gov/ct2/show/NCT00352040?term=CDDO&rank=1, Dec. 14, 2008.
"FDA mulls drug to slow late-stage Alzheimer's," http://www.cnn.com/2003/HEALTH/conditions/09/24/alzheimers.drug.ap/index.html, Retrieved on Sep. 23, 2003.
"Phase IIa trail to determine the effects of bardoxolone methyl on renal function in patients with diabetic nephropathy," http://www.clinicaltrials.gov/ct2/show/NCT00664027?term=rta&rank=10, Dec. 14, 2008.

(Continued)

Primary Examiner — Marcos Sznaidman

(57) ABSTRACT

The present invention concerns methods for stimulating the growth and repair of bone and cartilage using synthetic triterpenoids and tricyclic-bis-enones. Examples of suitable triterpenoids include CDDO, CDDO-Me, CDDO-Im, and CDDO-Ethylamide. Examples of tricyclic-bis-enones include TBE-31 and TBE-34.

36 Claims, 12 Drawing Sheets

OTHER PUBLICATIONS

"RTA 402 in advanced solid tumors or lymphoid malignancies," http://www.clinicaltrials.gov/ct2/show/NCT00508807?term=rta&rank=2&show_desc=Y, Dec. 14, 2008.

"Study to assess the safety, tolerability, and Pharmacodynamics of RTA 402 in patients with hepatic dysfunction," http://www.clinicaltrials.gov/ct2/show/NCT00550849?term=rta&rank=4, Dec. 14, 2008.

Akrivakis et al., "Prolonged infusion of gemcitabine in stage IV breast cancer: a phase I study," *Anti-Cancer Drugs*, 10 (6): 525-531, 1999.

Alexander et al., "Synthesis and cytotoxic activity of two novel 1-dodecylthio-2-decyloxypropyl-3-phosphatidic acid conjugates with gemcitabine and cytosine arabinoside," *J. Med. Chem.*, 46 (19): 4205-4208, 2003.

Ardestani et al., "Effects of dexamethasone and betamethasone as COX-2 gene expression inhibitors on rigidity in a rat model of Parkinson's disease," *Indian J. Pharmacol.*, 39:235-9, 2007.

Ariga et al., "Role of sphingolipid-mediated cell death in neurodegenerative diseases," *Journal of Lipid Research*, 39:1-16, 1998.

Baker et al., "2'-Deoxy-2'-methylenecytidine and 2'-deoxy-2',2'-difluorocytidine 5'-diphosphates: potent mechanism-based inhibitors of ribonucleotide reductase," *J. Med. Chem.*, 34 (6): 1884, 1991.

Balkwill et al., "Smoldering and polarized inflammation in the initiation and promotion of malignant disease," *Cancer Cell*, 7 (3): 211-217, 2005.

Cerwenka and Swain, "TGF-β1: immunosuppressant and viability factor for T lymphocytes," *Microbes and Infection*, 1: 1291-1296, 1999.

Cho et al., "The transcription factor NRF2 protects against pulmonary fibrosis," *FASEB Journal*, 18:1-29, 2004.

Chou et al., "Sterospecific Synthesis of 2-Deoxy-2,2-difluororibonolactone and its Use in the Preparation of 2'-Deoxy-2', 2'-difluoro-B-D-ribofuranosyl Pyrimidine Nucleosides: The Key Role of Selective Crystallization," *Synthesis*, 565-570, 1992.

Cianchi et al., "Cyclooxygenase-2 activation mediates the proangiogenic effect of nitric oxide in colorectal cancer," *Clinical Cancer Research*, 10:2694-2704, 2004.

Cripe, "Adult Acute Leukemia," *Current Problems in Cancer*, 21 (1): 4-64, 1997.

Cui, "A material science perspective of pharmaceutical solids," *Int. J. Pharmceutics*, 339 (1-2): 3-18, 2007.

Di Stefano et al., "Inhibition of [3H]thymidine incorporation into DNA of rat regenerating liver by 2',2'-difluorodeoxycytidine coupled to lactosaminated poly-L-lysine," *Biochem. Pharmacol.*, 57 (7): 793-799, 1999.

Ekmekcioglu et al., "Tumor iNOS predicts poor survival for stage III melanoma patients," *Int. J. Cancer*, 119:861-866, 2006.

Ellies et al., "Mammary tumor latency is increased in mice lacking the inducible nitric oxide synthase," *Int. J. Cancer*, 106:1-7, 2003.

Gandhi et al., "Prolonged infusion of gemcitabine: clinical and pharmacodynamic studies during a phase I trial in relapsed acute myelogenous leukemia," *J. Clin. Oncol.*, 20 (3): 665-673, 2002.

Godoy et al., "Central and systemic IL-I exacerbates neurodegeneration and motor symptoms in a model of Parkinson's disease," *Brain*, 131:1880-1894, 2008.

Guo et al., "Selective Protection of 2',2'-Diflurodeoxycytidine (Gemcitabine),"*J. Org. Chem.*, 64: 8319-8322, 1999.

Guo et al., "Targeted delivery of a peripheral benzodiazepine receptor ligand-gemcitabine conjugate to brain tumors in a xenograft model," *Cancer Chemother. Pharmacol.*, 48 (2): 169-176, 2001.

Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.

Hong et al., "Phase I trial of a novel oral NF-κB/pSTAT3 inhibitor RTA-402 in patients with solid tumors and lymphoid malignancies," 44th Annual Meeting of the American Society of Clinical Oncology, 2008.

Kasinski et al., "Inhibition of IkappaB kinase-nuclear factor-kappaB signaling pathway by 3,5-bis(2-flurobenzylidene)piperidin-4-one (EF24), a novel monoketone analog of curcumin," *Mol. Pharmacology*, 74 (3): 654-661, 2008.

Klotz et al., "Selective expression of inducible nitric oxide synthase in human prostate carcinoma," *Cancer*, 82:1897-1903, 1998.

Lala et al., "Role of nitric oxide in tumor progression: lessons from experimental tumors," *Cancer and Metastasis Reviews*, 17 (1): 91-106, 1998.

Leonard et al., "Expression of nitric oxide synthase in inflammatory bowel disease is not affected by corticosteroid treatment," *J. Clin. Pathol.*, 51:750-753, 1998.

Li and Nel, "Role of the Nrf2-mediated signaling pathway as a negative regulator of inflammation: implications for the impact of particulate pollutants on asthma," *Antioxidants & Redox Signaling*, 8:88-98, 2006.

Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.

Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.

Luo et al., "IKK/NF-kappaB signaling: balancing life and death—a new approach to cancer therapy," *J. Clin. Invest.*, 115 (10): 2625-2631, 2005.

Mantovani et al., "Inflammation by remote control," *Nature*, 435:752-753, 2005.

Marrogi et al., "Nitric oxide synthase, cyclooxygenase 2, and vascular endothelial growth factor in the angiogenesis of non-small cell lung carcinoma," *Clinical Cancer Research*, 6:4739-4744, 2000.

Maurel et al., "Phase I trial of weekly gemcitabine at 3-h infusion in refractory, heavily pretreated advanced solid tumors," *Anti-Cancer Drugs*, 12 (9): 713-717, 2001.

Morse and Choi, "Heme oxygenase-1: the 'emerging molecule' has arrived," *Am. J. Respir. Crit. Care Med.*, 27(1):8-16, 2002.

Morse and Choi, "Herne oxygenase-1: the 'emerging molecule' has arrived," *Am. J. Respir. Crit. Care Med.*, 27(1):8-16, 2002.

Na and Surh et al., "Transcriptional regulation via cysteine thiol modification: a novel molecular strategy for chemoprevention and cytoprotection," *Mol. Carcinog.*,45 (6): 368-380, 2006.

Nathan et al., "Protection from Alzheimer's-like disease in the mouse by genetic ablation of inducible nitric oxide synthase," *The Journal of Experimental Medicine*, 202:1163-1169, 2005.

Nathan, "Points of control in inflammation," *Nature*, 420:846-852, 2002.

Office Action, in Canadian Patent App. No. 2,335,505, mailed Jan. 10, 2008.

Office Action, in Canadian Patent App. No. 2,335,505, mailed Nov. 23, 2006.

Office Action, in Canadian Patent App. No. 2,335,505, mailed Sep. 22, 2008.

Office Action, in Canadian Patent App. No. 2,430,454, mailed Jan. 20, 2009.

Office Action, in European Patent App. No. 01 989 130, mailed Jul. 31, 2008.

Office Action, in European Patent App. No. 03 729 681, mailed Nov. 6, 2008.

Office Action, in European Patent App. No. 99 928 731, mailed Aug. 1, 2008.

Office Action, in European Patent App. No. 99 928 731, mailed Dec. 9, 2008.

Office Action, in European Patent App. No. 99 928 731, mailed Dec. 15, 2004.

Office Action, in European Patent App. No. 99 928 731, mailed Feb. 14, 2007.

Office Action, in U.S. Appl. No. 09/335,003, mailed Aug. 28, 2000.
Office Action, in U.S. Appl. No. 09/335,003, mailed Mar. 15, 2001.
Office Action, in U.S. Appl. No. 09/335,003, mailed Nov. 2, 2000.
Office Action, in U.S. Appl. No. 09/927,081, mailed Feb. 22, 2002.
Office Action, in U.S. Appl. No. 09/998,009, mailed Apr. 4, 2007.
Office Action, in U.S. Appl. No. 09/998,009, mailed Jul. 11, 2005.
Office Action, in U.S. Appl. No. 09/998,009, mailed Jul. 14, 2004.

Office Action, in U.S. Appl. No. 09/998,009, mailed Jul. 3, 2006.
Office Action, in U.S. Appl. No. 09/998,009, mailed Mar. 24, 2004.
Office Action, in U.S. Appl. No. 09/998,009, mailed Nov. 30, 2005.
Office Action, in U.S. Appl. No. 09/998,009, mailed Nov. 16, 2007.
Office Action, in U.S. Appl. No. 09/998,009, mailed Oct. 20, 2004.
Office Action, in U.S. Appl. No. 10/345,053, mailed Aug. 25, 2004.
Office Action, in U.S. Appl. No. 10/345,053, mailed Dec. 23, 2004.
Office Action, in U.S. Appl. No. 10/345,053, mailed Dec. 6, 2005.
Office Action, in U.S. Appl. No. 10/345,053, mailed Mar. 1, 2006.
Office Action, in U.S. Appl. No. 10/345,053, mailed May 31, 2005.
Office Action, in U.S. Appl. No. 10/395,372, mailed Apr. 28, 2006.
Office Action, in U.S. Appl. No. 10/395,372, mailed Aug. 4, 2005.
Office Action, in U.S. Appl. No. 10/395,372, mailed Dec. 20, 2006.
Office Action, in U.S. Appl. No. 10/395,372, mailed Feb. 7, 2007.
Office Action, in U.S. Appl. No. 10/395,372, mailed Jan. 28, 2004.
Office Action, in U.S. Appl. No. 10/395,372, mailed Jul. 9, 2004.
Office Action, in U.S. Appl. No. 10/395,372, mailed Jun. 12, 2006.
Office Action, in U.S. Appl. No. 10/395,372, mailed May 23, 2005.
Office Action, in U.S. Appl. No. 10/395,372, mailed Nov. 23, 2005.
Office Action, in U.S. Appl. No. 10/435,925, mailed Sep. 30, 2005.
Office Action, in U.S. Appl. No. 11/121,316, mailed Apr. 16, 2009.
Office Action, in U.S. Appl. No. 11/121,316, mailed Jul. 21, 2008.
Office Action, in U.S. Appl. No. 11/121,316, mailed Mar. 17, 2008.
Office Action, in U.S. Appl. No. 11/672,449, mailed Jun. 13, 2008.
Office Action, in U.S. Appl. No. 11/672,449, mailed Mar. 20, 2009.
Office Action, in U.S. Appl. No. 11/927,418, mailed Mar. 2, 2009.
Office Action, in U.S. Appl. No. 11/941,820, mailed Apr. 21, 2009.
Osburn et al., "Genetic of pharmacologic amplification of Nrf2 signaling inhibits acute inflammatory liver injury in mice," *Toxicological Sciences*, 104:218-227, 2008.
Patel et al., "Phase II clinical investigation of gemcitabine in advanced soft tissue sarcomas and window evaluation of dose rate on gemcitabine triphosphate accumulation," *J. Clin. Oncol.*, 19 (15): 3483-3489, 2001.
PCT, International Preliminary Examination Report, in Int. App. No. PCT/US1999/13635, mailed Sep. 6, 2000.
PCT, International Preliminary Examination Report, in Int. App. No. PCT/US2001/44541, mailed Jan. 15, 2004.
PCT, International Preliminary Examination Report, in Int. App. No. PCT/US2003/01307, mailed Oct. 20, 2003.
PCT, International Search Report and Written Opinion, in Int. App. No. PCT/US2008/073352, mailed Feb. 13, 2009.
PCT, International Search Report and Written Opinion, in Int. App. No. PCT/US2007/085010, mailed Apr. 16, 2008.
PCT, International Search Report and Written Opinion, in Int. App. No. PCT/US2009/030771, mailed Apr. 9, 2009.
PCT, International Search Report and Written Opinion, in Int. App. No. PCT/US2007/071933, mailed Nov. 26, 2007.
PCT, International Search Report, in Int. App. No. PCT/US1999/13635, mailed Oct. 20, 1999.
PCT, International Search Report, in Int. App. No. PCT/US2001/44541, mailed Jan. 24, 2003.
PCT, International Search Report, in Int. App. No. PCT/US2003/01307, mailed May 12, 2003.
PCT, Written Opinion, in Int. App. No. PCT/US1999/13635, mailed May 15, 2000.
PCT, Written Opinion, in Int. App. No. PCT/US2001/44541, mailed Sep. 23, 2003.
Petition Decision, issued in U.S. Appl. No. 10/345,053, mailed May 22, 2006.
Pollard, "Tumour-educated macrophages promote tumour progression and metatasis," *Nature Reviews*, 4:71-78, 2004.
Rangasamy et al., "Disruption of Nrf2 enhances susceptibility to severe airway inflammation and asthma in mice," *Journal of Experimental Medicine*, 202:47-59, 2005.
Response to Office Action, in Canadian Patent App. No. 2,335,505, dated Jul. 10, 2008.
Response to Office Action, in Canadian Patent App. No. 2,335,505, dated May 11, 2007.
Response to Office Action, in European Patent App. No. 01 989 130, dated Sep. 5, 2008.
Response to Office Action, in European Patent App. No. 99 928 731, dated Oct. 1, 2008.
Response to Office Action, in European Patent App. No. 99 928 731, dated Mar. 9, 2009.
Response to Office Action, in European Patent App. No. 99 928 731, dated Jun. 23, 2005.
Response to Office Action, in European Patent App. No. 99 928 731, dated Aug. 14, 2007.
Response to Office Action, in U.S. Appl. No. 09/335,003, dated Sep. 28, 2000.
Response to Office Action, in U.S. Appl. No. 09/335,003, dated Mar. 2, 2001.
Response to Office Action, in U.S. Appl. No. 09/335,003, dated Apr. 16, 2001.
Response to Office Action, in U.S. Appl. No. 09/927,081, dated Jun. 24, 2002.
Response to Office Action, in U.S. Appl. No. 09/998,009, dated Apr. 21, 2004.
Response to Office Action, in U.S. Appl. No. 09/998,009, dated Sep. 14, 2004.
Response to Office Action, in U.S. Appl. No. 09/998,009, dated Apr. 19, 2005.
Response to Office Action, in U.S. Appl. No. 09/998,009, dated Oct. 11, 2005.
Response to Office Action, in U.S. Appl. No. 09/998,009, dated Mar. 30, 2006.
Response to Office Action, in U.S. Appl. No. 09/998,009, dated Jan. 3, 2007.
Response to Office Action, in U.S. Appl. No. 09/998,009, dated Sep. 4, 2007.
Response to Office Action, in U.S. Appl. No. 09/998,009, dated Feb. 18, 2008.
Response to Office Action, in U.S. Appl. No. 10/345,053, dated Sep. 24, 2004.
Response to Office Action, in U.S. Appl. No. 10/345,053, dated Mar. 23, 2005.
Response to Office Action, in U.S. Appl. No. 10/345,053, dated Sep. 3, 2005.
Response to Office Action, in U.S. Appl. No. 10/345,053, dated Feb. 6, 2006.
Response to Office Action, in U.S. Appl. No. 10/395,372, dated Apr. 28, 2004.
Response to Office Action, in U.S. Appl. No. 10/395,372, dated Nov. 9, 2004.
Response to Office Action, in U.S. Appl. No. 10/395,372, dated Jul. 25, 2005.
Response to Office Action, in U.S. Appl. No. 10/395,372, dated Nov. 23, 2005.
Response to Office Action, in U.S. Appl. No. 10/395,372, dated Apr. 21, 2006.
Response to Office Action, in U.S. Appl. No. 10/395,372, dated Oct. 12, 2006.
Response to Office Action, in U.S. Appl. No. 10/395,372, dated Jan. 12, 2007.
Response to Office Action, in U.S. Appl. No. 10/395,372, dated Feb. 14, 2007.
Response to Office Action, in U.S. Appl. No. 10/435,925, dated Mar. 30, 2005.
Response to Office Action, in U.S. Appl. No. 11/121,316, dated Apr. 4, 2008.
Response to Office Action, in U.S. Appl. No. 11/121,316, dated Dec. 19, 2008.
Response to Office Action, in U.S. Appl. No. 11/672,449, dated Dec. 15, 2008.
Response to Office Action, in U.S. Appl. No. 11/927,418, dated Apr. 2, 2009.
Response to Written Opinion, in Int. App. No. PCT/US1999/13635, dated Jul. 14, 2000.
Richardson et al., "Synthesis and restriction enzyme analysis of oligodeoxyribonucleotides containing the anti-cancer drug 2',2'-difluoro-2'-deoxycytidine," *Nucleic Acid Res.*, 20 (7): 1763-1769, 1992.
Rizzieri et al., "Phase I evaluation of prolonged-infusion gemcitabine with mitoxantrone for relapsed or refractory acute leukemia," *J. Clin. Oncol.*, 20 (3): 674-679, 2002.

Robbins et al., "Inflammation and Repair," In: Basic Pathology 3rd Edition, W.B. Saunders Company, Chapter 2, p. 28, 1981.

Singh and Evans, "Nitric oxide, the biological mediator of the decade: fact or fiction?" *Eur. Respir. J.*, 10:699-707, 1997.

Steadman's Medical Journal 23rd Edition, The Williams & Wilkins Company, p. 401, 1976.

Strejan et al., "Suppression of chronic-relapsing experimental allergic encephalomyelitis in strain-13 guinea pigs by administration of liposome-associated myelin basic protein," *J. Neuroimmunol.*, 7 (1): 27, 1984.

Suh et al., "New triterpenoids as cancer preventive and anti-inflammatory agents," *Proceedings of the American Association for Cancer Research*, Abstract No. 1457, 38: 216, 1997.

Supplementary European Search Report, issued in European Patent App. No. 01 989 130, mailed Aug. 9, 2007.

Supplementary European Search Report, issued in European Patent App. No. 03 729 681, mailed Aug. 3, 2006.

Sussan et al., "Disruption of Nrf2, a key inducer of antioxidant defenses, attenuates ApoE-mediated atherosclerosis in mice," *PLoS One*, 3 (11): 1-9, 2008.

Tempero et al., "Randomized phase II comparison of dose-intense gemcitabine: thirty-minute infusion and fixed dose rate infusion in patients with pancreatic adenocarcinoma," *J. Clin. Oncol.*, 21 (18): 3402-3408, 2003.

Therasse et al., "New guidelines to evaluate the response to treatment in solid tumors. European Organization for Research and Treatment of Cancer, National Cancer Institute of the United States, National Cancer Institute of Canada," *J. Natl. Cancer Instit.*, 92 (3): 205, 2000.

Thimmulappa et al., "Nrf2 is a critical regulator of the innate immune response and survival during experimental sepsis," *J. Clinical Investigation*, 116 (4): 984-995, 2006.

Thimmulappa et al., "Nrf2-dependent protection from LPS induced inflammatory response and mortality by CDDO-imidazolide," *Biochem. Biophys. Res. Commun.*, 351:883-889, 2006.

Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants & Redox Signaling*, 9:1-8, 2007.

Torres et al., "Inflammation and nitric oxide production in skeletal muscle of type 2 diabetic patients," *Journal of Endocrinology*, 181:419-427, 2004.

Tran et al., "The synthetic triterpenoid CDDO-methyl ester modulates microglial activities, inhibits TNF production, and provides dopaminergic neuroprotection," *Journal of Neuroinflammation*, 5:1-14, 2008.

U.S. Appl. No. 12/352,473, filed Jan. 12, 2009.
U.S. Appl. No. 12/426,737, filed Apr. 20, 2009.
U.S. Appl. No. 12/426,778, filed Apr. 20, 2009.
U.S. Appl. No. 12/426,791, filed Apr. 20, 2009.
U.S. Appl. No. 12/426,832, filed Apr. 20, 2009.
U.S. Appl. No. 12/426,889, filed Apr. 20, 2009.
U.S. Appl. No. 60/955,939, filed Aug. 15, 2007.

Van Muiswinkel and Kuiperij, "The Nrf2-ARE signaling pathway: promising drug target to combat oxidative stress in neurodegenerative disorders," *Current Drug Target—CNS & Neurological Disorders*, 4:267-281, 2005.

Veerman et al., "Antitumor activity of prolonged as compared with bolus administration of 2',2'-difluorodeoxycytidine in vivo against murine colon tumors," *Cancer Chemother. Pharmacol.*, 38 (4): 335-342, 1996.

Vodovotz et al., "Inducible nitric oxide synthase in tangle-bearing neurons of patients with Alzheimer's Disease," *The Journal of Experimental Medicine*, 184:1425-1433, 1996.

Yore et al., "The synthetic triterpenoid 1-[2-cyano-3,12-dioxooleana-1,9(11)-dien-28-oyl]imidazole blocks nuclear factor-kappaB activation through direct inhibition of IkappaB kinase beta," *Mol. Cancer Ther.*, 5 (12): 3232-3239, 2006.

Yu and Kensler, "Nrf2 as a target for cancer chemoprevention," *Mutat. Res.*, 591 (1-2): 93-102, 2005.

Zhou et al., "Physical stability of amorphous pharmaceuticals: Importance of configurational thermodynamic quantities and molecular mobility," *J. Pharmaceutical Sciences*, 91 (8): 1863-1872, 2002.

Abraham and Kappas, "Heme oxygenase and the cardiovascular-renal system," *Free Radic Biol Med.*, 39(1):1-25, 2005.

Agarwal and Mehta, "Possible involvement of Bcl-2 pathway in retinoid X receptor alpha-induced apoptosis of HL-60 cells," *Biochem Biophys Res Commun*, 230(2):251-253, 1997.

Ahmad et al., "Triterpenoid CDDO-Me blocks the NF-κB pathway by direct inhibition of IKKβ on Cys-179", *J. Biol. Chem.*, 281: 35764-9, 2006.

Al-alami et al., "Divergent effect of taxol on proliferation, apoptosis and nitric oxide production in MHH225 CD34 positive and U937 CD34 negative human leukemia cells," *Leukemia Res.*, 22:939-945, 1998.

Ambs et al., "p53 and vascular endothelial growth factor regulate tumor growth of NOS2-expressing human carcinoma cells," *Nat. Med.*, 4(12):1371-1376, 1998.

Amstutz et al., "Die position 5 im oxotremorin-gerust: eine zentrale stelle fur die steuerung der aktivitat am muscarinischen rezeptor," *Helv. Chim. Acta.*, 70:2232-2244, 1987.

Andreeff et al., "Expression of bcl-2-related genes in normal and AML progenitors: Changes induced by chemotherapy and cationic acid," *Leukemia*, 13:1881-1892, 1999.

Andreeff et al., "PPARgamma nuclear receptor as a novel molecular target in leukemias," *2002 Keystone Symposia*, Abstract No. 501, 2002.

Andreeff, "Acute myeloid leukemia," In: *Cancer Treatment*, Haskell (Ed.), W. B. Saunders, 911-922, 1995.

Araujo et al., "Systemic rather than local heme oxygenase-1 overexpression improves cardiac allograft outcomes in a new transgenic mouse,"*J Immunol.*, 171(3):1572-1580, 2003.

Bach, "Heme Oxygenase-1 and Transplantation Tolerance," *Hum Immunol.* 67(6):430-432, 2006.

Baeuerle, "NF-κB: ten years after," *Cell*, 87:13-20, 1996.

Bagasra et al., "Activation of the inducible form of nitric oxide synthase in the brains of patients with multiple sclerosis," *Proc. Natl. Acad. Sci. USA*, 92:12041-12045, 1995.

Baldwin, "The NF-κB and IκB proteins: new discoveries and insights," *Annu. Rev. Immunol.*, 14:649-681, 1996.

Bargou et al., "Constitutive nuclear factor κB-Re1A activation is required for proliferation and survival of Hodgkin's disease tumor cells," *J Clin. Invest.*, 100:2961-2969, 1997.

Barkett and Gilmore, "Control of apoptosis by Rel/NF-κB transcription factors," *Oncogene*, 18:6910-6924, 1999.

Barnes and Karin, "Nuclear factor-κB—a pivotal transcription factor in chronic inflammation diseases," *N. Engl. J. Med.*, 336:1066-1071, 1997.

Beal, "Mitochondria, free radicals, and neurodegeneration," *Curr. Opin. Neurobiol.*, 6:661-666, 1996.

Beran et al., "Topotecan and cytarabine is an active combination regimen in myelodysplastic syndromes and chronic myelomonocytic leukemia," *J. Clinical Oncology*, 17(9):2819-2830, 1999.

Bliard et al., "Glycosylation of acids under phase transfer conditions. Partial synthesis of saponins," *Tetrahedron Lett.*, 35:6107-6108, 1994.

Bogdan et al., "Contrasting mechanisms for suppression of macrophage cytokine release by transforming growth factor-beta and interleukin-10,"*J. Biol. Chem.*, 267:23301-23308, 1992.

Bogdan and Ding, "Taxol, a microtubule-stabilizing antineoplastic agent, induces expression of tumor necrosis factor α and interleukin-1 in macrophages," *J. Leukoc. Biol.*, 52(1):119-121, 1992.

Bollag and Holdener, "Retinoids in cancer prevention and therapy," *Annals of Oncology*, 3:513-526, 1992.

Boolbol et al., "Cyclooxygenase-2 overexpression and tumor formation are blocked by sulindac in a murine model of familial adenomatous polyposis," *Cancer Res.*, 56(11):2556-2560, 1996.

Bore et al., "The anti-inflammatory triterpenoid methyl 2-cyano-3, 12-dioxoolean 1,9(11)-dien-28-oate methanol solvate hydrate," Acta Crystallorg C., 58(Pt 3):o199-o200, 2002.

Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-1802, 2007.

Bruder and Caplan, "Terminal Differentiation of Osteogenic Cells in the Embryonic Chick Tibia is Revealed by a Monoclonal Antibody Against Osteocytes," *Bone*, 11:189-198, 1990.

Bruder and Caplan, "First bone formation and the dissection of an osteogenic lineage in the embryonic chick tibia is revealed by monoclonal antibodies against osteoblasts," *Bone*, 10:359-375, 1989.

Bruder et al., "Terminal Osteogenic Cell Differentiation in Culture Requires Beta-Glycerol Phosphate" *Trans. Ortho. Res. Soc.*, 16:58, 1991.

Bruland et al.,"Expression and characteristics of a novel human osteosarcoma-associated cell surface antigen," *Cancer Res.*, 48:5302-5308, 1988.

Buzoni-Gatel et al., "Intraepithelial lymphocytes traffic to the intestine and enhance resistance to Toxoplasma gondii oral infection," *J. Immunol.*, 162:5846-5852, 1999.

Buzoni-Gatel et al., "Murine ileitis after intracellular parasite infection is controlled by TGF-beta-producing intraepithelial lymphocytes," *Gastroenterolog*, 120:914-924, 2001.

Cai et al., "A new protecting group for alkynes: orthogonally protected dialkynes," *Helv. Chim. Acta.*, 78:732-757, 1995.

Carter et al., "Expression of survivin, a member of the inhibitor of apoptosis (IAP) family of caspase inhibitors is expressed in AML and regulated by cytokines and ATRA," *Blood*, 94(Suppl 1):479a, Abstract # 2142, 1999.

Cassady and Suffness, In *Anticancer Agents Based on Natural Product Models*; Academic Press, NY, 254-269, 1980.

Castaigne et al., "All-trans retinoic acid as a differentiation therapy for acute promyelocytic leukemia," *Blood*, 76(9):1704-1709, 1990.

Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.

Chen et al., "Chondrogenesis in chick limb bud mesodermal cells: reciprocal modulation by activin and inhibin," *Exp. Cell. Res.*, 206:119-27, 1993.

Chen et al., "Stimulation of chondrogenesis in limb bud mesoderm cells by recombinant human bone morphogenetic protein 2B (BMP-2B) and modulation by transforming growth factor beta 1 and beta 2," *Exp. Cell. Res.*, 195:509-15, 1991.

Cheng et al., "Differentiation of human bone marrow osteogenic stromal cells in vitro: induction of the osteoblast phenotype by dexamethasone," *Endocrinology*, 134:277-86, 1994.

Chintharlapalli et al., "2-Cyano-3,12-dioxoolean-1,9-dien-28-oic acid and related compounds inhibit growth of colon cancer cells through peroxisome proliferator-activated receptor gamma-dependent and -independent pathways," *Mol. Pharmacol.*, 68:119-128, 2005.

Chung and Wasicak, "Synthesis of chiral α-acetylenic cyclic amines from α-amino acids: applications to differentially constrained oxotremorine analogues as muscarinic agents," *Tetrahedron Lett.*, 31:3957-3960, 1990.

Clinton et al., "Steroidal[3,2-c]pyrazoles. II. Androstanes, 19-norandrostanes and their unsaturated analogs," *J. Am. Chem. Soc.*, 83:1478-1491, 1961.

Corey and Ruden, "Stereoselective methods for the synthesis of terminal *cis* AND *trans* enyne units," *Tetrahedron Lett.*, 1495-1499, 1973.

Coyle and Puttfarcken, "Oxidative stress, glutamate, and neurodegenerative disorders," *Science*, 262:689-695, 1993.

Dean et al., "Halogenolysis of methyl glycyrrhetate with lithium iodidedimethylformamide," *J Chem. Soc.*, 6655-6659, 1965.

Dezube et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 25(18S):14101, 2007.

Ding et al., "Macrophage deactivating factor and transforming growth factors-$\beta_1$, -$\beta_2$ and -$\beta_3$ inhibit induction of macrophage nitrogen oxide synthesis by IFN-$\kappa^1$,"*J Immunol.*, 145(3):940-944, 1990.

Dinkova-Kostova et al., „Extremely potent triterpenoid inducers of the phase 2 response: correlations of protection against oxidant and inflammatory stress, *Proc. Natl. Acad. Sci. USA*, 102(12):4584-4589, 2005.

Drach et al., "Induction of differentiation in myeloid leukemia cell lines and acute promyelocytic leukemia cells by liposomal all-trans-retinoic acid," *Cancer Research*, 53:2100-2104, 1993.

Dragnev et al., "The retinoids and cancer prevention mechanisms," *The Oncologist*, 5:361-368, 2000.

Drefahl and Huneck, "Nor-olea-12-enol-17-amin und Olea-12-enol-28-amin," *Chem. Ber.*, 91:278-281, 1958.

DuBois et al., "$G_1$ delay in cells overexpressing prostaglandin endoperoxide synthase-$2^1$," *Cancer Res.*, 56(4):733-737, 1996.

DuBois et al., "Increased cyclooxygenase-2 levels in carcinogen-induced rat colonic tumors," *Gastroenterology*, 110:1259-1262, 1996.

Dutcher et al., "Pentacyclic triterpene synthesis. 5. Synthesis of optically pure ring AB precursors," *J. Org. Chem.*, 41:2663-2669, 1976.

Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.

Elsawa et al., "Preferential Inhibition of Malignant Cell Growth by CDDO in Waldenstrom Macroglobulinemia," *Blood*, 108(11):2528, 2006.

Elstner et al., "Ligands for peroxisome proliferator-activated receptorgamma and retinoic acid receptor inhibit growth and induce apoptosis of human breast cancer cells in vitro and in BNX mice," *Proc. Natl. Acad. Sci. USA*, 95:8806-8811, 1998.

Embleton et al., "Antitumour reactions of monoclonal antibody against a human osteogenic-sarcoma cell line," *Br. J Cancer*, 43:4801-4805, 1981.

Engel et al., "Quantitation of minimal residual disease in acute myelogenous leukemia and myelodysplastic syndromes in complete remission by molecular cytogenetics of progenitor cells," *Leukemia*, 13:568-577, 1999.

Estey et al., "Molecular remissions induced by liposomal-encapsulated all-trans retinoic acid in newly diagnosed acute promyelocytic leukemia," *Blood*, 94:2230-2235, 1999.

Estey et al., "Randomized phase II study of fludarabine + cytosine arabinoside + idarubicin + all-trans retinoic acid + granulocyte-colony stimulating factor in poor prognosis newly diagnosed acute myeloid leukemia and myelodysplastic syndrom," *Blood*, 93(8):2478-2484, 1998.

Favaloro et al., "Design and synthesis of tricyclic compounds with enone functionalities in rings A and C: a novel class of highly active inhibitors of nitric oxide production in mouse macrophages," *J. Med. Chem.*, 45:4801-4805, 2002.

Finkbeiner and Stiles, "Chelation as a driving force in organic reactions. IV. Synthesis of a α-nitro acids by control of the carboxylation-decarboxylation equilibrum," *J. Am. Chem. Soc.*, 85:616-622, 1963.

Genain and Hauser, "Creation of a model for multiple sclerosis in Callithrix jacchus marmosets," *J. Mol. Med.*, 75:187-197, 1997.

Ghosh et al., "NF-κB and Rel proteins: evolutionarily conserved mediators of immune response," *Annu Rev Immunol.*, 16:225-260, 1998.

Grieco and Speake, "Synthetic Studies on Quassinoids: Total Synthesis and Biological Evaluation of (+)-Des-D-chaparrinone,"*J. Org. Chem.*, 63:5929-5936, 1998.

Gura et al., "Systems for identifying new drugs are often faulty," *Science*, 278:1041-1042, 1997.

Guttridge et al., "NF-kappaB controls cell growth and differentiation through transcriptional regulation of cyclin D1," *Mol. Cell. Biol.*, 19:5785-5799, 1999.

Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.

Heiner et al., "Localization of GD2-specific monoclonal antibody 3F8 in human osteosarcoma," *Cancer Res.*, 47:5377-5384, 1987.

Hidvegi et al., "A low temperature method of isolating normal human articular chondrocytes," *Osteoarthr. Cartil.*, 14:89-93, 2006.

Hinz et al., "NF-kappaB function in growth control: regulation of cyclin D1 expression and G0/G1-to-S-phase transition," *Mol. Cell Biol.*, 19:2690-2698, 1999.

Hirota et al., "Stereoselective total synthesis of (±)-eperuane-8β,15-diol[1]," *Bull. Chem. Soc. Jpn.*, 61:4023-4028, 1988.

Hirota et al., "Suppression of tumor promoter-induced inflammation of mouse ear by ursolic acid and 4,4-dimethycholestane derivatives" *Agric. Biol. Chem.*, 54:1073-1075, 1990.

Hirota et al., "Total synthesis of (±)-amarolide, a quassinoid bitter principle," *J. Org. Chem.*, 56:1119-1127, 1991.

Honda et al., "A novel dicyanotriterpenoid, 2-cyano-3,12-dioxooleanan-1,9(11)-dien-28-onitrile, active at picomolar concentrations for inhibition of nitric oxide production," *Bioorganic & Medicinal Chemistry Letters*, 12:1027-1030, 2002.

Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.

Honda et al., "Efficient synthesis of (−)- and (+)-tricyclic compounds with enome functionalities in rings A and C. A novel class of orally active anti-inflammatory and cancer chemopreventive agents," Org Biomol Chem, 1:4384-4391, 2003.

Honda et al., "New enone derivatives of oleanolic acid and ursolic acid as inhibitors of nitric oxide production in mouse macrophages," *Bioorg. Med. Chem. Lett.*, 7:1623-1628, 1997.

Honda et al., "Novel synthetic oleanane and ursane triterpenoids with various enone functionalities in ring A as inhibitors of nitric oxide production in mouse macrophages," *J. Med. Chem.*, 43:1866-1877, 2000.

Honda et al., "Novel synthetic oleanane triterpenoids: a series of highly active inhibitors of nitric oxide production in mouse macrophages," *Bioorg. Med. Chem. Lett.*, 9(24):3429-3434, 1999.

Honda et al., "Synthesis of (±)-3,3-ethylenedioxy-14α-hydroxy-5-picrasene-11,16-dione, a 14αH-picrasane derivative," *Chem. Lett.*, 299-302, 1981.

Honda et al., "Synthesis of a novel dicyano abietane analogue: a potential antiinflammatory agent," *J. Org. Chem.*, 71:3314-3316, 2006.

Honda et al., "Synthetic oleanane and ursane triterpenoids with modified rings A and C: a series of highly active inhibitors of nitric oxide production in mouse macrophages," *J. Med. Chem.*, 43:4233-4246, 2000.

Honda et al., "An Efficient Synthesis of Tricyclic Compounds, (±)-(4aβ,8aβ,10aα)-1,2,3,4,4a,6,7,8,8a,9,10,10a,- Dodecahydro-1,1,4a-Trimethy1-2-Oxophenanthrene-8a-Carboxylic Acid, its Methyl Ester, and (±)-(4aβ,8aβ,10aα)-3,4,4a,6,7,8,8a,9,10,10a-Decahydro-8a-Hydroxymethyl-1,1,4a-Trimethylphenanthren-2(1*H*)-One," *Org. Prep. Proced. Int.*, 37:546-550, 2005.

Hosoi et al., "Detection of human osteosarcoma-associated antigen(s) by monoclonal antibodies," *Cancer Res.*, 42:654-661, 1982.

Huang et al., "Inhibition of skin tumorigenesis by Rosemary and its constituents carnosol and ursolic acid," *Cancer Res.*, 54:701-708, 1994.

Huang et al., "Inhibitory effects of dietary curcumin on forestomach, duodenal, and colon carcinogenesis in mice," *Cancer. Res.*, 54:5841-5847, 1994.

Huang et al., "Structure of a WW domain containing fragment of dystrophin in complex with β-dystroglycan," *Nat. Struct. Biol.*, 7:634-638, 2000.

Hyer et al., "Synthetic triterpenoids cooperate with tumor necrosis factor-related apoptosis-inducing ligand to induce apoptosis of breast cancer cells," *Cancer Res.*, 65:4799-4808, 2005.

Iguchi et al., "Lipid peroxidation and disintegration of the cell membrane structure in cultures of rat lung fibroblasts treated with asbestos," *J. Appl. Toxicol.*, 13:269-275, 1993.

Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-45, 2004.

Ikeda et al., "The novel triterpenoid CDDO and its derivatives induce apoptosis by disruption of intracellular redox balance," *Cancer Res.*, 63:5551-5558, 2003.

Ishikawa et al., "Heme oxygenase-1 inhibits atherogenesis in Watanabe heritable hyperlipidemic rabbits," *Circulation*, 104(15):1831-1836, 2001.

Ito et al., "Involvement of caspase-8 in the induction of osteosarcoma cell apoptosis by the novel triterpenoid CDDO," *47th Annual Meeting, Orthopaedic Research Society*, Feb. 25-28, 2001, San Francisco, California, p. 0863, Poster Session, 2001.

Ito et al., "The novel triterpenoid 2-cyano-3, 12-dioxoolean-1,9-dien-28-oic acid induces apoptosis of human myeloid leukemia cells by a caspase-8-dependent mechanism," *Cell Growth & Differentiation*, 11(5):261-267, 2000.

Ito et al., "The novel triterpenoid CDDO induces apoptosis and differentiation of human osteosarcoma cells by a caspase-8 dependent mechanism," *Mol. Pharmacol.*, 59:1094-1099, 2001.

Johansen et al., "Pharmacology and preclinical pharmacokinetics of the triterpenoid CDDO methyl ester," *Proc. Amer. Assoc. Cancer Res.*, 44:1728, 2003.

Johnson et al., "A plan for distinguishing between some five- and six-membered ring ketones," *J. Am Chem. Soc.*, 67:1745-1754, 1945.

Johnson et al., "Relationships between drug activity in NCI preclinical in vitro and in vivo models and early clinical trials," *Br. J. Cancer*, 84:1424-1431, 2001.

Joyce et al., "Integration of Rac-dependent regulation of cyclin D1 transcription through a nuclear factor-kappaB-dependent pathway," *J. Biol. Chem.*, 274:25245-25249, 1999.

Kahne and Collum, "Kinetic cyanations of ketone enolates," *Tetrahedron Lett.*, 22:5011-5014, 1981.

Kaltschmidt et al., "Transcription factor NF-kappaB is activated in primary neurons by amyloid beta peptides and in neurons surrounding early plaques from patients with Alzheimer disease," *Proc. Natl. Acad. Sci. USA*, 94:2642-2647, 1997.

Kawamori et al., "Chemopreventive activity of celecoxib, as specific cyclooxygenase-2 inhibitor, against colon carcinogenesis," *Cancer Res.*, 58(3):409-412, 1998.

Kerwin et al., "Quassinoid synthesis. 2. Preparation of a tetracyclic intermediate having the Bruceantin tetrahydrofuran ring," *J. Org. Chem.*, 52:1686-1695, 1987.

Khan et al., "A dichotomous role for nitric oxide during acute Toxoplasma gondii infection in mice," *Proc. Natl. Acad. Sci. USA*, 94:13955-13960, 1997.

Kim et al., "Capasase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.

Kim et al., "Identification of a novel synthetic triterpenoid, methyl-2-cyano-3,12-dioxooleana-1,9-dien-28-oate, that potently induces caspace-mediated apoptosis in human lung cancer cells," Molecular Cancer Therapeutics, 1:177-184, 2002.

Kircher, "Triterpenes, in organ pipe cactus," *Phytochemistry*, 19:2707-2712, 1980; Database CAPLUS on STN AN:1981:550946.

Konopleva and Andreeff, "Regulatory pathways in programmed cell death," *Cancer Mol Biol.*, 6:1229-1260, 1999.

Konopleva et al., "Activation of nuclear transcription factor PPARgamma by the novel triterpenoid CDDO as targeted therapy in breast cancer," *2002 Keystone Symposium*, Abstract No. 539, 2002.

Konopleva et al., "Apoptosis: molecules and mechanisms," *Adv Exp Med Biol*, 457:217-236, 1998.

Konopleva et al., "Engraftment potential of AML progenitors into NOD/scid mice is dependent on baseline CXCR4 expression," *Blood*, 94(Suppl 1):166b, Abstract #3916, 1999.

Konopleva et al., "Mechanisms and Activity of PPARgamma-Active Triterpenoids CDDO and CDDO-Me in Leukemias," *Blood*, 106:2460, 2005.

Konopleva et al., "Novel synthetic triterpenoid CDDO-Me: potent antiproliferative, proapoptotic and differentiating agent in AML," *Blood*, 96(11), Part 1: 121A, abstract # 522, 2000.

Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.

Konopleva et al., "Novel triterpenoid CDDO-Me is a potent inducer of apoptosis and differentiation in acute myelogenous leukemia," *Blood*, 99(1):326-335, 2002.

Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.

Konopleva et al., "PPARγ nuclear receptor as a novel therapeutic target in AML," *Blood*, 96(11):460a, Abstract #1982, 2000.

Konopleva et al., "PPARgamma Ligand CDDO Induces Apoptosis in Leukemias Via Multiple Apoptosis Pathways," *Abstracts of the 44th Annual Meeting of the American Society of Hematology*, Abstract No. 2209, 2002.

Konopleva et al., "PPARgamma Ligands Are Potent Inducers of Apoptosis in Leukemias and Lymphomas," *American Society of Hematology 43rd Annual Meeting and Exposition*, Abstract No. 501, 2001.

Konopleva et al., "PPARgamma Nuclear Receptor as a Novel Molecular Target in Leukemia Therapy," *Proc. Amer. Assoc. Cancer Res.*, 43:4730, 2002.

Konopleva et al., "PPARgamma Nuclear Receptor as a Novel Therapeutic Target in AML," *Proc. Amer. Assoc. Cancer Res.*, 42:4458, 2001.

Konopleva et al., "Suppression of ERK Activation is Required for Triterpenoid Methyl-CDDO-Induced Apoptosis in AML," *Blood*, 102(11):1404, 2003.

Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.

Konopleva et al., "Synthetic triterpenoid CDDO as a novel therapy for resistant breast cancer," *Proc. Amer. Assoc. Cancer Res.*, 44:2726, 2003.

Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

Konopleva et al., "Triterpenoid Methyl-CDDO Is a Potent Inducer of Apoptosis in CD34+ AML Progenitor Cells Via Activation of SAPK Pathways and Inhibition of MAPK Cascades," *Blood*, 104:2533, 2004.

Kornblau et al., "Apoptosis regulating proteins as targets of therapy for hematological malignancies," *Exp. Opin. Inv. Drugs*, 8:2027-2057, 1999.

Kornblau et al., "Phase I study of mitoxantrone plus etoposide with multidrug blockage by SDZ PSC-833 in relapsed or refractory acute myelogenous leukemia," *J. Clin. Oncol.*, 15(5):1796-1802, 1997.

Kowalski and Reddy, "Ester homologation revisited: a reliable, higher yielding and better understood procedure," *J. Org. Chem.*, 57:7194-7208, 1992.

Kress et al., "Triterpenoids Display Single Agent Activity in a Mouse Model of CLL/SBL," *Blood*, 108(11):2530, 2006.

Kress et al., "Triterpenoids Display Single Agent Anti-tumor Activity in a Transgenic Mouse Model of Chronic Lymphocytic Leukemia and Small B Cell Lymphoma," *PLoS ONE*, 6(e559):1-11, 2007.

Kruger et al., "Up-regulation of heme oxygenase provides vascular protection in an animal model of diabetes through its antioxidant and antiapoptotic effects," *J Pharmacol Exp Ther.*, 319:1144-52, 2006.

Kurbacher et al., "Ascorbic acid (vitamin C) improves the antineoplastic activity of doxorubicin, cisplatin, and paclitaxel in human breast carcinoma cells in vitro," *Cancer Lett.*, 103:183-189, 1996.

Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.

Langille et al., "Differential effects of physiological concentrations of retinoic acid in vitro on chondrogenesis and myogenesis in chick craniofacial mesenchyme," *Differentiation*, 40:84, 1989.

Lapillonne et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.

Lawson et al., "Isolation and preliminary characterization of a monoclonal antibody that interacts preferentially with the liver isoenzyme of human alkaline phosphatase," *Clin. Chem.*, 31:381-385, 1985.

Lee et al., "Functional and quantitative analysis of splenic T cell immune responses following oral toxoplasma gondii infection in mice," *Experimental Parasitology*, 91:212-221, 1999.

Lemieux, "Acylglycosyl Halides. [55] tetra-O-acetyl-α-D-glucopyranosyl bromide," *Methods Carbohydr. Chem.*, 2:221-222, 1963.

Liby et al., "The synthetic triterpenoids, CDDO and CDDO-imidazolide, are potent inducers of heme oxygenase-1 and Nrf2/ARE signaling," *Cancer Res.*, 65:4789-4798, 2005.

Lieu et al., "Dual cytotoxic mechanisms of submicromolar taxol on human leukemia HL-60 cells," *Biochem. Pharmacology*, 53:1587-1596, 1997.

Ling et al., "The novel triterpenoid C-28 methyl ester of 2-cyano-3,12-dioxoolen-1, 9-dien-28-oic acid inhibits metastatic murine breast tumor growth through inactivation of STAT3 signaling," *Cancer Res.*, 67:4210-4218, 2007.

Ling et al., "The novel triterpenoid CDDO-Me inhibits metastatic murine breast tumor through inhibition of Stat3 signaling," 2007 AACR Annual Meeting, Abstract No. 301, 2007.

Liotta et al., "A simple method for the efficient sysnthesis of unsaturated β-dicarbonyl compunds," *J. Org. Chem.*, 46:2920-2923, 1981.

Liu et al., "Heme oxygenase-1 (HO-1) inhibits postmyocardial infarct remodeling and restores ventricular function," *FASEB J.*, 20(2):207-216, 2006.

Long, "Regulation of human bone marrow-derived osteoprogenitor cells by osteogenic growth factors," *Clin. Invest.*, 95:881-887, 1995.

MacMicking et al., "Altered responses to bacterial infection and endotoxic shock in mice lacking inducible nitric oxide synthase," *Cell*, 81:641-650, 1995.

Marnett, "Aspirin and the potential role of prostaglandins in colon cancer," *Cancer Res.*, 52(20):5575-5589, 1992.

McGeer and McGeer, "The inflammatory response system of brain: implications for therapy of Alzheimer and other neurodegenerative diseases," *Brain Res. Brain Res. Rev.*, 21:195-218, 1995.

Mehta et al., "Activation of retinoid receptors RAR alpha and RXR alpha induces differentiation and apoptosis, respectively, in HL-60 cells," *Cell, Growth Differ*, 7(2): 179-186, 1996.

Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-gamma expression," *Gynecologic Oncology*, 93:149-154, 2004.

Mella et al., "1, 2-dideoxy-3, 4:5, 7-bis-o-(1-methylethylidene)-D-gluco- and -D-galacto-hept-1-ynitols : synthesis and conformational studies," *Tetrahedron*, 44:1673-1678, 1988.

Merril and Benveniste, "Cytokines in inflammatory brain lesions: helpful and harmful," *Trends Neurosci.*, 19:331-338, 1996.

Minns et al., "A novel triterpenoid induces transforming growth factor beta production by intraepithelial lymphocytes to prevent ileitis," *Gastroenterology*, 127:119-126, 2004.

Mix et al., "A synthetic triterpenoid selectively inhibits the induction of matrix metalloproteinases 1 and 13 by inflammmatory cytokines," *Arthritis Rheum.*, 44:1096-1104, 2001.

Mix et al., "Peroxisome proliferator-activated receptor-gamma-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65:309-318, 2004.

Moncada et al., "Nitric oxide: physiology, pathophysiology, and pharmacology," *Pharmacol. Rev.*, 43:109-142, 1991.

Morse and Choi, "Heme oxygenase-1: from bench to bedside," *Am. J. Respir. Crit. Care Med.*, 172(6):660-670, 2005.

Murphy et al., "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.

Murray and Zweifel, "Perparation of Phenyl Cyanate and its Utilization for the Synthesis of α, β-Unsaturated Nitriles," *Synthesis*, 150-151, 1980.

Muzart, "Synthesis of unsaturated carbonyl compounds via a chromium-mediated allylic oxidation by 70% tert.butylhydroperoxide," *Tetrahedron Lett.*, 28:4665-4668, 1987.

Nathan and Xie, "Nitric oxide synthases: roles, tolls, and controls," *Cell*, 78:915-918, 1994.

Nicholson et al., "Lethality of endotoxin in mice genetically deficient in the respiratory burst oxidase, inducible nitric oxide synthase, or both, "*Shock*, 11:253-258, 1999.

Nishino et al., "Inhibition of the tumor-promoting action of 12-O tetradecanoylphorbol-13-acetate by some oleanane-type triterpenoid compounds," *Cancer Res.*, 48:5210-5215, 1988.

Ohshima and Bartsch, "Chronic infections and inflammatory process as cancer risk factors: possible role of nitric oxide in carcinogenesis," *Mutat. Res.*, 305:253-264, 1994.

Omura and Swern, "Oxidation of Alcohols by 'Activated' Dimethyl Sulfoxide. A Preparative Steric and Mechanistic Study," *Tetrahedron*, 34:1651-1660, 1978.

Ono et al., "A convenient procedure for esterification of carboxylic acids," *Bull. Chem. Soc. Jpn.*, 51:2401-2404, 1978.

Oshima et al., "Suppression of intestinal polyposis in Apc$^{\Delta 716}$ knockout mice by inhibition of cyclooxygenase 2 (COX-2)," *Cell*, 87:803-809, 1996.

Pahl, "Activators and target genes of Rel/NF-κB transcription factors," *Oncogene*, 18:6853-6866, 1999.

Palcy and Goltzman, "Protein kinase signalling pathways involved in the up-regulation of the rat alphaI (I) collagen gene by transforming growth factor beta1 and bone morphogenetic protein 2 in osteoblastic cells," *Biochem. J.*, 343:21-27, 1999.

Paul et al., "Design and synthesis of a self-assembled photochemical dyad based on selective imidazole recognition," *Inorg. Chem.*, 41:3699-3704, 2002.

Paul et al., "Effective expression of small interfering RNA in human cells," *Nature Biotechnol.*, 20:505-508, 2002.

Pedersen et al., "The triterpenoid CDDO induces apoptosis in refractory CLL B cells," *Blood*, 100:2965-2972, 2002.

Picard et al., "The triterpene resinols and related acids, part VI," *J. Chem. Soc.*, 1045-108, 1939.

Place et al., "The novel synthetic triterpenoid, CDDO-imidazolide, inhibits inflammatory response and tumor growth in vivo," *Clin. Cancer Res.*, 9:2798-2806, 2003.

Prescott and White, "Self-promotion? Intimate connections between APC and prostaglandin H synthase-2," *Cell*, 87:783-786, 1996.

Rayet and Gelinas, "Aberrant rel/nfkb genes and activity in human cancer," *Oncogene*, 18:6938-6947, 1999.

Reddy et al., "Evaluation of cyclooxygenase-2 inhibitor for potential chemopreventive properties in colon carcinogenesis," *Cancer Res.*, 56(20):4566-4569, 1996.

Rossi et al., "Anti-inflammatory cyclopentenone prostaglandins are direct inhibitors of IkappaB kinase," *Nature*, 403:103-108, 2000.

Ruvolo et al., "The novel triterpenoid methyl-CDDO inhibits Bcl2 phosphorylation and potently kolls U937 cells," *Blood*, 94(10), Suppl. 1, Part 1: 280A, abstract #1251, 1999.

Sacerdoti et al., "Heme Oxygenase Overexpression Attenuates Glucose-mediated Oxidative Stress in Quiescent Cell Phase: Linking Heme to Hyperglycemia Complications," *Curr Neurovasc Res.* 2(2):103-111, 2005.

Salvemini et al., "Endogenous nitric oxide enhances prostaglandin production in a model of renal inflammation," *J. Clin. Invest.*, 93(5):1940-1947, 1994.

Salvemini et al., "Nitric oxide activates cyclooxygenase enzymes," *Proc. Natl. Acad. Sci. USA*, 90(15):7240-7244, 1993.

Samudio et al., "2,cyano-3,12 dioxoolean-1,9 diene-28-imidazolide induces apoptosis in pancreatic cancer via redox-dependent cytoplasmic stress," *Proc. Amer. Assoc. Cancer Res.*, 46:5899, 2005.

Samudio et al., "2-Cyano-3,12-dioxooleana-1,9-dien-28-imidazolide (CDDO-Im) directly targets mitochondrial glutathione to induce apoptosis in pancreatic cancer," *J. Biol. Chem.*, 280:36273-36282, 2005.

Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.

Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," *Proc. Am. Assoc. Cancer Res.*, 47: 4693, 2006.

Samudio et al., "A Novel Mechanism of Action of Methyl-2-cyano-3,12 dioxoolean-1,9 diene-28-oate (CDDO-Me): Direct Permeabilization of the Inner Mitochondrial Membrane to Inhibit Electron Transport and Induce Apoptosis," *Blood*, 106:4462, 2005.

Samudio et al., "The novel triterpenoid CDDOme potently synergizes with inhibition of bcl-2 function to induce apoptosis in AML via disruption of intracellular redox homeostasis," *Proc. Amer. Assoc. Cancer Res.*, 46:4955, 2005.

Satoh et al., "Activation of the Keap1/Nrf2 pathway for neuroprotection by electrophilic [correction of electrophillic] phase II inducers," *Proc Natl Acad Sci USA*, 103(3):768-773, 2006.

Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4:6321, 2003.

Seibert and Masferrer, "Role of inducible cyclooxygenase (COX-2) in inflammation," *Receptor*, 4(1):17-23, 1994.

Sharpless et al., "Electrophilic and nucleophilic organoselenium reagents. New routes to alpha, beta-unsaturated carbonyl compounds," *J. Am. Chem. Soc.*, 95:6137, 1973.

Sheng et al., "A selective cyclooxygenase 2 inhibitor suppresses the growth of H-ras-transformed rat intestinal epithelial cells," *Gastroenterology*, 113(6):1883-18891, 1997.

Sheng et al., "Inhibition of human colon cancer cell growth by selective inhibition of cyclooxygenase-2," *J. Clin. Invest.*, 99(9):2254-2259, 1997.

Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," *Clin. Cancer Res.*, 12:1828-1838, 2006.

Shull et al., "Identification of a vitamin D-responsive protein on the surface of human osteosarcoma cells," *Proc. Natl. Acad. Sci. USA*, 86:5405-5410, 1989.

Shull et al., "Morphologic and biochemical studies of canine mucopolysaccharidosis I," *Am. J. Pathol.*, 114:487-495, 1984.

Simonian and Coyle, "Oxidative stress in neurodegenerative diseases," *Annu. Rev. Pharmacol. Toxicol.*, 36:83-106, 1996.

Simonsen et al., "Tetracyclic hydroxy acids," In *the Terpenes*, Cambridge University, Cambridge, 5:221-285, 1957.

Singh et al., "Anti-inflammatory activity of oleanolic acid in rats and mice," *J. Pharm.Pharmacol.*, 44:456-458, 1992.

Sive et al., "Expression of chondrocyte markers by cells of normal and degenerate intervertebral discs," *Mol. Pathol.*, 55:91-97, 2002.

Snitman et al., "Synthetic approaches to taxodione synthesis of methyl 12-oxopodocarpa-5,9(11)-diene-8β-carboxylate," *Synth. Comm.*, 8:187-194, 1978.

Sonogashira et al., "A convenient synthesis of acetylenes: catalytic substitutions of acetylenic hydrogen with bromoakenes, iodoarenes, and bromopyridines," *Tetrahedron Lett.*, 4467-4470, 1975.

Sporn and Roberts, "Peptide growth factors and inflammation, tissue repair, and cancer," *J. Clin. Invest.*, 78:329-332, 1986.

Sporn et al., "Prospects for prevention and treatment of cancer with selective PPARγ modulators (SPARMs)," *Trends in Molecular Medicine*, 7(9):395-400, 2001.

Sporn et al., "Transforming growth factor-beta: biological function and chemical structure," *Science*, 233:532-534, 1986.

Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 277:16448-16455, 2002.

Sterzycki, "Pyridinium tosylate, a mild catalyst for formation and cleavage of dioxolane-type acetals," *Synthesis*, 724-725, 1979.

Stewart et al., "Risk of Alzheimer's disease and duration of NSAID use" *Neurology*, 48:626-632, 1997.

Suh et al., "A novel synthetic oleanane triterpenoid, 2-cyano-3,12-dioxoolean-1,9-dien-28-oic acid (CDDO), induces cell differentiation in human myeloid leukemias," *Proceedings of the American Association for Cancer Research Annual Meeting*, 40:300, abstract # 1988, 1999.
Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.
Suh et al., "Novel triterpenoids suppress inducible nitric oxide synthase (iNOS) and inducible cyclooxygenase (COX-2) in mouse macrophages," *Cancer Res.*, 58:717-723, 1998.
Suh et al., "Novel triterpenoids suppress inducible ntiric oxide synthase (iNOS) and inducible cyclooxygenase (COX-2)," *Proceedings of the American Association for Cancer Research Annual Meeting*, 39:266, 1998.
Suh et al., "Synthetic triterpenoids activate a pathway for apoptosis in AML cells involving downregulation of FLIP and sensitization to TRAIL," *Leukemia*, 17:2122-2129, 2003.
Suh et al., "Synthetic triterpenoids enhance transforming growth factor β/Smad signaling," *Cancer Res.*, 63:1371-1376, 2003.
Suh et al., "Triterpenoids CDDO and CDDO-Me Down-Regulate FLIP Expression and Sensitize AML Cells to Trail-Induced Apoptosis," *American Society of Hematology 43rd Annual Meeting and Exposition*, Abstract No. 498, 2001.
Sun et al., "The synthetic triterpenoid, CDDO, suppresses alloreactive T cell responses and reduces murine early acute graft-versus-host disease mortality," *Biology of Blood and Marrow Transplantation*, 13:521-529, 2007.
Syftestad et al., "The in vitro chondrogenic response of limb-bud mesenchyme to a water-soluble fraction prepared from demineralized bone matrix," *Differentiation*, 29:230, 1985..
Tabe et al., "Chrmoatin-Mediated Transcriptional Activation with Novel Peroxisome Proliferator—Activated Receptor gamma(PPARgamma) Ligand 2-cyano-1,9-dien-28-oic Acid (CDDO) in Acute Promyelocytic Leukemia Cells," *Abstracts of the 44th Annual Meeting of the American Society of Hematology*, Abstract No. 2191, 2002.
Takabe et al., "Synthesis of lycosyl esters of oleanolic," *Carbohydrate Research*, 76:101-108, 1979, Database CAPLUS on STN AN:1980:42278.
Takahashi et al., "Increased expression of inducible and endothelial constitutive nitric oxide synthases in rat colon tumors induced by azoxymethane," *Cancer Res.*, 57:1233-1237, 1997.
Tamir and Tannebaum, "The role of nitric oxide (NO) in the carcinogenic process," *Biochim. Biophys. Acta*, 1288:F31-F36, 1996.
Tamm et al., "Expression and prognostic significance of IAP-family genes in human cancers and leukemias," *Blood*, 94(Suppl. 1):69a, Abstract # 298, 1999.
Tenenbaum and Heersche, "Differentiation of osteoblasts and formation of mineralized bone in vitro," *Calcif. Tissue Int.*, 34:76, 1982.
Toriumi et al., "Mandibular reconstruction with a recombinant bone-inducing factor. Functional, histologic, and biomechanical evaluation," *Arch. Otolaryngol. Head Neck Surg.*, 117:1101-1112, 1991.
Tsai et al., "Monoclonal antibody to human osteosarcoma: a novel Mr 26,000 protein recognized by murine hybridoma TMMR-2," *Cancer Res.*, 50:152-161, 1990.
Tsao et al., "DRIP205 co-activator overexpression enhances PPARgamma-mediated differentiation of leukemia cells by CDDO," *Proc. Amer. Assoc. Cancer Res.*, 46:1855, 2005.
Tsao et al., "Targeted Induction of Apoptosis in Leukemias by PPARgammma Ligation," *American Society of Hematology 43rd Annual Meeting and Exposition*, Abstract No. 2381, 2001.
Tsujii and DuBois, "Alterations in cellular adhesion and apoptosis in epithelial cells overexpressing prostaglandin endoperoxide synthase 2," *Cell*, 83:493-501, 1995.
Tsujii et al., "Cyclooxygenases regulates angiogenesis induced by colon cancer cells," *Cell*, 93:705-716, 1998.
Turksen et al., "Isolation of monoclonal antibodies recognizing rat bone-associated molecules in vitro and in vivo," *J. Histochem. Cytochem.*, 40:1339-1352, 1992.
Vazquez et al., "Human immunodeficiency virus type 1-induced macrophage gene expression includes the p21 gene, a target for viral regulation," *J. Virol.*, 79:4479-4491, 2005.

Vukicevic et al., "Stimulation of the expression of osteogenic and chondrogenic phenotypes in vitro by osteogenin," *Proc. Natl. Acad. Sci. USA*, 86:8793-7, 1989.
Walczak et al., "Tumoricidal activity of tumor necrosis factor-related apoptosis-inducing ligand in vivo", *Nature Medicine*, 5(2):157-163, 1999.
Walsh et al., "Monoclonal antibodies with selective reactivity against osteoblasts and osteocytes in human bone," *J. Bone Miner Res.*, 9:1687-1696, 1994.
Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.
Wang et al., "A synthetic triterpenoid, 2-cyano-3,12-dioxooleana-1,9-dien-28-oic acid (CDDO), is a ligand for the peroxisome proliferator-activated receptor γ," *Mol. Endocrinol.*, 14:1550-1556, 2000.
Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.
Warrell et al., "Differentiation therapy of acute promyelocytic leukemia with tretinoin (all-trans-retinoic acid)," *N. Engl. J. Med.*, 324(20):1385-1393, 1991.
Williams et al., "Immunology of multiple sclerosis," *Clin. Neurosci.*, 2(3-4):229-245, 1994.
Woodley, "Liposomes for Oral Administration of Drugs," *Crit. Rev. Therapeutic Drug Carrier System*, 2(1):1-18, 1985.
Xie et al., "Differential expression patterns in human myeloblastic leukemia HL-60 and multidrug resistant HL-60/Dox cells analyzed by human cDNA expression array," *Blood*, 92 (Suppl 1):387a, Abstract #1600. 1998.
Yates et al., "Pharmacodynamic characterization of chemopreventive triterpenoids as exceptionally potent inducers of Nrf2-regulated genes," *Mol. Cancer Ther.*, 6:154-162, 2007.
Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.*, 66:2488-2494, 2006.
Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me).," *Cancer & Biology Therapy*, 5(5):492-497, 2006.
Zapata et al., "CDDO and CDDO-Im Reduce Tumor Burden in a Transgenic Mouse Model of CLL," *Blood*, 104:3477, 2004.
Zapata et al., "Triterpenoids show activity against leukemic cells in a transgenic mouse model of CLL," *Proc. Amer. Assoc. Cancer Res.*, 46:5179, 2005.
Zhang et al., "Synthetic triterpenoid CDDO as effective therapy for HER2-expressing resistant breast cancer," *Proc. Amer. Assoc. Cancer Res.*, Abstract No. 3799, 2004.
Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.*, 123:380-387, 2004.
Zhou et al., "Carbon monoxide suppresses bleomycin-induced lung fibrosis," *Am J Pathol.*, 166(1):27-37, 2005.
Zou et al., "c-Jun NH2-terminal kinase-mediated up-regulation of death receptor 5 contributes to induction of apoptosis by the novel synthetic triterpenoid methyl-2-cyano-3,12-dioxooleana-1, 9-dien-28-oate in human lung cancer cells," *Cancer Res.*, 64:7570-7578, 2004.
Begum et al., "Synthesis of 2β-hydroxyursolic acid and other ursane analogs from ursonic acid," *Australian Journal of Chemistry*, 46 (7): 1067-1071, 1993.
Bowden et al., "Constituents of the fruit of *pseudopanax arboreum* (Araliaceae)," *Australian J. of Chemistry*, 28 (1): 91-107, 1975.
Campbell et al., "Endocyclic α,β-unsaturated ketones. VI. Ultraviolet and infrared absorption spectra and resonance stabalization," *Bioorganic and Medicinal Chemistry Letters*, 7(13): 1623-1628, 1997.
Chattopadhyay et al., "Studies on autoxidation: Part IV. Synthesis of isomeric 2,3-diols of olean-12-en-28-oate and isohopane (moretane)," *Indian J. of Chemistry, Section B: Organic Chemistry Including Medicinal Chemistry*, 15 (1): 21-24, 1977.

Devi et al., "Constituents of black dammar resin and some transformation products of α- and and β-amyrins," *Indian J. of Chemistry*, 7 (12): 1279-1280, 1969.

Elgamal et al., "Glycyrrhetic acid derivatives with modified ring A," *J. of Pharmaceutical Sciences*, 62 (9): 1557-1558, 1973.

Elgamal et al., "The C-2,C-3-glycol derivatives of glycyrrhetic acid," *Tetrahedron*, 30 (23/24): 4083-4087, 1974.

Endová et al., "Preparation of 2,3-secodiacids of the lupane series," *Collection of Czechoslovak Chemical Communications*, 59 (6): 1420-1429, 1994.

Evers et al., "Betulinic acid derivatives: a new class of human immunodeficiency virus type 1 specific inhibitors with a new mode of action," *J. of Medicinal Chemistry*, 39 (5): 1056-1068, 1996.

Ganguly et al., "Oxidation of ring in a lupeol," *Tetrahedron*, 22 (10): 3597-3599, 1966.

García-Granados et al., "Semi-synthesis of triterpene A-ring derivatives from oleanolic and maslinic acids. Theoretical and experimental $^{13}C$ chemical shifts," *J. of Chemical Research*, Synopses, 2: 56-57, 2000.

García-Granados et al., "Semi-synthesis of triterpene A-ring derivatives from oleanolic and maslinic acids. Part II. Theoretical and experimental $^{13}C$ chemical shifts," *J. of Chemical Research*, Synopses, 5: 211-212, 2000.

Glen et al., "Isolation of a new triterpenoid from rose-bay willow-herb," *Chemistry and Industry*, London, United Kingdom), 46: 1908, 1965.

Govindachari et al., "Gymnosporol, a new pentacyclic triterpene from *gymnosporia rothiana*," *Indian Journal of Chemistry*, 8 (5): 395-397, 1970.

Green and Long, "Compounds related to the steroid hormones. Part II. The action of hydrogen bromide on 2-bromo-3-oxo-$\Delta^1$-5α-steroids," *J. of the Chemical Society*, 2532-2543, 1961.

Hanna and Ourisson, "Studies of cyclic ketones. VIII. Preparation and properties of polycyclic α-diketones," *Bulletin de la Societe Chimique de France*, 1945-1951, 1961. (French only, but see attached English CAPLUS database summary.).

Hattori et al., "A triterpene from the fruits of *rubus chingii*," *Phytochemistry*, 27 (12): 3975-3976, 1988.

Huneck, "Triterpene, XIV: die bromierung von 19β28-epoxy-3-oxo-2-diazo-und-1-oxo-2-diazo-sowie von 19β28-epoxy-1-oxo-18α*H*-oleanan," *Chemische Berichte*, 98 (9): 2837-2843, 1965. (German only, but see attached English CAPLUS database summary.).

Khan et al., "α-amyrin derivatives from *corchorus depressus*," *Phytochemistry*, 30 (6): 1989-1992, 1991.

Klinot and Vystrcil, "Triterpenes. VII. Stereochemistry of 2-bromo derivatives of allobetuline and alloheterobetaline," *Collection of Czechoslovak Chemical Communications*, 31 (3): 1079-1092, 1966.

Klinot et al., "Triterpenes. Part LXXXVI. Triterpenoid 2,3-ketolis, diols and their acetates: preparation and conformation of the ring A," *Collection of Czechoslovak Chemical Communications*, 54 (2): 400-412, 1989.

Kumar and Seshadri, "Triterpenoids of *Pterocarpus santalinus*: constitution of a new lupene diol," *Phytochemistry*, 14 (2): 521-523, 1975.

Kundu et al., "Synthese von 2α-methoxycarbonyl-A-nor-lupa," *Chemische Beerichte*, 101 (9): 3255-3264, 1968. (German only, but see attached English CAPLUS database summary.).

Lavie and Shvo, "Constituents of Ecballium elaterium: proposed structure for elatericin A and B," *Chemistry and Industry*, (London, United Kingdom), 429-430, 1959.

Lawrie et al. "Isolation of derivatives of ursolic acid from apple skin," *Chemistry and Industry*, (London, United Kingdom), 41: 1720, 1966.

Lehn and Ourisson, "Syntheses in the lupane series," *Bulletin de la Societe Chimque de France*, 1133-1136, 1962. (French only, but see attached English CAPLUS database summary.).

Lehn and Vystreil, "Resonance magnetique nucleaire de produits naturels—VI : Triterpènes dérivés de la bétuline," *Tetrahedron*, 19 (11): 1733-1745, 1963. (English abstract).

Lehn and Ourisson, "Nuclear magnetic response (N.M.R.) of natural products. I. General introduction. Triterpenes of the lupane series.

Methyl groups," *Bulletin de la Societe Chimique de France*, 1137-1142, 1962. (French only, but see attached English CAPLUS database summary.).

Li et al., "Studies on constituents of Rosa multiflora thunb," *Zhongguo Yaoke Dazue Xuebao*, 33 (3): 184-187, 2002. (Chinese only, but see attached English CAPLUS database summary.).

Lugemwa et al., "A heliothis zea antifeedant from the abundant birchbark triterpene betulin", *Journal of Agricultural and Food Chemistry*, 38 (2): 493-496, 1990.

Mane and Ingle, "Synthesis and biological activity of some new 1,5-benzothiazepines containing thiazole moiety: 2-aryl-4-(4-methyl-2-substituted-aminothiazol-5-yl)-2,3-dihydro-1,5-benzothiazepines," *Indian Journal of Chemistry, Section B: Organic Chemistry Including Medicinal Chemistry*, 21B (10): 973-974, 1982.

Manzoor-i-Khuda and Habermehl, "Chemical constituents of Corchorus capsularis and C. olitorium (jute plant). III. Structure of corosin," *Zeitschrifi fuer Naturforschung, Teil C: Biochemie, Biophysik, Biologie, Virologie*, 29 (5-6): 209-221, 1974.

Manzoor-i-Khuda, "Isolation techniques for active principles from plants and their composition and structure determination through spectroscopic techniques," *New Trends Nat. Prod*, 26: 303-323, 1986.

Misra et al., "Studies on autoxidation: Part II—synthesis of isomeric 2,3-diols of Δ12-oleanene," *Indian J. of Chemistry, Section B: Organic Chemistry Including Medicinal Chemistry*, 14B (6): 411-414, 1976.

Osman et al., "Application of chemical reactions on thin-layer chromatoplates. IV. Triterpene," *Bulletin of the Chemical Society of Japan*, 47 (8): 2056-2058, 1974.

Osman et al., "Chemical studies on pentacyclic triterpenes. I. Benzilic acid rearrangement of ring A in ursolic acid," *Egyptian J. of Chemistry*, 15 (3): 269-272, 1972.

Picard et al., "Structure of the triterpenes," *J. Soc. Chem. Ind.*, 58: 58-59, 1939.

Pitzele, "Synthesis of 2-oxygenated glycyrrhetic acid derivatives," *J. of Medicinal Chemistry*, 117 (2): 191-194, 1974.

Pradhan and De, "Preparation of triterpenoid diosphenol via oximinoketone and structure of baccatin," *Indian J. of Chemistry, Section B: Organic Chemistry including Medicinal Chemistry*, 21B (9): 823-828, 1982.

Pradhan and Ghosh, "Studies on reactions of 2-bromo-3-ketotriterpenoids: Part IV. Debromination and dehydrobromination of 2α-bromo and 2,2-dibromo derivatives of lupanone and methyl dihydrobetulonate," *Indian J. of Chemistry, Section B: Organic Chemistry including Medicinal Chemistry*, 33B (1): 73-75, 1994.

Sejbal et al., "Triterpenes. Part LXXIII. Reactions of triterpenoid ketones with sulfur and morpholine under Willgerodt-Kindler reaction conditions," *Collection of Czechoslovak Chemical Communications*, 51 (1): 118-127, 1986.

Sejbal et al., "Triterpenes. Part XC. Conversion of betulin into careyagenolide (2α,3β-dihydroxy-18α, 19βH-ursan-28, 20β-olide," *Collection of Czechoslovak Chemical Communications*, 54 (4): 1036-1042, 1989.

Shimao and Oae, "The Wallach rearrangement of some 4,4'-disubstituted azoxybenzenes," *Bulletin of the Chemical Society of Japan*, 56 (2): 643-644, 1983.

Witz et al., "Cyclic ketones. XIII. Circular dichroism of steroid and triterpene ketones. Conformation of ring A of 8-methylated 3-oxotriterpenes," *Bull. Soc. China*, France: 1101-1112, 1963. (French only, but see attached English CAPLUS database summary.).

Karin, "Nuclear factor-kappaB in cancer development and progression," *Nature*, 441:431-436.

Liby et al., "Triterpenoids and rexinoids as multifunctional agents for the prevention and treatment of cancer," *Nature Reviews*, 7:357-69.

International Preliminary Report on Patentability issued in PCT/US2007/085006, dated July 14, 2009.

International Search Report issued in PCT/US2007/085006, dated Aug. 7, 2009.

Niikura et al., "The effects of synthetic triterpenoids on SZP synthesis in articular chondrocytes," *Osteoarthritis and Cartilage*, 14: S112-S113, 2006.

Niikura et al., "The effects synthetic triterpenoids on superficial zone protein synthesis in the articular chondrocytes," Abstract submitted 53rd meeting of the Orthopedic Research Society, San Diego 2007.

Vincenti et al., "The synthetic triterpenoid TP-222 inhibits RANKL induction of differentiation and MMP-9 gene expression in osteoclasts," abstract presented at *70th Annual Scientific meeting of the American College of Rheumatology 41st Annual Scientific Meeting*, 2006.

* cited by examiner

SYNTHETIC TRITERPENOIDS AND TRICYCLIC-BIS-ENONES FOR USE IN STIMULATING BONE AND CARTILAGE GROWTH

The present application claims the benefit of priority to U.S. Provisional Application No. 60/866,344, filed Nov. 17, 2006, the entire contents of this application being incorporated by reference.

The government owns rights in the present invention pursuant to grant numbers CA-078814 and CA-105294 from the National Institutes of Health.

BACKGROUND OF THE INVENTION

I. Field of the Invention

The present invention relates generally to the fields of biology and medicine. More particularly, it concerns compositions and methods for promoting bone and cartilage growth and repair.

II. Description of Related Art

The development of a functional tissue such as bone requires the concerted action of a number of microenvironmental signals: cytokines/growth factors, extracellular matrix (ECM) molecules, and cell:cell interactions. Moreover, these regulatory signals must be queued in the appropriate temporal and spatial order, resulting in a developmental microenvironment that facilitates three-dimensional growth. The skeletal system is no exception to such requirements. It is well understood that a number of cytokines/growth factors, such as TGF-β1 family members, modulate bone formation, and that ECM molecules like osteonectin, osteocalcin, and Type I and II collagen, etc., are important in both osteogenesis and chondrogenesis.

Current methods for the repair of bone defects include grafts of organic and synthetic construction. Three types of organic grafts are commonly used: autografts, allografts, and xenografts. An autograft is tissue transplanted from one site to another in the patient, and thus benefits from the absence of an immune response. However, using an autograft requires a second surgical site, increasing the risk of infection. Further, bone for grafting comes from a limited number of sites, e.g., the fibula, ribs and iliac crest. An allograft is tissue taken from a different organism of the same species, and a xenograft from an organism of a different species. These tissues are readily available in larger quantities than autografts, but genetic differences between the donor and recipient may lead to rejection of the graft. All have advantages and disadvantages, yet none provides an ideal replacement for missing bone. Thus, there exists a need for improved to repair and/or replace bone in subjects suffering from bone disease or trauma.

Articular cartilage is also recalcitrant to regeneration. Articular cartilage has discrete zone of cells including superficial zone, middle zone, and deep zone. The superficial zone chondrocytes secrete superficial protein (SZP) which is encoded by the gene PRG4, homologous to lubricin, and functions as a lubricant in articular joints. In contrast, the chondrocytes in the middle or deep zones of cartilage exhibit little capacity for SZP synthesis. Moreover, camptodactyl-arthropathy-coxa-vara-pericarditis syndrome (CACP) is known to be caused by mutations in the PRG4 gene which encodes SZP. Understanding of the regulators of SZP synthesis is important for investigating disease, homeostasis of articular joint, and tissue engineering of functional superficial zone articular cartilage. Transforming growth factor-β (TGF-β) is known to possess a capacity to up-regulate SZP synthesis in articular chondrocytes (Palcy et al., 1999). Methods are needed to modula TGF-β/Smad signaling in articular chondrocytes in order to provide improved treatments for the repair and/or regeneration of articular cartilage.

SUMMARY OF THE INVENTION

The present invention provides improved methods of treatment for bone or cartilage disease or trauma. These methods include the repair or replacement bone or cartilage. The methods are provide treatment for diseases resulting in bone or cartilage degeneration or decay.

Thus in some embodiments of the invention, there is provided a method for stimulating a bone- and/or cartilage-forming cell comprising: (a) providing a bone- or cartilage-producing cell or precursor thereof; (b) contacting said cell with a compound having the structure Q:

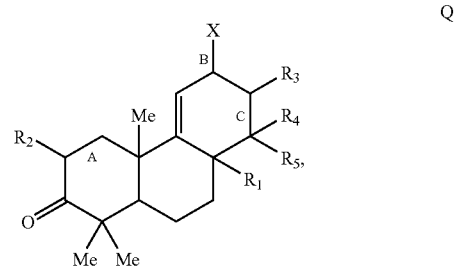

wherein either $R_1$ is cyano or substituted or unsubstituted versions of $C_1$-$C_{15}$-alkyl, $C_2$-$C_{15}$-alkenyl, $C_2$-$C_{15}$-alkynyl, $C_7$-$C_{15}$-aralkyl, $C_2$-$C_{15}$-heteroaralkyl, or $C_1$-$C_{15}$-acyl, and $R_2$, $R_3$, $R_4$, and $R_5$ are each independently —H, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-hetaryloxy, $C_2$-$C_{15}$-hetaralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-hetarylamino, $C_2$-$C_{15}$-hetaralkylamino, or $C_2$-$C_{15}$-amido, or $R_1$ and $R_4$ are methyl, $R_2$ is —H, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, or $C_2$-$C_{15}$-amido, $R_3$ and $R_5$ are both replaced by a group having the structure shown below, with the bond to $R_3$, in the structure above, attached to the carbon atom labeled "3" in the structure below, and, with the bond to $R_5$, in the structure above, attached to the carbon atom labeled "5" in the structure:

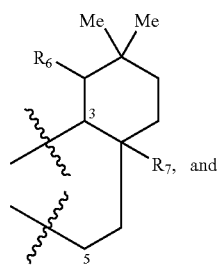

$R_6$ is hydrogen, $R_7$ is H, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_7$-$C_{15}$-aralkyl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, or $C_2$-$C_{15}$-amido; further wherein X is selected from the group consisting of —H and =O; A, B, and C each independently signifies a single- or double-bond, provided that (1) when C is a double-bond, $R_4$ is absent, (2) when B is a double bond, X is =O, (3) when B is a single bond, X is —H; any ketone group shown in the above structure may replaced by its enol tautomer, and pharmaceutically acceptable salts, hydrates, and optical isomers thereof; and (c) culturing the cell. In some embodiments, one or more of steps (a), (b) and (c) occur in one discrete step. In other embodiments, one or more of steps (a), (b) and (c) occurs in 1, 2, 3, 4, 5, 6, 7, 8, 9, 10, or more discrete steps. Those of skill in the art will recognize that the cell may also be cultured prior to contacting. In certain of these embodiments, the cartilage-producing cell is a chondrocyte.

In some embodiments, the method for stimulating a bone- and/or cartilage-forming cell further comprises incubating the cell with a growth factor. In some of these embodiments, the growth factor is TGF-β1, TGF-β2, TGF-β1.2, VEGF, insulin-like growth factor I or II, BMP2, BMP4, or BMP7. In other of these embodiments, the growth factor is parathyroid hormone, calcitonin, interleukin-6, or interleukin-11. In certain embodiments, this incubation step can occur either before, after, or at the same time as steps a and b. Those of skill in the art will recognize that the incubation step may occur before, after or simultaneously with any, or all of, steps (a), (b), (c), or any additional step employed. For example, in some of these embodiments, the incubation step occurs after steps (a), (b), and (c). In other embodiments it occurs before either steps (a), (b) or (c). In other embodiments, the incubation step occurs simultaneously with step (b). In some embodiments, steps (a), (b), (c) and the incubation occurs in one discrete step. In other embodiments, steps (a), (b), (c) and/or the incubation occur in 1, 2, 3, 4, 5, 6, 7, 8, 9, 10, or more discrete steps.

In certain embodiments, the method for stimulating a bone- and/or cartilage-forming cell further comprises purifying the cell or precursor. For example, in some of these embodiments, the purifying step occurs after steps (a), (b), and (c). In other embodiments it occurs before either steps (a), (b) or (c). In other embodiments, the purifying step occurs simultaneously with step (b). In some embodiments, steps (a), (b), (c) and the purifying occurs in one discrete step. In other embodiments, steps (a), (b), (c) and/or the purifying occur in 1, 2, 3, 4, 5, 6, 7, 8, 9, 10, or more discrete steps.

In some embodiments, the method for stimulating a bone- and/or cartilage-forming cell further comprises implanting said cell in vivo after step (b) and/or step (c). In certain embodiments, the method for stimulating a bone- and/or cartilage-forming cell results in the formation of bone by said cell. In some embodiments, the method for stimulating a bone- and/or cartilage-forming cell results in the formation of cartilage by said cell.

In other embodiments of the invention, there is provided a method of providing bone tissue to a mammal comprising: (a) providing a bone- or cartilage-producing cell or precursor thereof; (b) contacting said cell with a compound having the structure Q; (c) culturing the cell to form bone and/or cartilage; and (d) implanting said bone and/or cartilage to said subject. In some embodiments, one or more of steps (a), (b), (c) and (d) occur in one discrete step. In other embodiments, one or more of steps (a), (b), (c) and (d) occurs in 1, 2, 3, 4, 5, 6, 7, 8, 9, 10, or more discrete steps. Those of skill in the art will recognize that the cell may also be cultured prior to contacting.

In certain embodiments, the bone and/or cartilage formed may be part of a three-dimensional matrix. In certain of these embodiments, the three-dimensional matrix is one or more of alginate gels, collagen gels, or fibrin gels. In other of these embodiments, the three-dimensional matrix comprises one or more of polylactic acid, polyglycolic acid or PGLA. In some embodiments, the three-dimensional matrix comprises one or more of hydroxyapatite or other apatitic compounds, devitalized animal bone, devitalized human bone, or porous ceramic structures.

In some embodiments, the implantation is made in conjunction with orthopedic surgery and/or orthopedic devices, such as hip implants, knee implants, or spinal fusions. In other embodiments, the implantation may be made in conjunction with oral surgery and/or dental implants. In still other embodiments, the implantation may be made in conjunction with plastic surgery. In some embodiments, the implantation may be in conjunction with periodontal repairs.

In certain embodiments, the implantation may be into bone-forming tissue or a bone-repair site. In some embodiments, the implantation is into a wound. In other embodiments, the mammal has a bone disease such as cancer bone disease, localized osteolysis due to cancer and to myeloma, degenerative cartilage conditions, osteoarthritis, osteoporosis, Vitamin D deficiency, Osteotitis deformans, or Von Recklinghausen's Disease.

In other embodiments of the invention, there is provided a method for producing bone ex vivo comprising: (a) providing bone- or cartilage-producing cell or precursor thereof; (b) contacting said cell with a compound having the structure Q; (c) culturing the cell to form bone and/or cartilage. In some embodiments, one or more of steps (a), (b) and (c) occur in one discrete step. In other embodiments, one or more of steps (a), (b) and (c) occurs in 1, 2, 3, 4, 5, 6, 7, 8, 9, 10, or more discrete steps. Those of skill in the art will recognize that the cell may also be cultured prior to contacting. In some embodiments, the bone and/or cartilage formed may be part of a three-dimensional matrix.

In other embodiments of the invention, there is provided a method of repairing bone or cartilage damage in a subject comprising administering to said subject a compound having the structure Q. In some of these embodiments, the compound is administered to a wound or bone disease site. In certain embodiments, the bone disease may be cancer bone disease, localized osteolysis due to cancer and to myeloma, degenerative cartilage conditions, osteoarthritis, osteoporosis, Vitamin D deficiency, Osteotitis deformans, or Von Recklinghausen's Disease. In other of these embodiments, the wound may be a fracture. In some embodiments, bone is formed as part of the method. In certain embodiments, cartilage is formed as part of the method.

In some embodiments of any of the methods described above, the compound is a synthetic triterpenoid. In some of these embodiments, the synthetic triterpenoid has the structure:

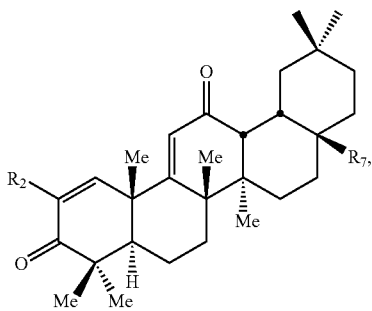

wherein $R_2$ is —H, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-aryl amino, $C_7$-$C_{15}$-aralkylamino, $C_1$-$C_{15}$-heteroaryl amino, $C_2$-$C_{15}$-heteroaralkylamino, or $C_2$-$C_{15}$-amido; $R_7$ is H, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_7$-$C_{15}$-aralkyl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-aryl amino, $C_7$-$C_{15}$-aralkylamino, $C_1$-$C_{15}$-heteroaryl amino, $C_2$-$C_{15}$-heteroaralkylamino, or $C_2$-$C_{15}$-amido; further wherein any ketone group shown in the above structure may replaced by its enol tautomer, and pharmaceutically acceptable salts, and hydrates thereof.

In some specific embodiments, the synthetic triterpenoid may be defined as

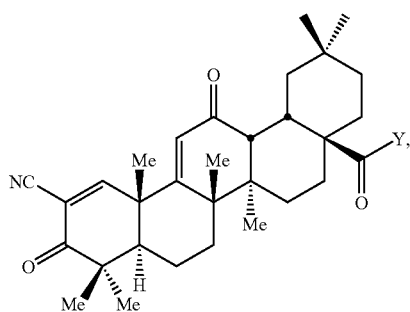

wherein Y is —H, hydroxy, amino, halo, or a substituted of unsubstituted version of $C_1$-$C_{14}$-alkoxy, $C_2$-$C_{14}$-alkenyloxy, $C_2$-$C_{14}$-alkynyloxy, $C_6$-$C_{14}$-aryloxy, $C_7$-$C_{14}$-aralkoxy, $C_1$-$C_{14}$-heteroaryloxy, $C_2$-$C_{14}$-heteroaralkoxy, $C_1$-$C_{14}$-acyloxy, $C_1$-$C_{14}$-alkylamino, $C_2$-$C_{14}$-alkenylamino, $C_2$-$C_{14}$-alkynylamino, $C_6$-$C_{14}$-arylamino, $C_7$-$C_{14}$-aralkylamino, $C_1$-$C_{14}$-heteroarylamino, $C_2$-$C_{14}$-heteroaralkylamino, $C_1$-$C_{14}$-alkylthio, $C_6$-$C_{14}$-arylthio, $C_7$-$C_{14}$-aralkylthio, $C_1$-$C_{14}$-heteroarylthio, $C_2$-$C_{14}$-heteroaralkylthio, or $C_0$-$C_{14}$-silyl, and substantially free pharmaceutically acceptable salts and hydrates thereof.

In certain of these embodiments, Y is hydroxy, methoxy, ethyl-amino, or

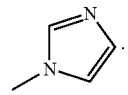

In some embodiments of any of the methods described above, the compound is a tricyclic bis-enone (TBE). In some of these embodiments, the TBE is further defined as

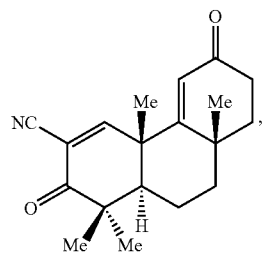

substantially free from other optical isomers. In other of these embodiments, the TBE is further defined as

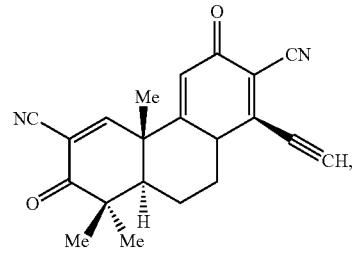

substantially free from other optical isomers. In still other of these embodiments, the TBE has the structure:

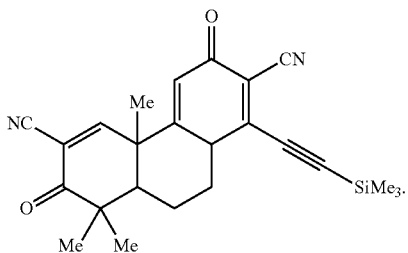

In some embodiments of any of the methods described above, the cell or precursor is of human origin. In other embodiments, the cell or precursor is of bovine, equine, canine, feline, murine, rat or chick origin.

It is contemplated that any method or composition described herein can be implemented with respect to any other method or composition described herein.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Invention

Figure 1:
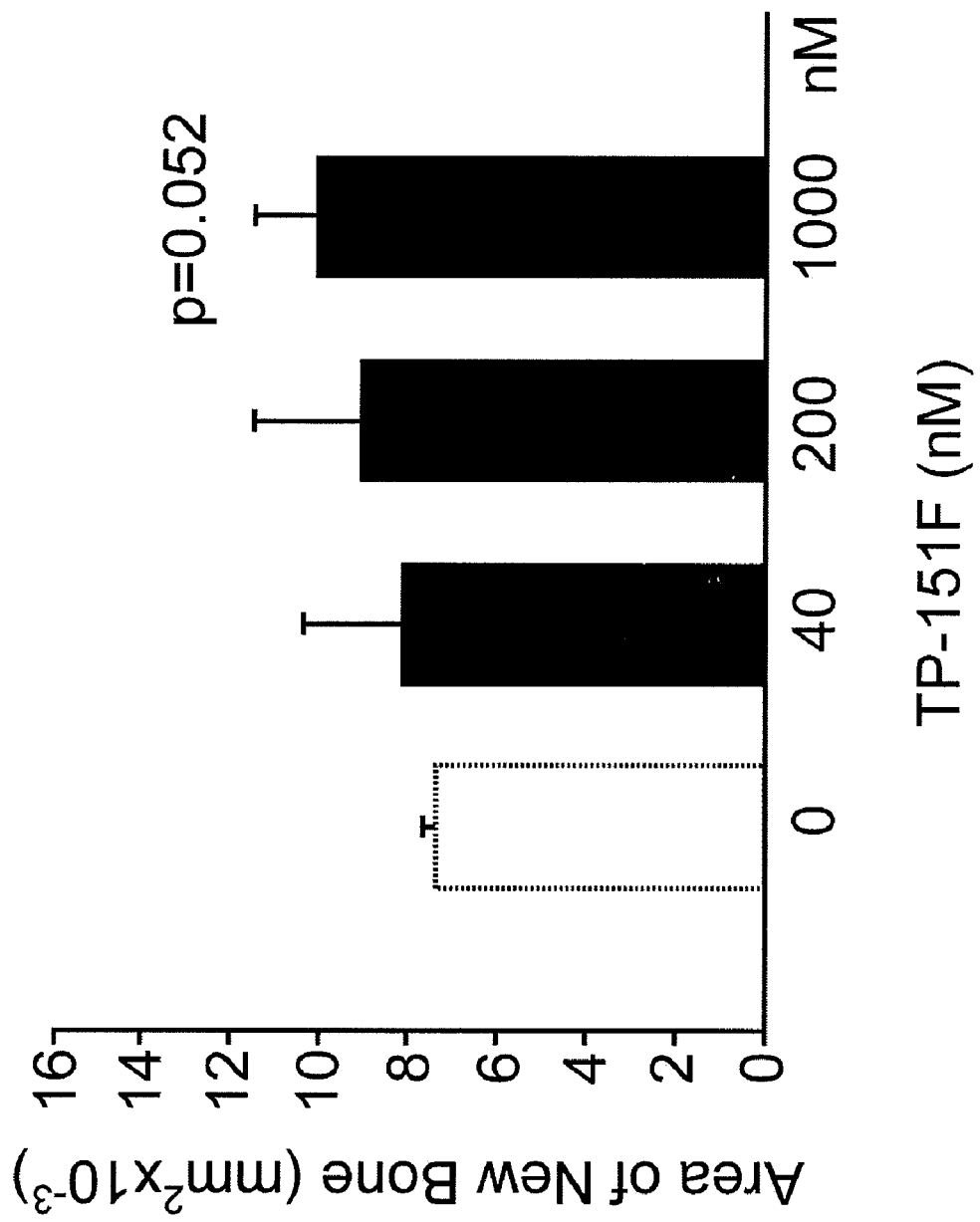
FIGS. 1, 4, 7 and 10—New bone growth following treatment with varying concentrations of drug. Bone formation was measured in vitro at 7 days at concentrations of 0, 40, 200 and 100 nM for each of TP-151F (FIG. 1), TP-155C (FIG. 4), TP-235H (FIG. 7) and TP-319A (FIG. 10). (The alphabet at the end of each compound number denotes the synthesis batch of each one.)

The rate of bone fractures in the United States is estimated at 6,000,000 individuals per year. When a bone is completely fractured, a significant number of fractures require medical intervention beyond simple immobilization (casting), particularly those involving trauma. A major problem in such instances is the lack of proximity of the two bone ends (referred to as non-union). This results in an inappropriate and prolonged repair process, which may prevent recovery. The average length of time for the body to repair a fracture is 25-100 days, for moderate load-bearing, and one year for complete repair. Thus, both simple fractures and medically complicated breaks would benefit from novel therapeutic modalities which accelerate and/or complete the repair process. The same is true for those bone diseases (referred to as osteopenias) which result in a thinning of the bone the primary symptom of which is an often-debilitating fracture, and other diseases in which bone strength or elasticity is compromised.

There is no curative treatment for lost bone mass. Likewise, there is no effective replacement or implant for non-union fractures or crush injuries of the bone. Currently, these latter types of injury utilize bovine (cow), or human cadaver bone which is chemically treated (to remove proteins) in order to prevent rejection. However, such bone implants, while mechanically important, are biologically dead (they do not contain bone-forming cells, growth factors, or other regulatory proteins). Thus, they do not greatly modulate the repair process.

Numerous new synthetic triterpenoids have been studied looking at their effects on transforming growth factor (TGF)-β/Smad signaling. These agents, at nanomolar concentrations, increase the expression of TGF-β-dependent genes, such as those for plasminogen activator inhibitor 1 and the type II TGF-β receptor, and they synergize with TGF-β in this regard. They prolong the activation of Smad2 induced by TGF-β and markedly enhance the ability of Smad3 to activate a Smad binding element, CAGA-luciferase. In transfection assays, they reverse the inhibitory effects of Smad7. They also enhance Smad signaling in the pathways of two other members of the TGF-β superfamily, namely, activin and bone morphogenetic protein. Finally, these triterpenoids induce expression of the transcriptional coactivator p300-CBP-associated factor and synergize with TGF-β in this regard. Because of these findings, the present inventors sought to determine if these agents had any effect on bone and cartilage formation.

As shown below in the Examples, the results revealed that all the triterpenoid compounds tested induced new bone formation, some more so than others. Some of the compounds tested also induced cartilage formation. The results also showed that the triterpenoid compounds induced elevated levels of alkaline phosphatase, which is consistent with rapid bone growth.

II. Definitions

As used herein, the term "amino" means $-NH_2$; the term "nitro" means $-NO_2$; the term "halo" designates $-F$, $-Cl$, $-Br$ or $-I$; the term "mercapto" means $-SH$; the term "cyano" means $-CN$; the term "silyl" means $-SiH_3$, and the term "hydroxy" means $-OH$.

The term "substituted," when used to modify a class of organic radicals (e.g. alkyl, aryl, acyl, etc.), means that one or more than one hydrogen atom of that radical has been replaced by a heteroatom, or a heteroatom containing group. Specific substituted organic radicals are defined more fully below.

The term "unsubstituted," when used to modify a class of organic radicals (e.g. alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group substituted. For example, the group $-C_6H_4C\equiv CH$ is an example of an unsubstituted aryl group, while $-C_6H_4F$ is an example of a substituted aryl group. Specific unsubstituted organic radicals are defined more fully below.

The term "unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, an unsubstituted $C_1$-$C_{10}$-alkyl has 1 to 10 carbon atoms. The term "alkyl" includes straight-chain alkyl groups, branched-chain alkyl groups, cycloalkyl (alicyclic) groups, alkyl substituted cycloalkyl groups, and cycloalkyl substituted alkyl groups. The groups, $-CH_3$, $-CH_2CH_3$, $-CH_2CH_2CH_3$, $-CH(CH_3)_2$, $-CH(CH_2)_2$, $-CH_2CH_2CH_2CH_3$, $-CH(CH_3)CH_2CH_3$, $-CH_2CH(CH_3)_2$, $-C(CH_3)_3$, and $-CH_2C(CH_3)_3$, are all examples of unsubstituted alkyl groups.

The term "substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a substituted $C_1$-$C_{10}$-alkyl has 1 to 10 carbon atoms. The following groups are all examples of substituted alkyl groups: trifluoromethyl, —$CH_2F$, —$CH_2Cl$, —$CH_2Br$, —$CH_2OH$, —$CH_2OCH_3$, —$CH_2OCH_2CH_3$, —$CH_2OCH_2CH_2CH_3$, —$CH_2OCH(CH_3)_2$, —$CH_2OCH(CH_2)_2$, —$CH_2OCH_2CF_3$, —$CH_2OCOCH_3$, —$CH_2NH_2$, —$CH_2NHCH_3$, —$CH_2N(CH_3)_2$, —$CH_2NHCH_2CH_3$, —$CH_2N(CH_3)CH_2CH_3$, —$CH_2NHCH_2CH_2CH_3$, —$CH_2NHCH(CH_3)_2$, —$CH_2NHCH(CH_2)_2$, —$CH_2N(CH_2CH_3)_2$, —$CH_2CH_2F$, —$CH_2CH_2Cl$, —$CH_2CH_2Br$, —$CH_2CH_2I$, —$CH_2CH_2OH$, $CH_2CH_2OCOCH_3$, —$CH_2CH_2NH_2$, —$CH_2CH_2N(CH_3)_2$, —$CH_2CH_2NHCH_2CH_3$, —$CH_2CH_2N(CH_3)CH_2CH_3$, —$CH_2CH_2NHCH_2CH_2CH_3$, —$CH_2CH_2NHCH(CH_3)_2$, —$CH_2CH_2NHCH(CH_2)_2$, —$CH_2CH_2N(CH_2CH_3)_2$, —$CH_2CH_2NHCO_2C(CH_3)_3$, and —$CH_2Si(CH_3)_3$.

The term "unsubstituted $C_n$-alkenyl" refers to a radical, having a linear or branched, cyclic or acyclic structure, further having at least one carbon-carbon double bond, a total of n carbon atoms, all of which are nonaromatic, 3 or more hydrogen atoms, and no heteroatoms. For example, an unsubstituted $C_2$-$C_{10}$-alkenyl has 2 to 10 carbon atoms. Unsubstituted alkenyl groups include: —$CH=CH_2$, —$CH=CHCH_3$, —$CH=CHCH_2CH_3$, —$CH=CHCH_2CH_2CH_3$, —$CH=CHCH(CH_3)_2$, —$CH=CHCH(CH_2)_2$, —$CH_2CH=CH_2$, —$CH_2CH=CHCH_3$, —$CH_2CH=CHCH_2CH_3$, —$CH_2CH=CHCH_2CH_2CH_3$, —$CH_2CH=CHCH(CH_3)_2$, and —$CH_2CH=CHCH(CH_2)_2$.

The term "substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a substituted $C_2$-$C_{10}$-alkenyl has 2 to 10 carbon atoms. The groups, —$CH=CHF$, —$CH=CHCl$ and —$CH=CHBr$, are examples of substituted alkenyl groups.

The term "unsubstituted $C_n$-alkynyl" refers to a radical, having a linear or branched, cyclic or acyclic structure, further having at least one carbon-carbon triple bond, a total of n carbon atoms, all of which are nonaromatic, at least one hydrogen atom, and no heteroatoms. For example, an unsubstituted $C_2$-$C_{10}$-alkynyl has 2 to 10 carbon atoms. The groups, —$C\equiv CH$ and —$C\equiv CCH_3$, are examples of unsubstituted alkynyl groups.

The term "substituted $C_n$-alkynyl" refers to a radical, having a single nonaromatic carbon atom as the point of attachment and at least one nonaromatic carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a substituted $C_2$-$C_{10}$-alkynyl has 2 to 10 carbon atoms. The group, —$C\equiv CSi(CH_3)_3$, is an example of a substituted alkynyl group.

The term "unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, an unsubstituted $C_6$-$C_{10}$-aryl has 6 to 10 carbon atoms. Examples of unsubstituted aryl groups include phenyl, methylphenyl, di(methyl)phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, —$C_6H_4CH=CH_2$, —$C_6H_4CH=CHCH_3$, —$C_6H_4C\equiv CH$, and —$C_6H_4C\equiv CCH_3$. Aryl groups also include polycyclic fused aromatic groups such as naphthyl, quinolyl, indolyl, and the like.

The term "substituted $C_n$-aryl" refers to a radical, having a single carbon atom as point of attachment, wherein the carbon atom is part of an aromatic ring structure containing only carbon atoms, further having a total of n aromatic or nonaromatic carbon atoms, 0, 1, or more than one hydrogen atom, and at least one nonaromatic heteroatom, wherein each heteroatom is independently selected from the group consisting of N, O, F, Cl, Br, I, Si, P, and S. For example, a substituted $C_6$-$C_{10}$-aryl has 6 to 10 carbon atoms. The groups, —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OCOCH_3$, —$C_6H_4OC_6H_5$, —$C_6H_4NH_2$, —$C_6H_4NHCH_3$, —$C_6H_4NHCH_2CH_3$, —$C_6H_4CH_2Cl$, —$C_6H_4CH_2Br$, —$C_6H_4CH_2OH$, —$C_6H_4CH_2OCOCH_3$, —$C_6H_4CH_2NH_2$, —$C_6H_4N(CH_3)_2$, —$C_6H_4CH_2CH_2Cl$, —$C_6H_4CH_2CH_2OH$, —$C_6H_4CH_2CH_2OCOCH_3$, —$C_6H_4CH_2CH_2NH_2$, —$C_6H_4CH_2CH=CH_2$, —$C_6H_4CF_3$, —$C_6H_4CN$, —$C_6H_4C\equiv CSi(CH_3)_3$, —$C_6H_4COH$, —$C_6H_4COCH_3$, —$C_6H_4COCH_2CH_3$, —$C_6H_4COCH_2CF_3$, —$C_6H_4COC_6H_5$, —$C_6H_4CO_2H$, —$C_6H_4CO_2CH_3$, —$C_6H_4CONH_2$, —$C_6H_4CONHCH_3$, and —$C_6H_4CON(CH_3)_2$ are examples of substituted aryl groups.

The term "unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, an unsubstituted $C_7$-$C_{10}$-aralkyl has 7 to 10 carbon atoms. An "aralkyl" includes an alkyl substituted with an aryl group. Examples of unsubstituted aralkyls include phenylmethyl (benzyl) and phenylethyl.

The term "substituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 0, 1, or more than one hydrogen atom, and at least one heteroatom, wherein each heteroatom is independently selected from the group consisting of N, O, F, Cl, Br, I, Si, P, and S. For example, a substituted $C_7$-$C_{10}$-aralkyl has 7 to 10 carbon atoms.

The term "unsubstituted $C_n$-heteroaryl" refers to a radical, having either a single aromatic carbon atom or a single aromatic heteroatom as the point of attachment, further having a total of n carbon atoms, at least one hydrogen atom, and at least one heteroatom, wherein at least one of the carbon atoms and all of the heteroatoms are incorporated into one or more aromatic ring structures, further wherein each heteroatom is independently selected from the group consisting of N, O, F, Cl, Br, I, Si, P, and S. For example, an unsubstituted $C_1$-$C_{10}$-heteroaryl has 1 to 10 carbon atoms. For example, the term "heteroaryl" includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like.

The term "substituted $C_n$-heteroaryl" refers to a radical, having either a single aromatic carbon atom or a single aromatic heteroatom as the point of attachment, further having a total of n carbon atoms, at least one hydrogen atom, and at least two heteroatoms, wherein at least one of the carbon atoms and at least one of the heteroatoms are incorporated into one or more aromatic ring structures, further wherein at least one of the heteroatoms is not part of the one or more aromatic ring structures, further wherein each heteroatom is independently selected from the group consisting of N, O, F, Cl, Br, I, Si, P, and S. For example, an substituted $C_1$-$C_{10}$-heteroaryl has 1 to 10 carbon atoms.

The term "unsubstituted $C_n$-heteroaralkyl" refers to a radical, having a single saturated carbon atom as the point of attachment, further having a total of n carbon atoms, at least three hydrogen atoms, and at least one heteroatom, wherein at least one of the carbon atoms and all of the heteroatoms form an aromatic ring structure, further wherein each heteroatom is independently selected from the group consisting of N, O, F, Cl, Br, I, Si, P, and S. For example, an unsubstituted $C_2$-$C_{10}$-heteroaralkyl has 2 to 10 carbon atoms.

The term "substituted $C_n$-heteroaralkyl" refers to a radical having a single saturated carbon atom as the point of attachment, further having a total of n carbon atoms, 0, 1, or more than one hydrogen atom, and at least two heteroatoms, wherein at least one of the carbon atoms and at least one of the heteroatoms are incorporated into one or more aromatic ring structures, further wherein at least one of the heteroatoms is not part of an aromatic ring structure, further wherein each heteroatom is independently selected from the group consisting of N, O, F, Cl, Br, I, Si, P, and S. For example, a substituted $C_2$-$C_{10}$-heteroaralkyl has 2 to 10 carbon atoms.

The term "unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, an unsubstituted $C_1$-$C_{10}$-acyl has 1 to 10 carbon atoms. The groups, —COH, —COCH$_3$, —COCH$_2$CH$_3$, —COCH$_2$CH$_2$CH$_3$, —COCH(CH$_3$)$_2$, —COCH(CH$_2$)$_2$, —COC$_6$H$_5$, —COC$_6$H$_4$CH$_3$, —COC$_6$H$_4$CH$_2$CH$_3$, —COC$_6$H$_4$CH$_2$CH$_2$CH$_3$, —COC$_6$H$_4$CH(CH$_3$)$_2$, —COC$_6$H$_4$CH(CH$_2$)$_2$, and —COC$_6$H$_3$(CH$_3$)$_2$, are examples of unsubstituted acyl groups.

The term "substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a substituted $C_1$-$C_{10}$-acyl has 1 to 10 carbon atoms. The term substituted acyl includes carbamoyl, thiocarboxylate, and thiocarboxylic acid groups. The groups, —COCH$_2$CF$_3$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —CONH$_2$, —CONHCH$_3$, —CONHCH$_2$CH$_3$, —CONHCH$_2$CH$_2$CH$_3$, —CONHCH(CH$_3$)$_2$, —CONHCH(CH$_2$)$_2$, —CON(CH$_3$)$_2$, —CON(CH$_2$CH$_3$)CH$_3$, —CON(CH$_2$CH$_3$)$_2$ and —CONHCH$_2$CF$_3$, are examples substituted acyl groups.

The term "unsubstituted $C_n$-alkoxy" refers to a group, having the structure —OR, in which R is an unsubstituted $C_n$-alkyl, as that term is defined above. Unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$.

The term "substituted $C_n$-alkoxy" refers to a group, having the structure —OR, in which R is a substituted $C_n$-alkyl, as that term is defined above. For example, —OCH$_2$CF$_3$ is a substituted alkoxy group.

The term "unsubstituted $C_n$-alkenyloxy" refers to a group, having the structure —OR, in which R is an unsubstituted $C_n$-alkenyl, as that term is defined above.

The term "substituted $C_n$-alkenyloxy" refers to a group, having the structure —OR, in which R is a substituted $C_n$-alkenyl, as that term is defined above.

The term "unsubstituted $C_n$-alkynyloxy" refers to a group, having the structure —OR, in which R is an unsubstituted $C_n$-alkynyl, as that term is defined above.

The term "substituted $C_n$-alkenyloxy" refers to a group, having the structure —OR, in which R is a substituted $C_n$-alkynyl, as that term is defined above.

The term "unsubstituted $C_n$-aryloxy" refers to a group, having the structure —OAr, in which Ar is an unsubstituted $C_n$-aryl, as that term is defined above. An example of an unsubstituted aryloxy group is —OC$_6$H$_5$.

The term "substituted $C_n$-aryloxy" refers to a group, having the structure —OAr, in which Ar is a substituted $C_n$-aryl, as that term is defined above.

The term "unsubstituted $C_n$-aralkyloxy" refers to a group, having the structure —OAr, in which Ar is an unsubstituted $C_n$-aralkyl, as that term is defined above.

The term "substituted $C_n$-aralkyloxy" refers to a group, having the structure —OAr, in which Ar is a substituted $C_n$-aralkyl, as that term is defined above.

The term "unsubstituted $C_n$-heteroaryloxy" refers to a group, having the structure —OAr, in which Ar is an unsubstituted $C_n$-heteroaryl, as that term is defined above.

The term "substituted $C_n$-heteroaryloxy" refers to a group, having the structure —OAr, in which Ar is a substituted $C_n$-heteroaryl, as that term is defined above.

The term "unsubstituted $C_n$-heteroaralkyloxy" refers to a group, having the structure —OAr, in which Ar is an unsubstituted $C_n$-heteroaralkyl, as that term is defined above.

The term "substituted $C_n$-heteroaralkyloxy" refers to a group, having the structure —OAr, in which Ar is a substituted $C_n$-heteroaralkyl, as that term is defined above.

The term "unsubstituted $C_n$-acyloxy" refers to a group, having the structure —OAc, in which Ac is an unsubstituted $C_n$-acyl, as that term is defined above. An unsubstituted acyloxy group includes alkylcarbonyloxy and arylcarbonyloxy groups. For example, —OCOCH$_3$ is an example of an unsubstituted acyloxy group.

The term "substituted $C_n$-acyloxy" refers to a group, having the structure —OAc, in which Ac is a substituted $C_n$-acyl, as that term is defined above. A substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, an unsubstituted $C_1$-$C_{10}$-alkylamino has 1 to 10 carbon atoms. An alkylamino group includes dialkylamino groups. An unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl.

The term "substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_1$-$C_{10}$-alkylamino has 1 to 10 carbon atoms.

The term "unsubstituted $C_n$-alkenylamino" refers to a radical, having a single nitrogen atom as the point of attachment, further having a linear or branched, cyclic or acyclic structure, containing at least one carbon-carbon double bond, a total of n carbon atoms, all of which are nonaromatic, 4 or more hydrogen atoms, a total of one nitrogen atom, and no additional heteroatoms. For example, an unsubstituted $C_2$-$C_{10}$-alkenylamino has 2 to 10 carbon atoms. An alkenylamino group includes dialkenylamino and alkyl(alkenyl)amino groups.

The term "substituted $C_n$-alkenylamino" refers to a radical, having a single nitrogen atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_2$-$C_{10}$-alkenylamino has 2 to 10 carbon atoms.

The term "unsubstituted $C_n$-alkynylamino" refers to a radical, having a single nitrogen atom as the point of attachment, further having a linear or branched, cyclic or acyclic structure, containing at least one carbon-carbon triple bond, a total of n carbon atoms, all of which are nonaromatic, at least one hydrogen atoms, a total of one nitrogen atom, and no additional heteroatoms. For example, an unsubstituted $C_2$-$C_{10}$-alkynylamino has 2 to 10 carbon atoms. An alkynylamino group includes dialkynylamino and alkyl(alkynyl)amino groups.

The term "substituted $C_n$-alkynylamino" refers to a radical, having a single nitrogen atom as the point of attachment, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_2$-$C_{10}$-alkynylamino has 2 to 10 carbon atoms.

The term "unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, an unsubstituted $C_6$-$C_{10}$-arylamino has 6 to 10 carbon atoms. An arylamino group includes diarylamino and alkyl(aryl)amino groups.

The term "substituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 0, 1, or more hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_6$-$C_{10}$-arylamino has 6 to 10 carbon atoms.

The term "unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, an unsubstituted $C_7$-$C_{10}$-aralkylamino has 7 to 10 carbon atoms. An aralkylamino group includes diaralkylamino, alkyl(aralkyl)amino, and aryl(aralkyl)amino groups.

The term "substituted $C_n$-aralkylamino" refers to a radical, having a single nitrogen atom as the point of attachment, further having at least one or two saturated carbon atoms attached to the nitrogen atom, further having a total of n carbon atoms, wherein at least 6 of the carbon atoms form an aromatic ring structure containing only carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_7$-$C_{10}$-aralkylamino has 7 to 10 carbon atoms.

The term "unsubstituted $C_n$-heteroarylamino" refers to a radical, having a single nitrogen atom as the point of attachment, further having a total of n carbon atoms, at least one hydrogen atom, and at least one additional heteroatom, in addition to the nitrogen atom at the point of attachment, wherein at least one of the carbon atoms and all of the additional heteroatoms are incorporated into one or more aromatic ring structures, further wherein each additional heteroatom is independently selected from the group consisting of N, O, F, Cl, Br, I, Si, P, and S. For example, an unsubstituted $C_1$-$C_{10}$-heteroarylamino has 1 to 10 carbon atoms. A heteroarylamino group includes alkyl(heteroaryl)amino and aryl(heteroaryl)amino groups.

The term "substituted $C_n$-heteroarylamino" refers to a radical, having a single nitrogen atom as the point of attachment, further having a total of n carbon atoms, at least one hydrogen atom, at least two additional heteroatoms, that is, in addition to the nitrogen atom at the point of attachment, wherein at least one of the carbon atoms and at least one of the additional heteroatoms are incorporated into one or more aromatic ring structures, further wherein at least one of the additional heteroatoms is not part of the one or more aromatic ring structures, further wherein each additional heteroatom is independently selected from the group consisting of N, O, F, Cl, Br, I, Si, P, and S. For example, an substituted $C_1$-$C_{10}$-heteroarylamino has 1 to 10 carbon atoms.

The term "unsubstituted $C_n$-heteroaralkylamino" refers to a radical, having a single nitrogen atom as the point of attachment, further having one or two saturated carbon atoms attached to the nitrogen atom, further having a total of n carbon atoms, at least three hydrogen atoms, at least one additional heteroatom, wherein at least one of the carbon atoms and all of the additional heteroatoms form an aromatic ring structure, further wherein each additional heteroatom is independently selected from the group consisting of N, O, F, Cl, Br, I, Si, P, and S. For example, an unsubstituted $C_2$-$C_{10}$-heteroaralkylamino has 2 to 10 carbon atoms. A heteroaralkylamino group includes alkyl(heteroaralkyl)amino and aryl(heteroaralkyl)amino groups.

The term "substituted $C_n$-heteroaralkylamino" refers to a radical, having a single nitrogen atom as the point of attachment, further having one or two saturated carbon atoms attached to the nitrogen atom, further having a total of n carbon atoms, 0, 1, or more than one hydrogen atom, at least two additional heteroatoms, that is, in addition to the nitrogen atom at the point of attachment, wherein at least one of the carbon atoms and at least one of the additional heteroatoms are incorporated into one or more aromatic ring structures, further wherein at least one of the heteroatoms is not part of an aromatic ring structure, further wherein each heteroatom is independently selected from the group consisting of N, O, F, Cl, Br, I, Si, P, and S. For example, a substituted $C_2$-$C_{10}$-heteroaralkylamino has 2 to 10 carbon atoms.

The term "unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, an unsubstituted $C_1$-$C_{10}$-amido has 1 to 10 carbon atoms. A amido group includes N-alkyl-amido, N-aryl-amido, N-aralkyl-amido, acylamino, alkylcarbonylamino, arylcarbonylamino, and ureido groups. The group, —NHCOCH$_3$, is an example of an unsubstituted amido group.

The term "substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a substituted $C_1$-$C_{10}$-amido has 1 to 10 carbon atoms. The group, —NHCO$_2$C(CH$_3$)$_3$, is an example of an substituted amido group.

The term "unsubstituted $C_n$-alkylthio" refers to a group, having the structure —SR, in which R is an unsubstituted $C_n$-alkyl, as that term is defined above. The group, —SCH$_3$, is an example of an unsubstituted alkylthio group.

The term "substituted $C_n$-alkylthio" refers to a group, having the structure —SR, in which R is a substituted $C_n$-alkyl, as that term is defined above.

The term "unsubstituted $C_n$-alkenylthio" refers to a group, having the structure —SR, in which R is an unsubstituted $C_n$-alkenyl, as that term is defined above.

The term "substituted $C_n$-alkenylthio" refers to a group, having the structure —SR, in which R is a substituted $C_n$-alkenyl, as that term is defined above.

The term "unsubstituted $C_n$-alkynylthio" refers to a group, having the structure —SR, in which R is an unsubstituted $C_n$-alkynyl, as that term is defined above.

The term "substituted $C_n$-alkenylthio" refers to a group, having the structure —SR, in which R is a substituted $C_n$-alkynyl, as that term is defined above.

The term "unsubstituted $C_n$-arylthio" refers to a group, having the structure —SAr, in which Ar is an unsubstituted $C_n$-aryl, as that term is defined above. The group, —SC$_6$H$_5$, is an example of an unsubstituted arylthio group.

The term "substituted $C_n$-arylthio" refers to a group, having the structure —SAr, in which Ar is a substituted $C_n$-aryl, as that term is defined above.

The term "unsubstituted $C_n$-aralkylthio" refers to a group, having the structure —SAr, in which Ar is an unsubstituted $C_n$-aralkyl, as that term is defined above. The group, —SCH$_2$C$_6$H$_5$, is an example of an unsubstituted aralkyl group.

The term "substituted $C_n$-aralkylthio" refers to a group, having the structure —SAr, in which Ar is a substituted $C_n$-aralkyl, as that term is defined above.

The term "unsubstituted $C_n$-heteroarylthio" refers to a group, having the structure —SAr, in which Ar is an unsubstituted $C_n$-heteroaryl, as that term is defined above.

The term "substituted $C_n$-heteroarylthio" refers to a group, having the structure —SAr, in which Ar is a substituted $C_n$-heteroaryl, as that term is defined above.

The term "unsubstituted $C_n$-heteroaralkylthio" refers to a group, having the structure —SAr, in which Ar is an unsubstituted $C_n$-heteroaralkyl, as that term is defined above.

The term "substituted $C_n$-heteroaralkylthio" refers to a group, having the structure —SAr, in which Ar is a substituted $C_n$-heteroaralkyl, as that term is defined above.

The term "unsubstituted $C_n$-acylthio" refers to a group, having the structure —SAc, in which Ac is an unsubstituted $C_n$-acyl, as that term is defined above. The group, —SCOCH$_3$, is an example of an unsubstituted acylthio group.

The term "substituted $C_n$-acylthio" refers to a group, having the structure —SAc, in which Ac is a substituted $C_n$-acyl, as that term is defined above.

The term "unsubstituted $C_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, an unsubstituted $C_1$-$C_{10}$-alkylsilyl has 1 to 10 carbon atoms. An alkylsilyl group includes dialkylamino groups. The groups, —Si(CH$_3$)$_3$ and —Si(CH$_3$)$_2$C(CH$_3$)$_3$, are examples of unsubstituted alkylsilyl groups.

The term "substituted $C_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a substituted $C_1$-$C_{10}$-alkylsilyl has 1 to 10 carbon atoms.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methane-sulfonate, maleate, and the like. Other suitable salts are known to one of ordinary skill in the art.

Suitable pharmaceutically acceptable salts may also be formed by reacting the agents of the invention with an organic base such as methylamine, ethylamine, ethanolamine, lysine, ornithine and the like. Other suitable salts are known to one of ordinary skill in the art.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use—A Handbook, by C. G. Wermuth and P. H. Stahl, Verlag Helvetica Chimica Acta, 2002, which is incorporated herein by reference.

As used herein, the term "patient" is intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A patient can be a human suffering from a neurodegenerative disease, such as Alzheimer's disease, or Parkinson's disease.

As used herein, the term "$IC_{50}$" refers to an inhibitory dose which is 50% of the maximum response obtained.

As used herein, the term "water soluble" means that the compound dissolves in water at least to the extent of 0.010 mole/liter or is classified as soluble according to literature precedence.

As used herein, predominantly one enantiomer means that the compound contains at least 95% of one enantiomer, or more preferably at least 98% of one enantiomer, or most preferably at least 99% of one enantiomer. For example, a compound may contain 99% (+) TBE-31 and 1% (−) TBE-31.

Other abbreviations used herein are as follows: DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFN-γ, interferon-γ; LPS, bacterial endotoxic lipopolysaccharide; TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid.

The use of the word "a" or "an" when used in conjunction with the term "comprising" or "having" in the claims and/or the specification may mean "one," but it is also consistent with the meaning of "one or more," "at least one," and "one or more than one." As used herein "another" may mean at least a second or more.

III. Synthetic Triterpenoids and TBEs

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang et al., 1994; Nishino et al., 1988). However, the biological activity of these naturally-occurring molecules is relatively weak, and therefore the synthesis of new analogs to enhance their potency was undertaken (Honda et al., 1997; Honda et al., 1998). Subsequent research by the inventors has identified a number of synthetic compounds that have improved activity as compared to the naturally-occurring triterpenoids.

A. CDDO Family Compounds

The ongoing efforts for the improvement of anti-inflammatory and antiproliferative activity of oleanolic and ursolic acid analogs led to the discovery of 2-cyano-3,12-dioxooleane-1,9(11)-dien-28-oic acid (CDDO) and related compounds (e.g., CDDO-Me, TP-225, CDDO-Im) (Honda et al., 1997, 1998, 1999, 2000a, 2000b, 2002; Suh et al., 1998; 1999; 2003; Place et al., 2003; Liby et al., 2005). Clinical trials of CDDO (TP-151) and CDDO-Me (TP-155) as anti-cancer drugs started in 2005.

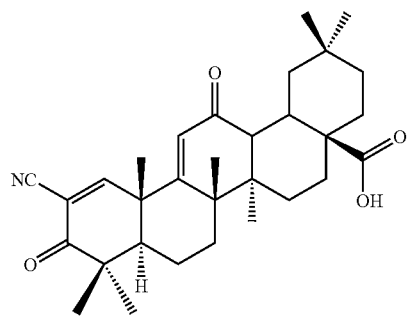

CDDO (TP-151)

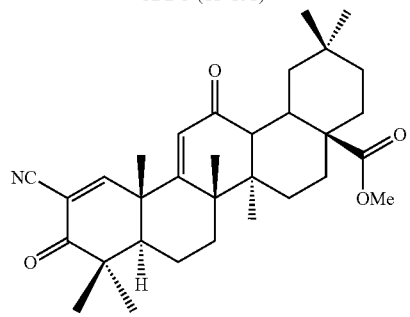

CDDO-Me (TP-155)

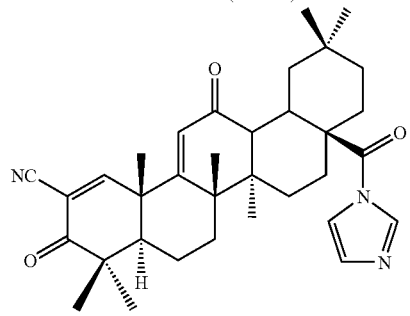

CDDO-Im (TP-235)

19
-continued

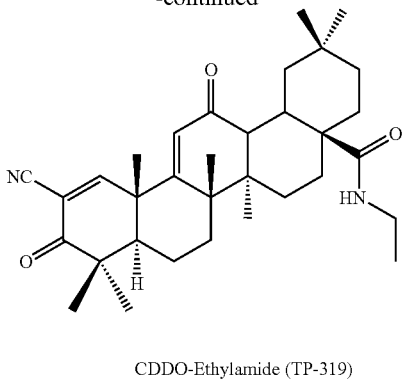

CDDO-Ethylamide (TP-319)

CDDO is the prototype for a large number of compounds in a family of agents that have been shown useful in a variety of contexts, including cancer treatment and chemoprevention. CDDO-Me (TP-155), CDDO-Im (TP-235), and CDDO-Ethylamide (TP-319) are CDDO derivatives that are modified at the C-28 position.

CDDO-Me and CDDO-Im are also reported to possess capacities to modulate transforming growth factor-β (TGF-β)/Smad signaling in several types of cells (Suh et al., 2003; Minns et al., 2004; Mix et al., 2004)

The following formula provides CDDO family compounds that may be used in accordance with the present invention:

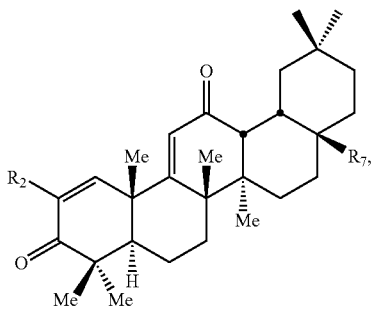

wherein $R_2$, is —H, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-aryl amino, $C_7$-$C_{15}$-aralkylamino, $C_1$-$C_{15}$-heteroaryl amino, $C_2$-$C_{15}$-heteroaralkylamino, or $C_2$-$C_{15}$-amido; $R_7$ is H, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_7$-$C_{15}$-aralkyl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-aryl amino, $C_7$-$C_{15}$-aralkylamino, $C_1$-$C_{15}$-heteroaryl amino, $C_2$-$C_{15}$-heteroaralkylamino, or $C_2$-$C_{15}$-amido; further wherein any ketone group shown in the above structure may replaced by its enol tautomer, and pharmaceutically acceptable salts, and hydrates thereof.

CDDO compounds corresponding to this formula can be prepared according to the methods taught by Honda et al., 2000b and Honda et al., 2002, which are both incorporated herein by reference.

20

B. TBE Compounds

It has been shown that tricyclic-bis-enone compounds (TBEs) with similar enone functionalities in rings A and C also inhibit NO production in mouse macrophages (Favaloro et al., 2002) and RAW cells. In particular, bis-cyano enone (±)-TBE-9 is orally active in a preliminary in vivo inflammation model (Favaloro et al., 2002).

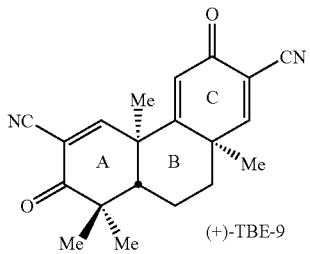

(+)-TBE-9

In addition, is has been found that (+)-TBE-9 having the opposite configuration to that of CDDO shows 10-times higher inhibitory activity than (−)-TBE-9 on NO production in mouse macrophages. To the contrary, (−)-TBE-9 is active against MCF-7 mouse breast cancer cell lines, whilst (+)-TBE-9 is inactive (Honda et al., 2003; U.S. Patent Publication No. US2003/0232786).

Therefore, additional TBE compounds were designed. Initial attention was focused on modifying the C-8a position because insertion of functionalities at C-8a would be expected to improve the potency and pharmacokinetics because the balance between hydrophilicity and hydrophobicity is shifted. Also, water-soluble compounds could be obtained by the insertion of appropriate functionalities. In addition, although some biologically active natural products have functionalities at the same position (e.g., anti-tumor quassinoids (Cassady et al., 1980)), CDDO analogs with functionalities at the same position cannot be synthesized from oleanolic acid. Various C-8a functionalized (including typical electron-withdrawing and releasing groups) TBE compounds were synthesized using the simple tricycles 1a-1c, shown below, as starting materials, whose efficient synthesis has been established in Honda et al., 2005, which is incorporated herein by reference.

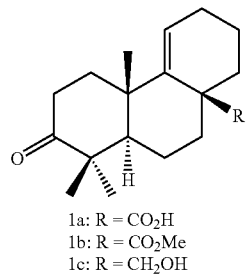

1a: R = $CO_2H$
1b: R = $CO_2Me$
1c: R = $CH_2OH$

The potency of the new TBEs for inhibition of NO production in RAW cells has been evaluated. Among the compounds studied, it was found that (±)-TBE-31, having a C-8a alkyne group is extremely potent at one nanomolar concentrations. The potency is much higher than CDDO and equal to TP-225, which has the highest potency amongst semi-synthetic triterpenoids in the same assay (Honda et al., 2002). In addition, TBE-31 shows extremely high potency in various in vitro and in vivo assays. For example, TBE-31 inhibits proliferation of RMPI 8226 human myeloma cells and U937 human leukemia cells. TBE-31 is a potent inducer of heme oxygenase-1 in U937 cells. TBE-31 is orally active in the in vivo assay of heme oxygenase-1 induction. This potency is much higher than CDDO and equal to CDDO-Im, which has the highest potency amongst semi-synthetic triterpenoids in the same assay (Liby et al., 2005). TBE-31 induces CD11b expression in U937 cells. This potency is much higher than CDDO and CDDO-Im. TBE-31 inhibits iNOS in RAW cells stimulated with interferon-γ.

Given the structural similarities between TBEs and CDDO compounds, especially the presence of the two enone groups, which are believed to function as Michael addition acceptors, the inventors contemplate that the TBEs will promote the growth of bone and/or cartilage. The TBEs, which are described in the present invention, may have the capacity to modulate transforming growth factor-β (TGF-β)/Smad signaling in several types of cells.

i. Synthesis of (±)-TBE-31 and 34 in Racemic Form

Intermediate I is a key intermediate for the synthesis of various TBE-31 analogs. Scheme 1 shows the synthesis of Common Intermediate I.

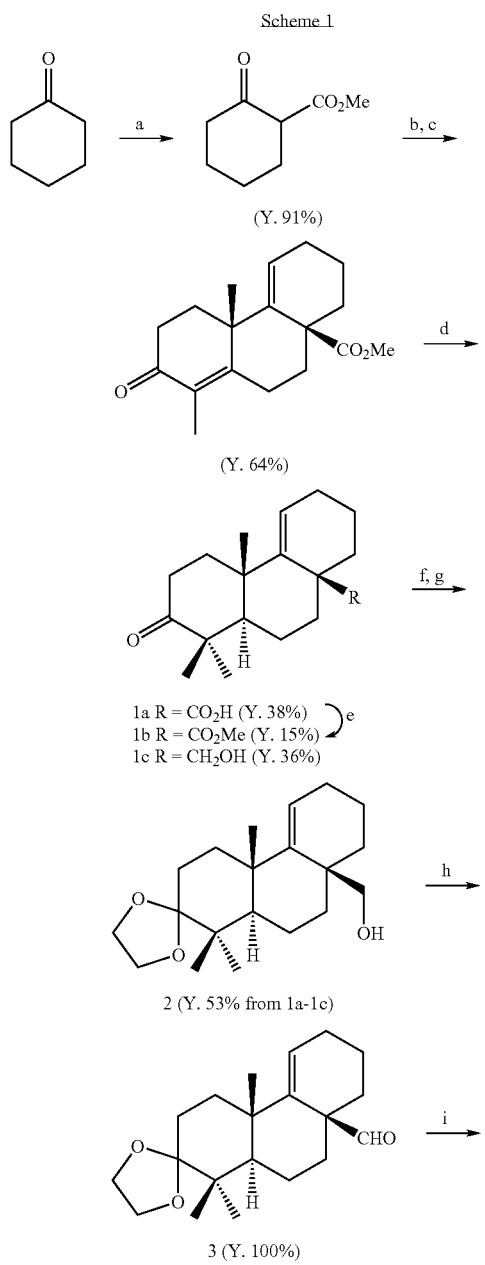

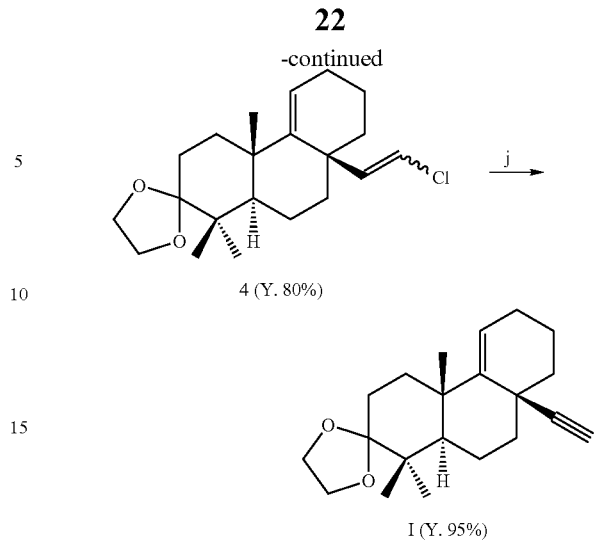

(a) Me₂CO₃, NaH, KH, THF; (b) 3-chloro-2-pentanone, Na, MeOH; (c) Cs₂CO₃, Me₂SO₄, DMF; (d) Li, NH₃, H₂O, CH₃I; (e) CH₂N₂, Et₂O, THF; (f) EG, PPTS, PhH; (g) LAH, Et₂O; (h) Swern oxidation; (i) Ph₃PCH₂Cl₂, n-BuLi, THF, HMPA; (j) MeLi, THF; aq NH₄Cl.

Compounds 1a-1c were obtained from cyclohexanone according to the method of Honda et al. 2005, which is incorporated herein by reference. Without separation, a mixture of 1a-1c was converted to a mixture of 1b and 1c with ethereal diazomethane. Compound 2 was obtained from the mixture of 1b and 1c by protection of their carbonyl groups with ethylene glycol (EG) in the presence of pyridinium p-toluenesulfonate (PPTS) in benzene (PhH) (Sterzycki, 1979), followed by LiAlH₄ reduction (53% yield from the mixture of 1a-1c). Swern oxidation (DMSO and oxalyl chloride, Omura and Swern, 1978) of 2 gave 3 in quantitative yield. Compound 4 was prepared in 80% yield as a mixture of E/Z chlorovinyl isomers by Wittig reaction on 3 with (chloromethyl)triphenylphosphonium chloride (Mella et al., 1988). Dehydrochlorination of 4 with methyl lithium, followed by quenching the acetylide with aqueous NH₄Cl solution afforded the common intermediate I in 95% yield (21% overall yield from cyclohexanone) (Mella et al., 1988). Noteworthy is that 100 g of I can be made from 160 g of cyclohexanone by this sequence.

TBE-31 and 34 in racemic form were synthesized from I by the sequence shown in Scheme 2.

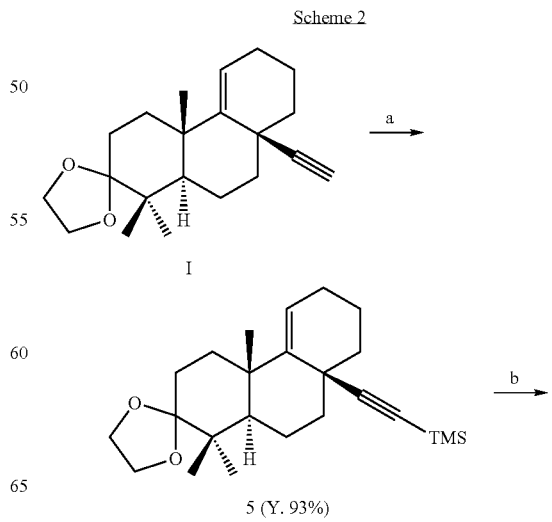

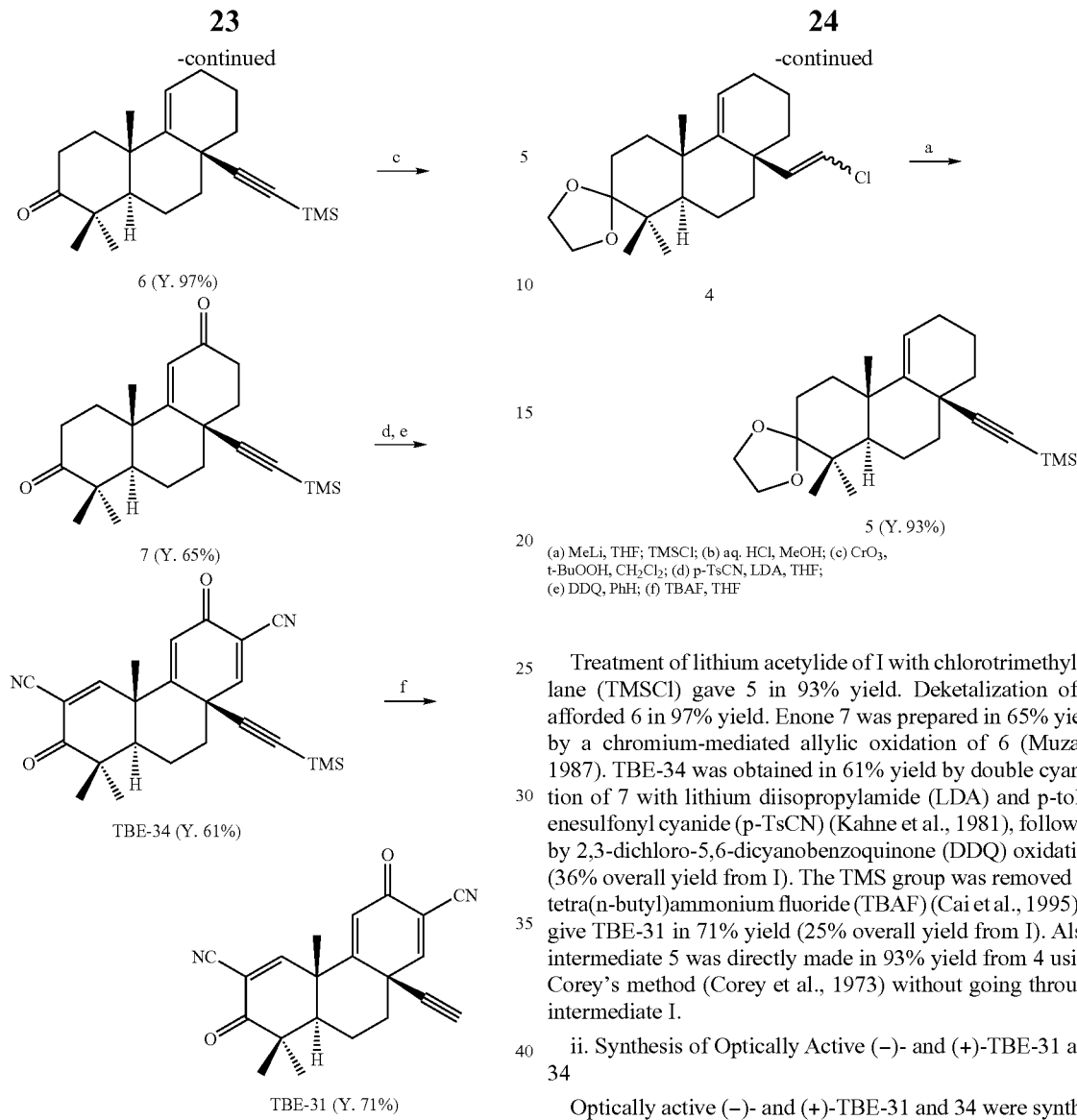

(a) MeLi, THF; TMSCl; (b) aq. HCl, MeOH; (c) CrO₃, t-BuOOH, CH₂Cl₂; (d) p-TsCN, LDA, THF; (e) DDQ, PhH; (f) TBAF, THF

Treatment of lithium acetylide of I with chlorotrimethylsilane (TMSCl) gave 5 in 93% yield. Deketalization of 5 afforded 6 in 97% yield. Enone 7 was prepared in 65% yield by a chromium-mediated allylic oxidation of 6 (Muzart, 1987). TBE-34 was obtained in 61% yield by double cyanation of 7 with lithium diisopropylamide (LDA) and p-toluenesulfonyl cyanide (p-TsCN) (Kahne et al., 1981), followed by 2,3-dichloro-5,6-dicyanobenzoquinone (DDQ) oxidation (36% overall yield from I). The TMS group was removed by tetra(n-butyl)ammonium fluoride (TBAF) (Cai et al., 1995) to give TBE-31 in 71% yield (25% overall yield from I). Also, intermediate 5 was directly made in 93% yield from 4 using Corey's method (Corey et al., 1973) without going through intermediate I.

ii. Synthesis of Optically Active (−)- and (+)-TBE-31 and 34

Optically active (−)- and (+)-TBE-31 and 34 were synthesized by the sequence shown in Scheme 3.

Scheme 3

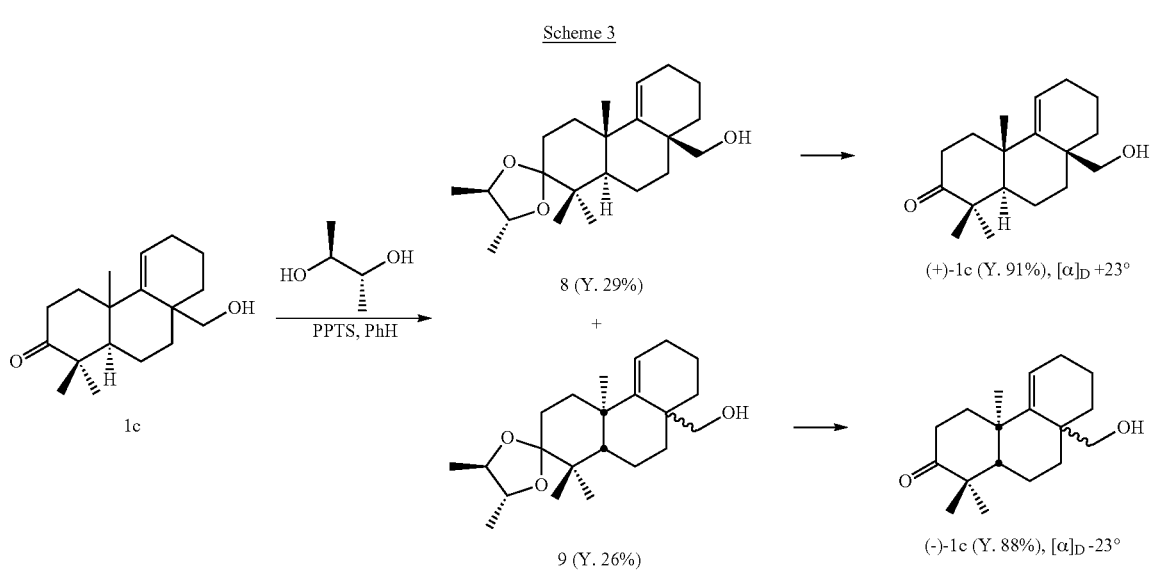

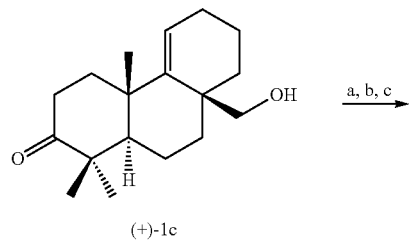

(+)-1c

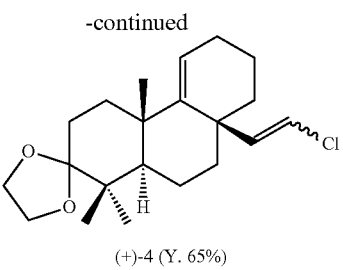

(+)-4 (Y. 65%)

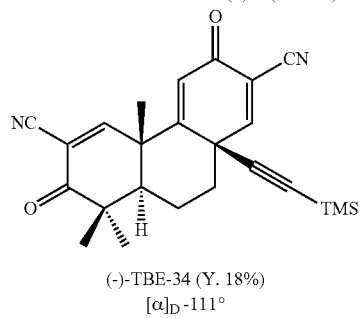

(−)-TBE-34 (Y. 18%)
[α]$_D$ −111°

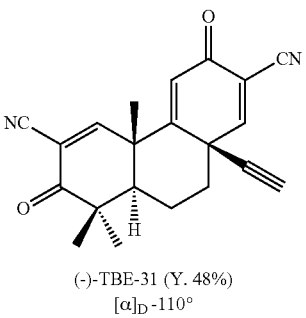

(−)-TBE-31 (Y. 48%)
[α]$_D$ −110°

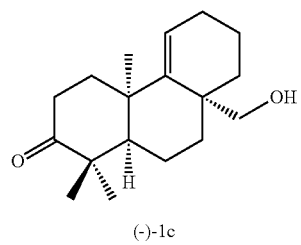

(−)-1c

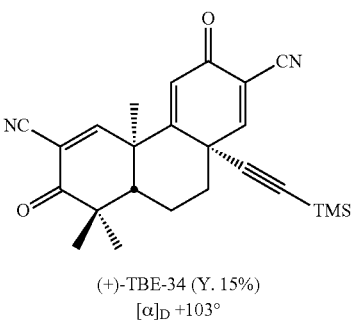

(+)-TBE-34 (Y. 15%)
[α]$_D$ +103°

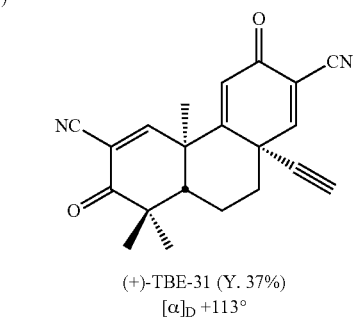

(+)-TBE-31 (Y. 37%)
[α]$_D$ +113°

(a) EG, PPTS, PhH; (b) Swern oxidation; (c) Ph$_3$PCH$_2$Cl$_2$, n-BuLi, THF, HMPA; (d) MeLi, THF; TMSCl; (e) aq. HCl, MeOH; (f) CrO$_3$, t-BuOOH, CH$_2$Cl$_2$; (g) p-TsCN, LDA, THF; (h) DDQ, PhH; (i) TBAF, THF The resolution of alcohol 1c was carried out in the manner described by Grieco (Grieco and Speake, 1998). Treatment of 1c with the chiral diol, (−)-(R,R)-2,3-butanediol afforded the pair of diastereomers 8 and 9. Separation of the two diastereomers was achieved by iterative flash column chromatography to give diastereomer 8 (including 8% of 9) in 29% yield and diastereomer 9 (including 10% of 8) in 26% yield. The diastereomeric purity was determined by $^1$H NMR (300 MHz, CDCl$_3$) using the integration values of the methyl signals (δ 0.92 and 0.88 of 8, and 0.96 and 0.86 of 9) for the two diasteromers.

Diastereomer 8 was then treated with acidic methanol and the resulting ketone (+)-1c was obtained in 91% yield. Similarly, the other diastereomer 9 gave (−)-1c in 88% yield under the same conditions. Based on the diastereomeric purity, we concluded that (+)-1c includes 8% of (−)-1c (enantiomeric excess (ee), 84%) and (−)-1c includes 10% of (+)-1c (ee, 80%). The CD values for the two enantiomers (+)-1c and (−)-1c are Δ$_{288}$=+0.22, and Δ$_{288}$=−0.22 respectively. Based on these CD values and application of the octant rule (Chamey, 1979), we have determined that (+)-1c has the same configuration as that of CDDO and (−)-1c has the opposite configuration.

Enantiomer (+)-1c was treated with ethylene glycol and PPTS to give the protected ketone, which was subjected to Swern oxidation with oxalyl chloride and dimethyl sulfoxide. A Wittig reaction of the resulting aldehyde with (chloromethyl) triphenylphosphonium chloride afforded the alkenyl chloride (+)-4 in 65% yield. Treatment of (+)-4 with methyl lithium and quenching of the resulting anion by TMSCl gave the TMS protected acetylene. Deprotection of the ketal group was followed by a chromium mediated allylic oxidation with t-butyl hydroperoxide which afforded the enone. Double cyanation of the enone with LDA and p-TsCN gave the dinitrile intermediate, which was oxidized by DDQ in benzene to give the desired compound (−)-TBE-34 in 18% yield. Removal of the TMS group was achieved by treatment of (−)-TBE-34 with TBAF to give (−)-TBE-31 in 48% yield.

(+)-TBE-34 was obtained from (−)-1c in 15% yield by the same procedure used to obtain (−)-TBE-34 from (+)-1c.

Removal of the TMS group from (+)-TBE-34 with TBAF afforded the desired (+)-TBE-31 in 37% yield.

iii. Design and Synthesis of New TBE-31 Analogs Using Alkyl Lithium

As shown below, TBE-31 analogs having the structure III, shown below, can be synthesized from compounds having the structure II, also shown below, which is obtained from compound I using alkyl lithium (n-BuLi, MeLi and so on) and $R_1X$ (nucleophilic substitution). TBE-34 (intermediate of TBE-31), TBE-35, 36, 38, and 39 have been prepared in this fashion.

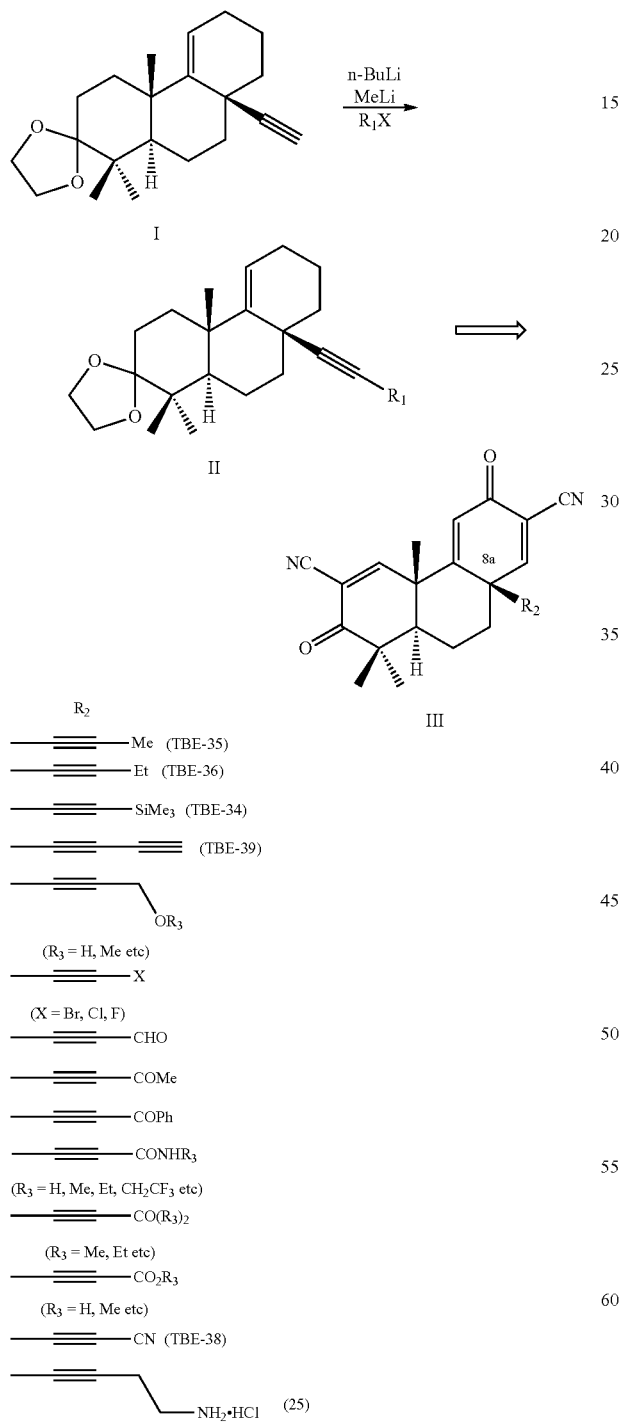

The specific synthetic methods of obtaining TBE-35, 36, 38, and 39 are shown in Schemes 4-7, respectively.

Scheme 4 shows the synthesis of TBE-35 from I.

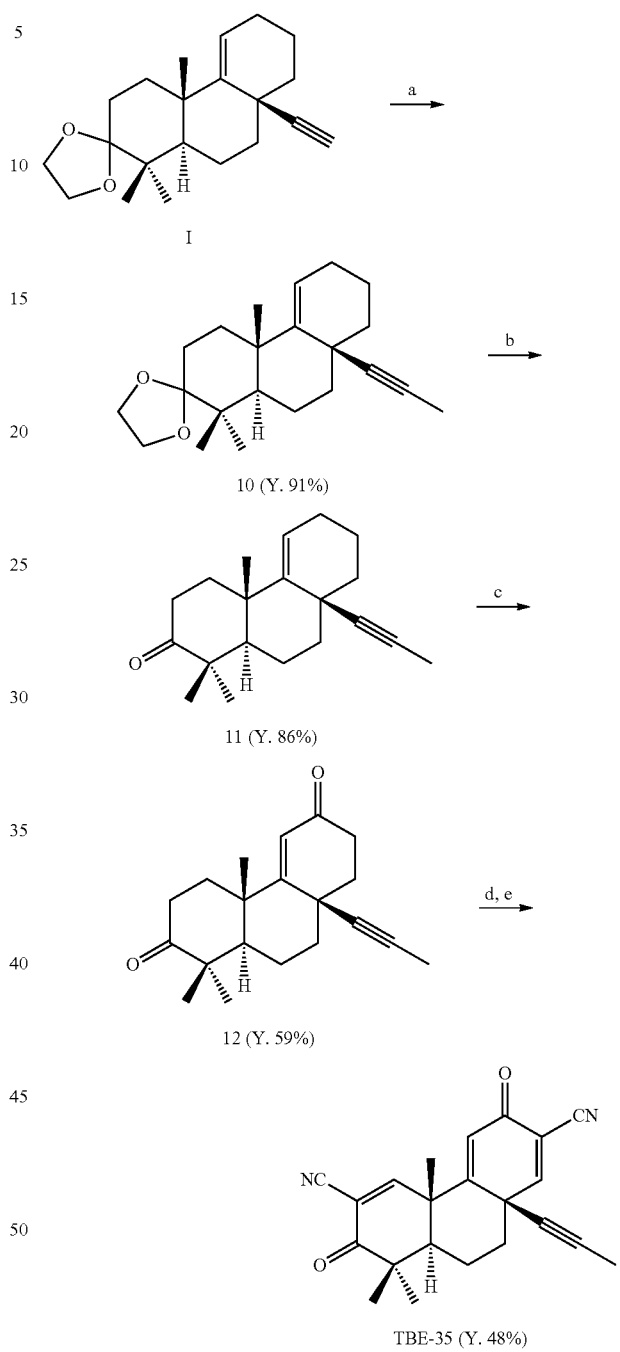

(a) MeLi, THF; MeI; (b) aq. HCl, MeOH; (c) CrO$_3$, t-BuOOH, CH$_2$Cl$_2$; (d) p-TsCN, LDA, THF; (e) DDQ, PhH.

Insertion of the methyl group into the acetylene moiety was achieved by treating the intermediate I with methyl lithium and trapping the resulting anion with methyl iodide, to give 10 in 91% yield. The ketal 10 was subjected to acidic conditions to give the ketone 11 in 86% yield. Allylic oxidation of 11 afforded the enone 12 (59% yield). Double cyanation of 12 with LDA and p-TsCN gave the dinitrile, which was reacted with DDQ in benzene to give the desired compound TBE-35 in 48% (22% overall yield from I).

Scheme 5 shows the synthesis of TBE-36 from I.

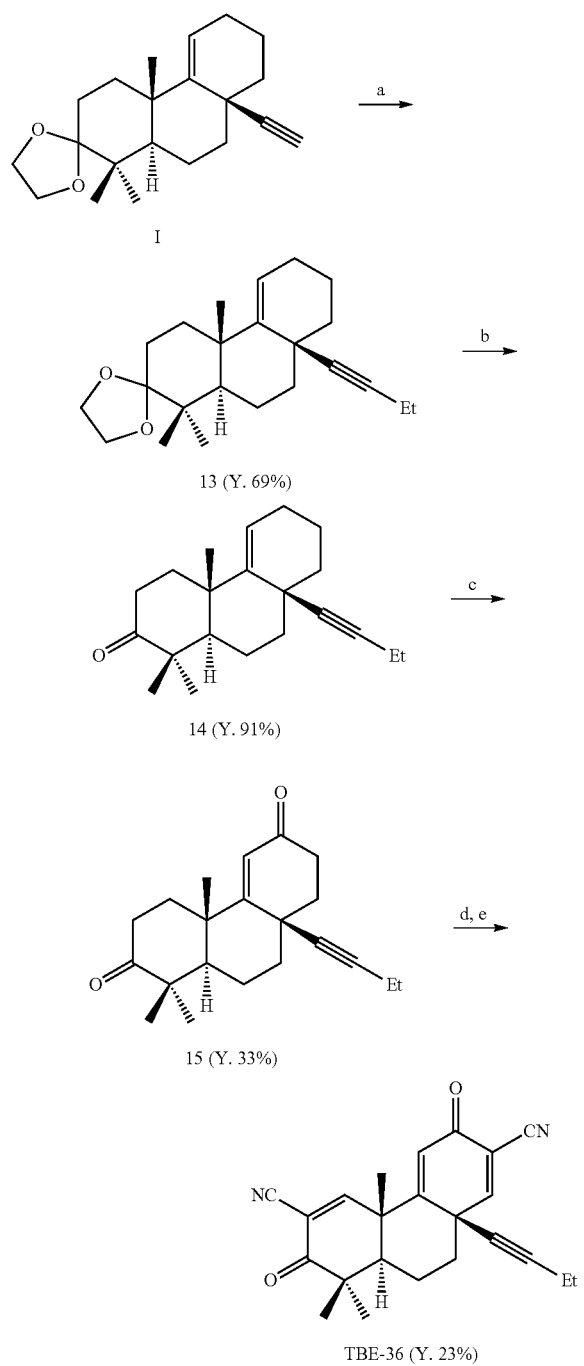

(a) MeLi, THF; EtI; (b) aq. HCl, MeOH; (c) CrO₃, t-BuOOH, CH₂Cl₂; (d) p-TsCN, LDA, THF; (e) DDQ, PhH.

Reaction of compound I with MeLi and iodoethane gave the ethyl acetylene 13 in 69% yield. Compound 13 was treated with aqueous HCl solution to give the ketone 14 in 91% yield. Allylic oxidation of 14 afforded the diketone 15 in 33% yield. Treatment of 15 with LDA and p-TsCN gave the dinitrile intermediate, which was subjected to oxidation by DDQ in benzene to give the desired compound TBE-36 in 23% yield (5% overall yield from I).

Scheme 6 shows the synthesis of TBE-38 from I.

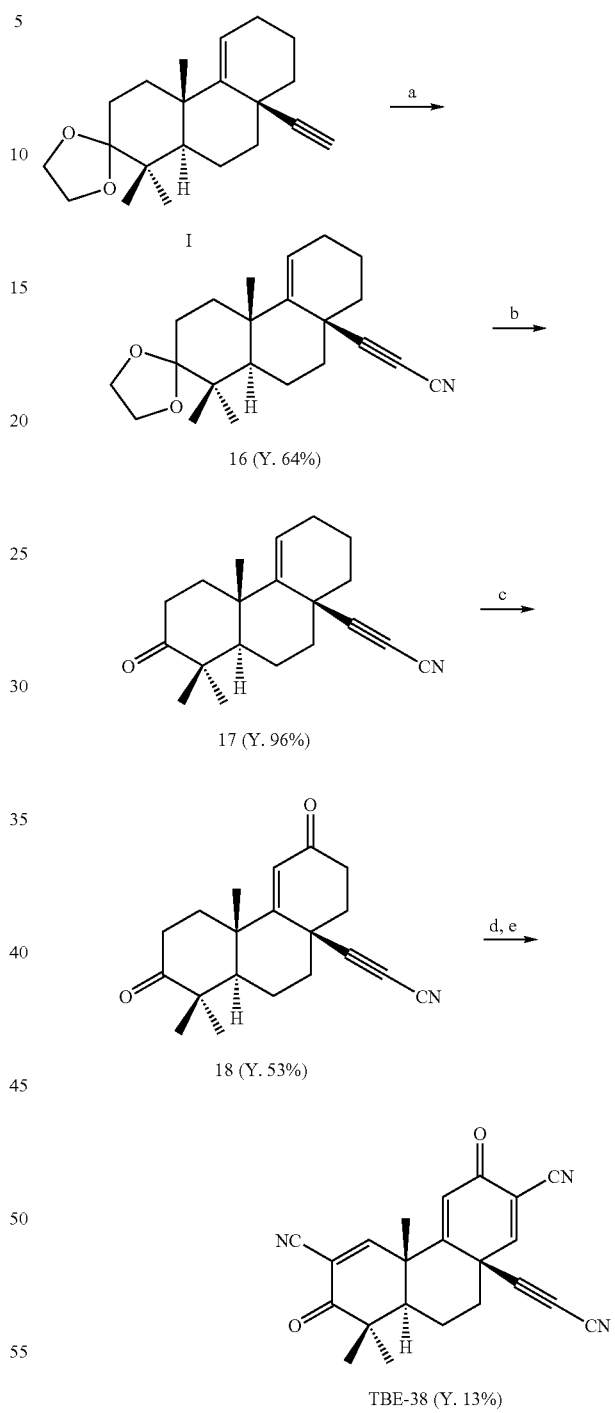

(a) n-BuLi, THF; PhOCN; (b) aq. HCl, MeOH; (c) CrO₃, t-BuOOH, CH₂Cl₂; (d) p-TsCN, LDA, THF; (e) DDQ, PhH.

Treatment of lithium acetylide of I with phenyl cyanate (PhOCN) afforded 16 in 64% yield (Murray et al., 1980). Deketalization of 16 gave 17 in 96% yield. Allylic oxidation of 17 gave 18 in 53% yield. Double cyanation of 18, followed by DDQ oxidation gave TBE-38 in 13% yield (4% overall yield from I).

Scheme 7 shows the synthesis of TBE-39 from I.

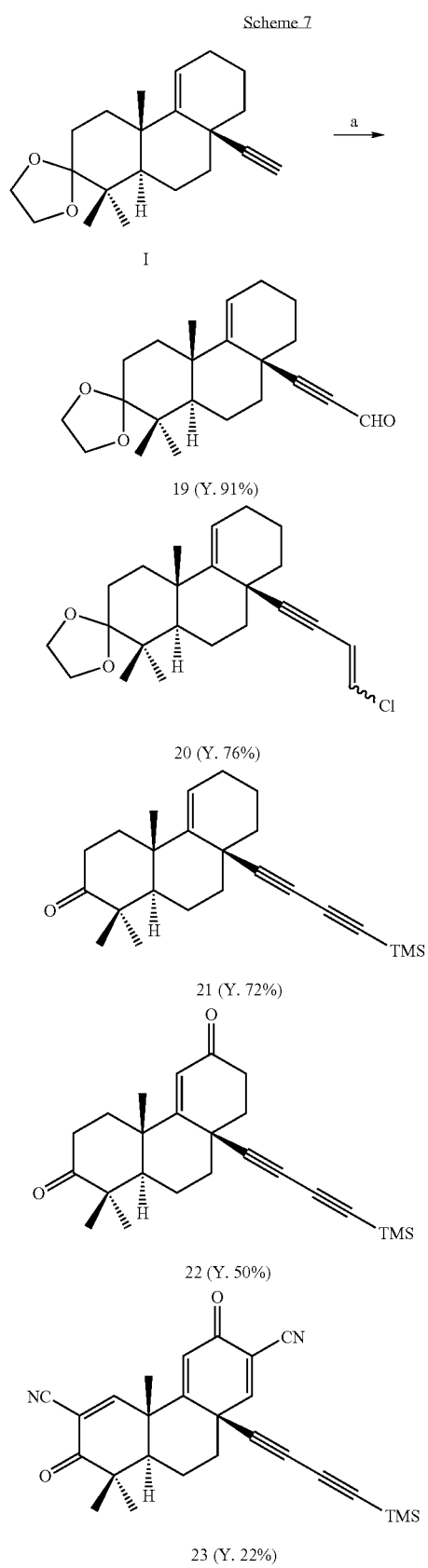

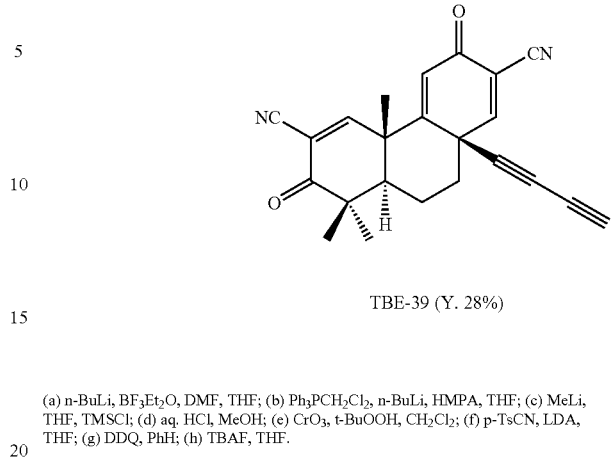

(a) n-BuLi, BF$_3$Et$_2$O, DMF, THF; (b) Ph$_3$PCH$_2$Cl$_2$, n-BuLi, HMPA, THF; (c) MeLi, THF, TMSCl; (d) aq. HCl, MeOH; (e) CrO$_3$, t-BuOOH, CH$_2$Cl$_2$; (f) p-TsCN, LDA, THF; (g) DDQ, PhH; (h) TBAF, THF.

The aldehyde 19 was obtained by the formylation of alkyne I with dimethylformamide and boron triflouride etherate in 91% yield (Iguchi et al, 1993). The Wittig reaction of aldehyde 19 with (chloromethyl) triphenylphosphonium chloride gave the alkenyl chloride 20 in 76% yield. Treatment of 20 with methyl lithium and quenching of the resulting anion with TMSCl yielded the TMS protected alkyne. Treatment of this alkyne with aqueous HCl solution afforded the ketone 21 in 72% yield. Allylic oxidation of 21 gave the enone 22 in 50% yield. Double cyanation of 22 with p-TsCN gave the dinitrile intermediate, which was subsequently oxidized with DDQ to give the bis-enone 23 in 22% yield. Removal of the TMS group with TBAF gave the desired compound TBE-39 in 28% yield (2% overall yield from I).

As an amine hydrochloride, compound 25, shown below, would be water-soluble, making this compound very interesting. The synthetic plan is shown in Scheme 8.

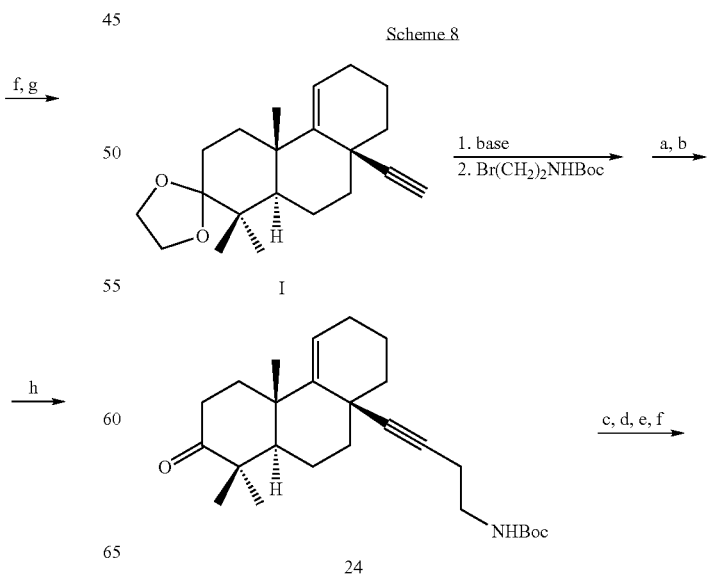

-continued

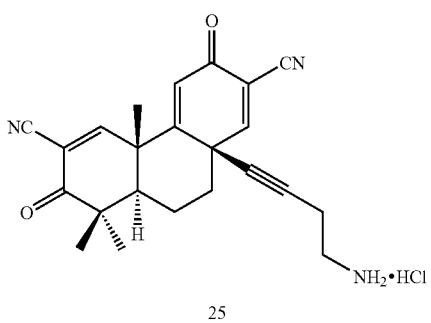

(a) PPTS, acetone; (b) Boc₂O; (c) CrO₃, t-BuOOH, CH₂Cl₂; (d) p-TsCN, LDA, THF; (e) DDQ, PhH; (f) HCl Compound 24 can be synthesized by treatment of acetylide of I with commercially available Br(CH₂)₂NHBoc, followed by deketalization and subsequent protection with Boc₂O. Compound 25 can be obtained from 24 by the same sequence (allylic oxidation, double cyanation, and DDQ oxidation) as for other TBEs, followed by deprotection with HCl.

iv. Design and Synthesis of New TBE-31 Analogs Using Sonogashira Coupling

Sonogashira coupling of acetylene with aryl halide and/or vinyl halide using palladium complex (e.g. PdCl₂(PPh₃)₂) and CuI is a very useful reaction for the synthesis of various acetylene derivatives (Sonogashira et al., 1975). Compounds having structure III can be synthesized by Sonogashira coupling, as shown in Scheme 9. Also, it is possible to synthesize compounds having the structure III, directly from TBE-31. Sonogashira coupling provides a more convergent synthetic approach, allowing for the exploration of various compounds having the structure III.

Scheme 9

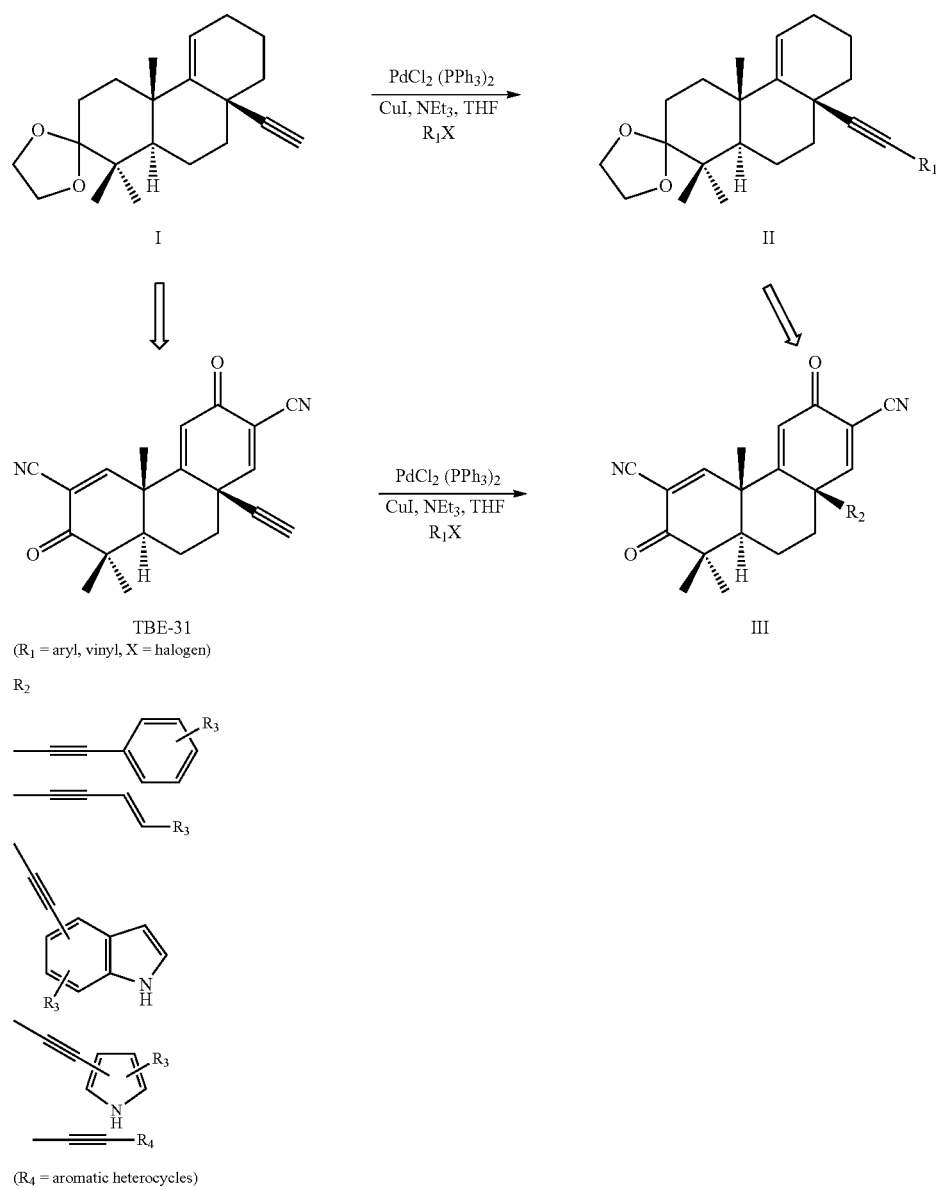

The synthetic plan of compound 29 is shown in Scheme 10. Compound 26 was successfully synthesized in 64% yield from 1 using Sonogashira coupling. Deketalization of 26 can give 27. Allylic oxidation of 27 can afford enone 28. Double cyanation of 28, followed by DDQ oxidation can give compound 29.

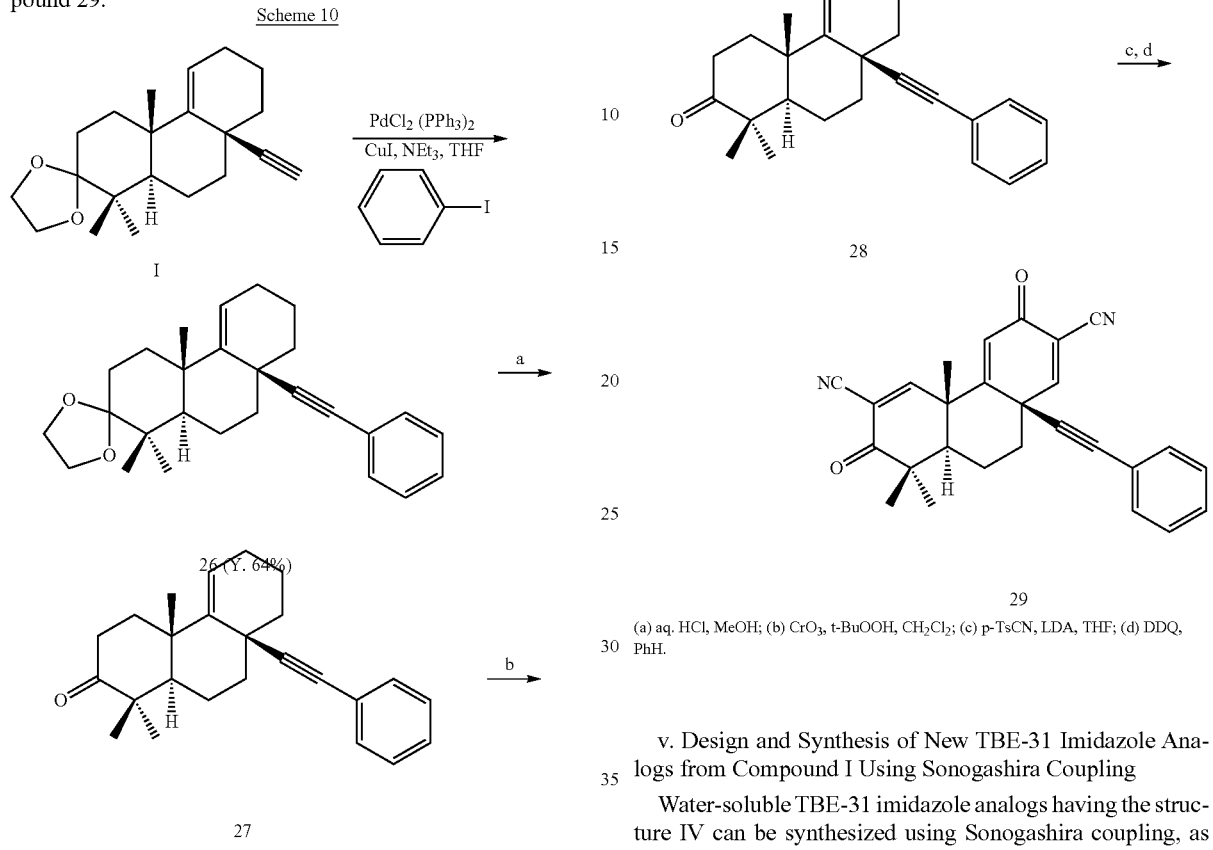

(a) aq. HCl, MeOH; (b) CrO₃, t-BuOOH, CH₂Cl₂; (c) p-TsCN, LDA, THF; (d) DDQ, PhH.

v. Design and Synthesis of New TBE-31 Imidazole Analogs from Compound I Using Sonogashira Coupling Water-soluble TBE-31 imidazole analogs having the structure IV can be synthesized using Sonogashira coupling, as shown in Scheme 11.

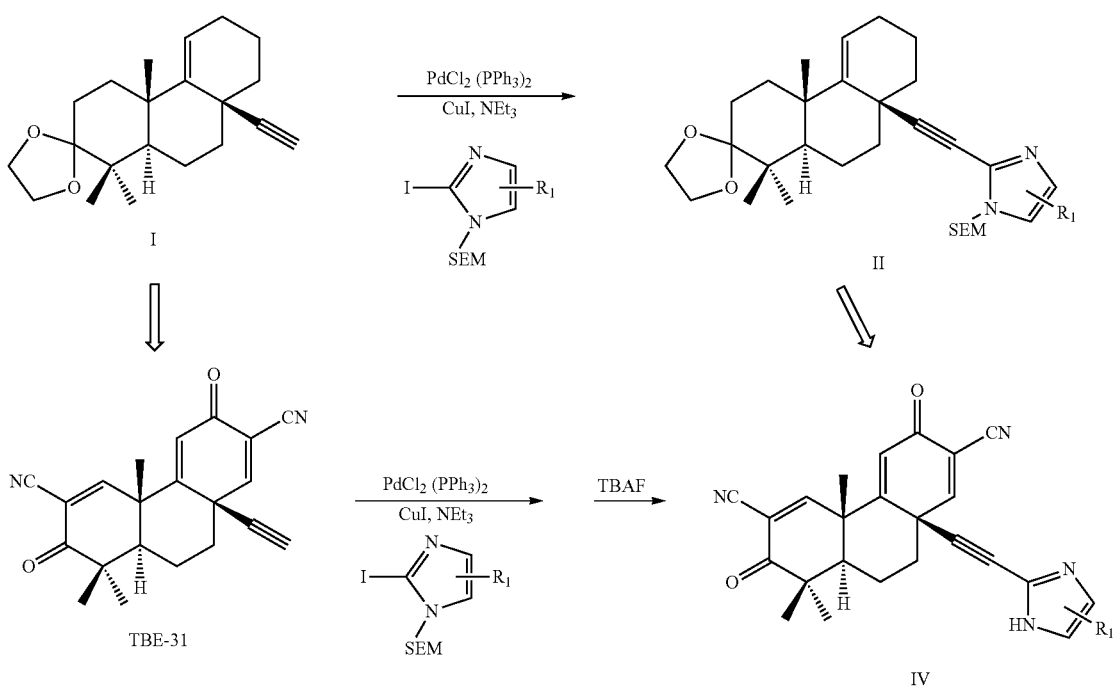

The synthetic plan of compound 34 is shown in Scheme 12. Imidazole hydrochloride 34 is expected to be water-soluble. Compounds 30 was synthesized in 73% yield from I by Sonogashira coupling using iodo-SEM-imidazole (Paul et al. 2002). Deketalization of 30 gave 31 in 70% yield. Allylic oxidation of 31 can give 32. Double cyanation of 32, followed by DDQ oxidation can afford 33. The desired compound 34 can be obtained by removal of SEM group of 33.

Scheme 12

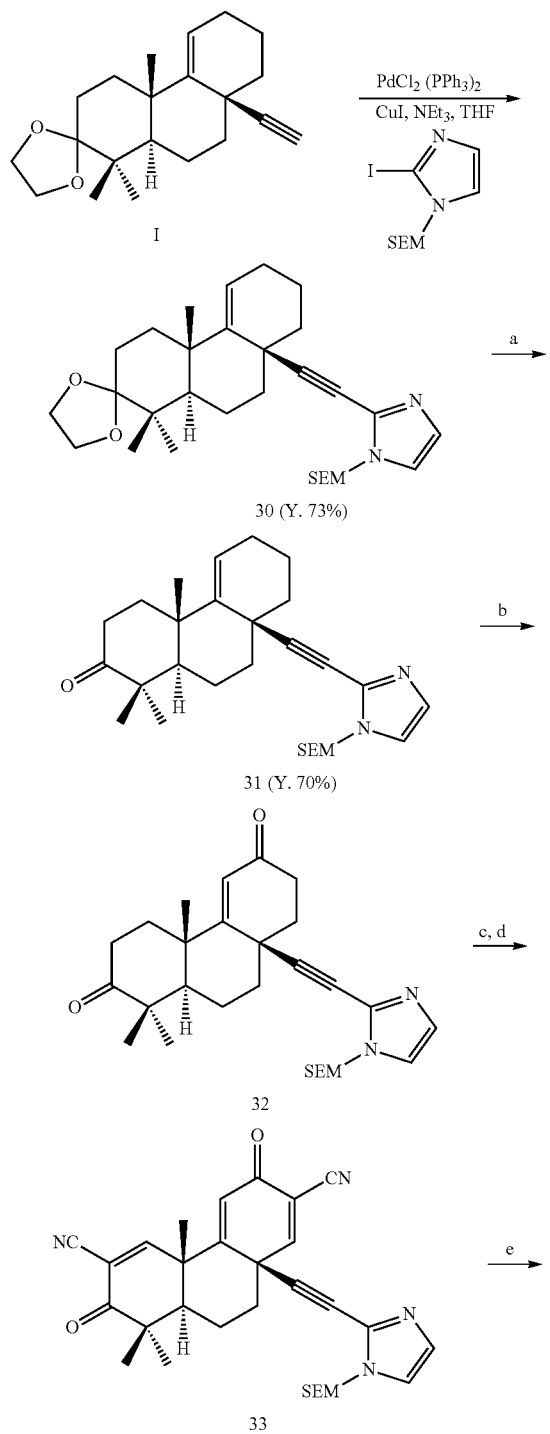

-continued

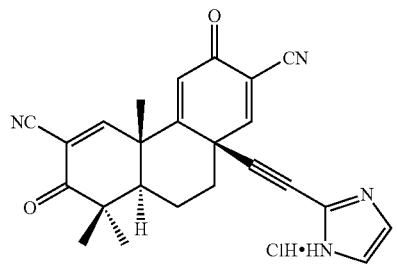

34

(a) aq. HCl, MeOH; (b) CrO₃, t-BuOOH, CH₂Cl₂; (c) p-TsCN, LDA, THF; (d) DDQ, PhH; (e) TBAF, THF.

vi. Design and Synthesis of New TBE-31 Analogs from Compound I Using Mannich Reactions Water-soluble TBE-31 analogs with amino side chains (38, 42, and so on) can be synthesized using Mannich reactions. Analogs 38 and 42 can be synthesized by the sequence shown in Schemes 13 and 14.

Scheme 13

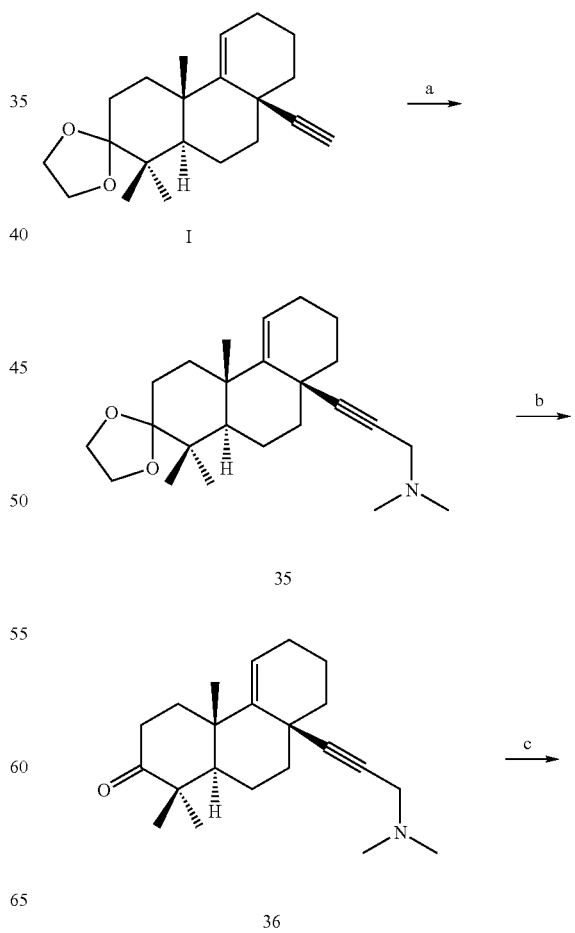

39
-continued

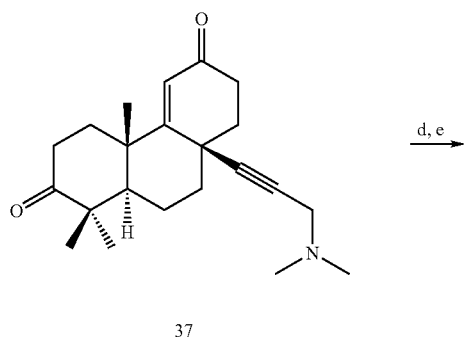

37

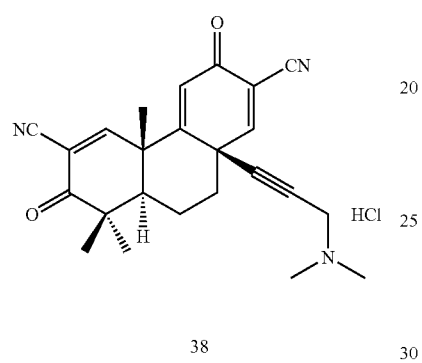

38

(a) (Me$_2$N)$_2$CH$_2$, CuCl, THF; (b) aq. HCl, MeOH; (c) CrO$_3$, t-BuOOH, CH$_2$Cl$_2$; (d) p-TsCN, LDA, THF; (e) DDQ, PhH; HCl, dioxane.

The Mannich reaction of I with bis(dimethylamino)methane (Amstutz et al., 1987; Chung et al., 1990) under the catalysis of CuCl in refluxing THF can afford 35. Compound 38 can be obtained from 35 by the same sequence as for other TBEs.

Scheme 14

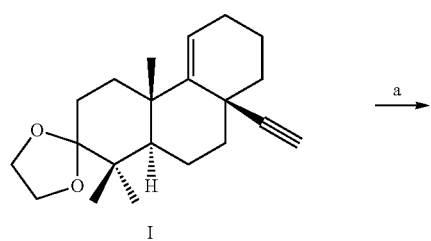

I

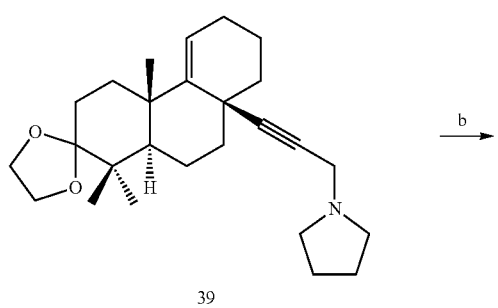

39

40
-continued

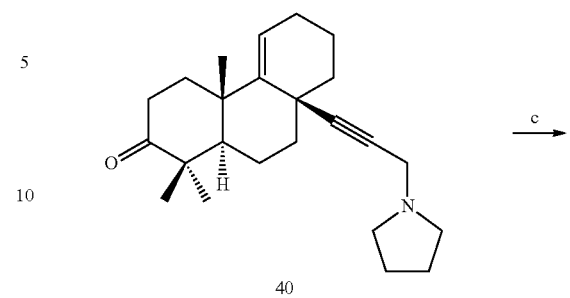

40

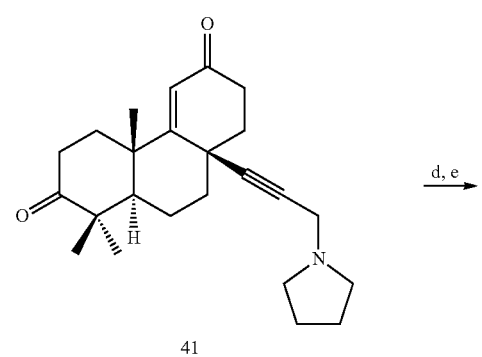

41

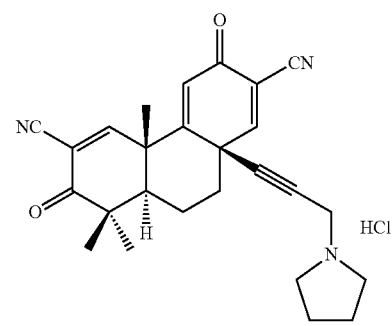

42

(a) HCHO, pyrrolidine, CuCl, THF; (b) aq. HCl, MeOH; (c) CrO$_3$, t-BuOOH, CH$_2$Cl$_2$; (d) p-TsCN, LDA, THF; (e) DDQ, PhH; HCl, dioxane.

Compound 39 can be synthesized by the Mannich reaction using formaldehyde and pyrrolidine under the catalysis of CuCl. Compound 42 can be obtained from 39 by the same sequence as for other TBEs.

vii. Design and Synthesis of New TBE-31 Analogs with a Carboxyl Group in Ring A

Compound 48 can be synthesized by the sequence shown in Scheme 15.

Scheme 15

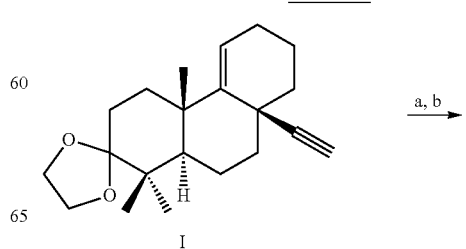

I

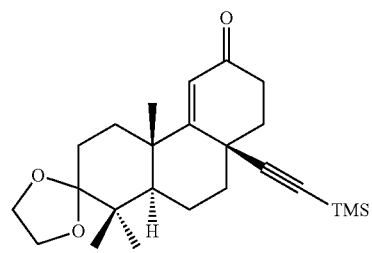

43

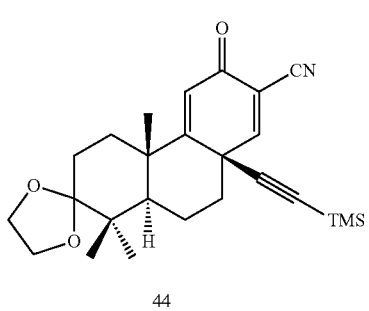

44

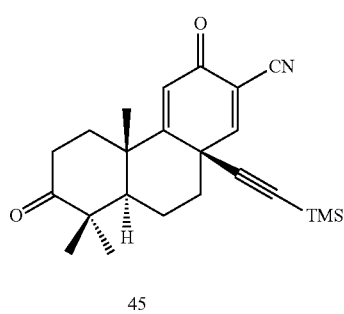

45

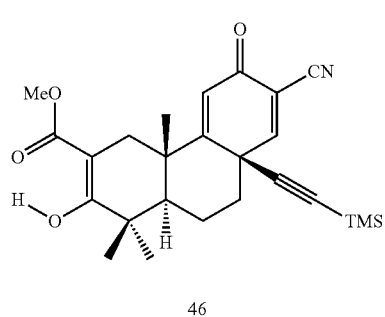

46

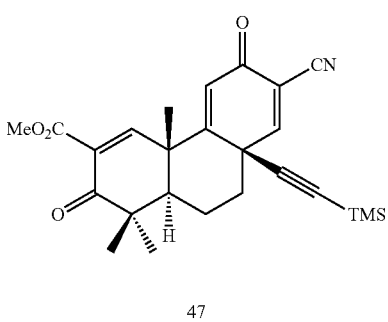

47

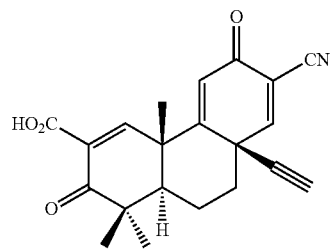

48

(a) MeLi, LDA, THF; TMSCl; (b) CrO₃, t-BuOOH, CH₂Cl₂; (c) p-TsCN, LDA, THF; (d) DDQ, PhH; (e) PPTS, acetone; (f) Stiles' reagent, DMF; (g) CH₂N₂; (h) PhSeCl, pyr., H₂O₂; (i) K₂CO₃.

Compound 43 can be synthesized by treatment of acetylide of I with TMSCl, followed by allylic oxidation. Cyanation of 43, followed by DDQ oxidation can afford 44. After removal of ketal of 44, 46 can be obtained from 45 by Stiles' reagent (Finkbeiner et al., 1963), followed by methylation. Addition of phenylselenyl chloride (PhSeCl), followed by oxidation/elimination with H₂O₂ can give 47 (Liotta et al., 1981). The desired compound 48 can be prepared by treatment of 47 with K₂CO₃-MeOH-water (Cai et al., 1995).

viii. Design and Synthesis of New TBE-31 Analogs Containing Amino Side Chains from Compound I A series of analogs with a C-8a alkyne group and C-7 amino side chains having general formula V (Scheme 16) was designed for the following reasons. In many cases, amine side chains like pyrrolidine, piperidine, imidazole etc. affect biological properties, e.g., potency and pharmacokinetics of the parent compounds. Also, salts of these amines would be soluble in water. Thirdly, because one Michael acceptor is diminished in these analogs in comparison with TBE-31 analogs, side effects and/or toxicity, which might be caused by Michael acceptors, may be reduced. They can be synthesized from TBE-37 by Mannich reactions with amines and formaldehyde under basic or acidic conditions. TBE-37 was synthesized from I. Compound 49 was obtained in 76% yield from I by deketalization, followed by formylation with ethyl formate in the presence of sodium methoxide in benzene (Clinton et al., 1961). Treatment of 49 with hydroxylamine (Johnson et al., 1945), followed by allylic oxidation gave 50 in 46% yield. TBE-37 was prepared by cleavage of the isoxazole of 50 with sodium methoxide (Johnson et al., 1945), followed by DDQ oxidation (12% overall yield from I).

Scheme 16

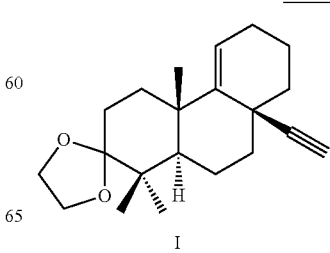

I

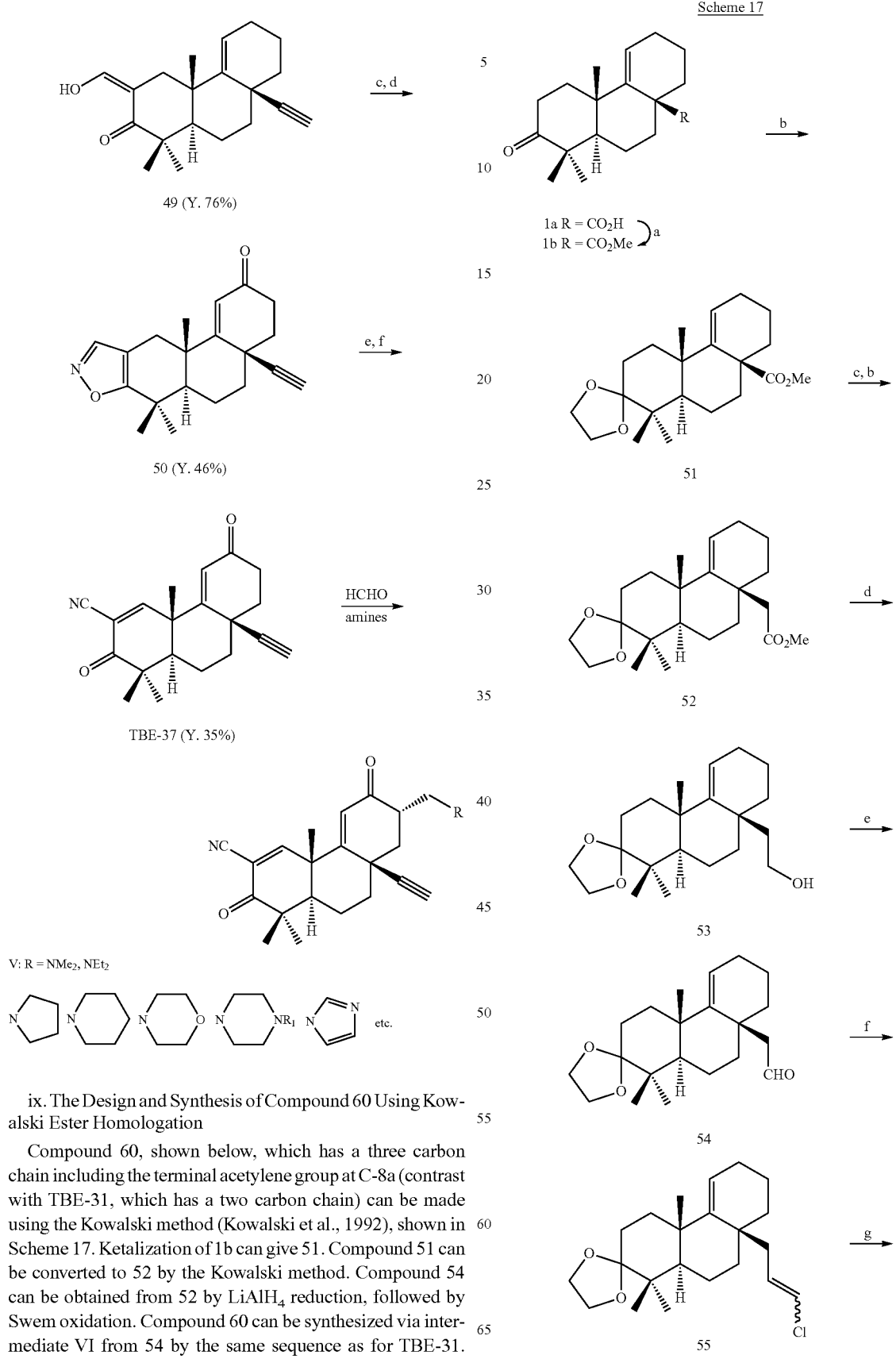

ix. The Design and Synthesis of Compound 60 Using Kowalski Ester Homologation

Compound 60, shown below, which has a three carbon chain including the terminal acetylene group at C-8a (contrast with TBE-31, which has a two carbon chain) can be made using the Kowalski method (Kowalski et al., 1992), shown in Scheme 17. Ketalization of 1b can give 51. Compound 51 can be converted to 52 by the Kowalski method. Compound 54 can be obtained from 52 by LiAlH$_4$ reduction, followed by Swern oxidation. Compound 60 can be synthesized via intermediate VI from 54 by the same sequence as for TBE-31. Intermediate VI is a key intermediate as well as I.

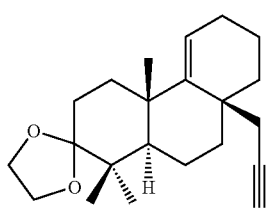

VI

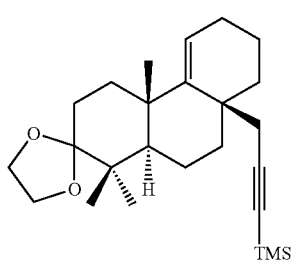

56

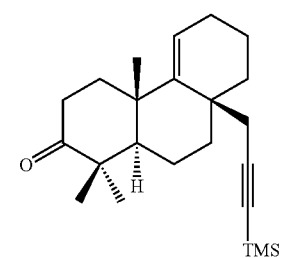

57

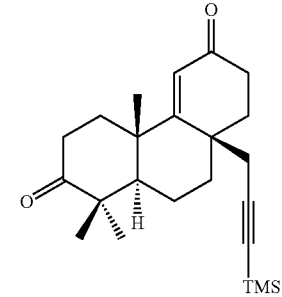

58

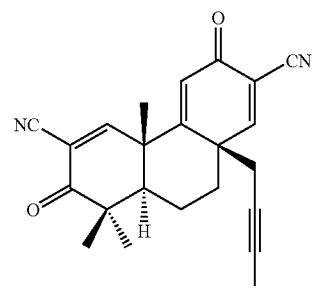

59

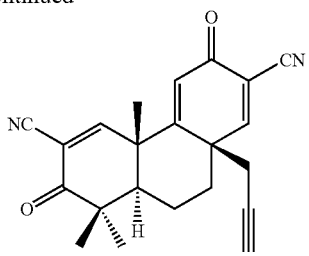

60

(a) CH$_2$N$_2$, Et$_2$O, THF; (b) ethylene glycol, PPTS, PhH; (c) CH$_2$Br$_2$, LiTMP; LiHMDS; s-BuLi, n-BuLi; MeOH, HCl (Kowalski method); (d) LAH, Et$_2$O; (e) Swern oxidation; (f) Ph$_3$PCH$_2$Cl$_2$, n-BuLi, THF, HMPA; (g) MeLi, THF; aq NH$_4$Cl; (h) MeLi; THF; TMSCl; (i) aq. HCl, MeOH; (j) CrO$_3$, t-BuOOH, CH$_2$Cl; (k) p-TsCN, LDA, THF; (l) DDQ, PhH; (m) TBAF, THF Various analogs of compound VII can be prepared from compound VI using the same procedure as used for TBE-31 analogs (Scheme 18). Also, if one were to repeat the Kowalski method for 51, one can synthesize analogs shown in general formula VIII.

Scheme 18

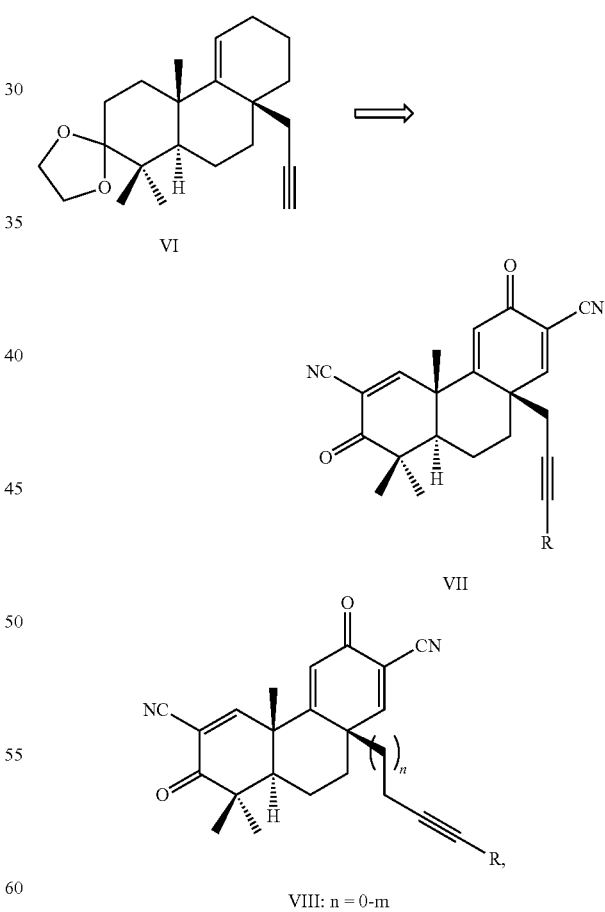

IV. Bone- and Cartilage forming Cells

The present invention describes methods for the ex vivo and in vivo formation of bone and cartilage using from osteogenic cells, chondrocytes, bone and cartilage precursor cells, as well as cell lines derived therefrom. The following section describes various sources for these cells, their isolation and characterization. Osteogenic or bone precursor cells are derived from primary sources such as bone marrow or bone. In addition, cells can be derived from several different species, including cells of human, bovine, equine, canine, feline and murine origin. Articular chondrocytes can generally be derived from humans according to the method taught by Hidvegi et al., 2006, which is incorporated herein by reference.

A. Bone Precursor Cells

Human bone precursor cells are characterized as small-sized cells that express low amounts of bone proteins (osteocalcin, osteonectin, and alkaline phosphatase) and have a low degree of internal complexity (Long et al., 1995). When stimulated to differentiate, these preosteoblast-like cells become osteoblast-like in their appearance, size, antigenic expression, and internal structure. Although these cells are normally present at very low frequencies in bone marrow, a process for isolating these cells has been described (Long et al., 1995). U.S. Pat. No. 5,972,703 further describes methods of isolating and using bone precursor cells, and is specifically incorporated herein by reference.

An example of a technique for isolating bone precursor cells involves the following steps. Mononuclear cells are prepared from bone marrow by separation on ficoll or other suitable equilibrium density separation techniques known to those of skill in the art. Low-density mononuclear cells are then cultured overnight culture to remove plastic-adherent cells. An enrichment step using immuno-affinity isolation involves collection of non-adherent low-density cells using anti-osteonectin (ON) and anti-osteocalcin (OC) antibodies immobilized on plastic as described (Long et al., 1995). The immune adherent cells were collected by trypsinization. Alternative enrichment steps may involve immuno-column chromatography or fluorescence-activated cell sorting. In addition to antibodies to osteonectin and osteocalcin, antibodies to alkaline phosphatase or other cell surface markers expressed on bone precursor cells can be utilized. These are described in greater detail in a following section.

As used herein, a bone precursor cell is any cell that is capable of differentiating or expanding into an osteoblast cell. A bone precursor cell of the present invention is not hematopoietic and thus does not express the pan-hematopoietic antigen CD34. Preferred bone precursor cells include osteoprogenitor cells and preosteoblast cells.

Bone precursor cells can be further enriched by equilibrium-density centrifugation of bone marrow cells. Equilibrium-density centrifugation of bone marrow cells provides low density bone marrow cells enriched in bone precursor cells. In one embodiment, equilibrium-density centrifugation can be performed before the antibody purification. In a second embodiment, equilibrium-density centrifugation can be performed after the antibody purification. Alternatively, the equilibrium-density centrifugation purification step can be performed twice: before and after the antibody purification step.

In another aspect, the population of bone precursor cells can be enriched by removing stromal cells present in bone marrow cells. Removal of stromal cells can be accomplished by exposing bone marrow cells to an adherent surface, typically tissue culture plastic or glass. Stromal cells adhere to tissue culture plastic or glass while bone precursor cells do not. Stromal cells can be removed before or after the immune purification step. Preferably, stromal cells are removed prior to the immune purification step. The use of solid surfaces such as tissue culture plastic or glass is well known in the art. Tissue culture plastic and glass can be treated (e.g., silicone, nitrocellulose, nickel, etc.) to promote or inhibit cell adhesion. Treated and untreated surfaces are available commercially.

In another aspect, an enriched population of bone precursor cells is further fractionated according to size. In a preferred embodiment, size fractionation can be accomplished by fluorescence activated flow cytometry. Bone precursor cells of the present invention have average diameters of between about 8 microns and about 70 microns. Preferably, bone precursor cells have average diameters of between about 10 microns and about 20 microns.

B. Primary Human Osteoblasts

Another source of bone cells for use in the present invention are primary osteoblasts. An example of an isolation procedure for these cells can be found in Robey and Termaine (1985). Briefly, bone chips are obtained during orthopedic surgery. These are treated with Collagenase D for 2 hrs at 37° C., the non-adherent cells washed off, the bone pieces minced, and cultured in $Ca^{2+}$-free media containing 10% FCS and Pen/Strep. After the cultures are confluent, the cells are collected by trypsinization and cultured in $Ca^{2+}$-containing DMEM for 2-3 weeks. Bone-derived osteoblasts are recovered by trypsinization.

Alternative methods for isolating osteoblasts from bone are known in the art (see, for example, Aubin et al., 1982). As reported, the calvaria is excised, rinsed in a medium and minced with scissors. The minced bone is digested with collagenase for a short period of time in medium. The cells are removed by centrifugation and decanting the supernatant, leaving the bone pieces behind. Fetal calf serum is added to inhibit the collagenase digestion. Cells are plated at a low density in an appropriate growth medium, and clonal cell colonies are cultured in replicate for continuous culture and characterization.

C. Bone Cell Lines

In addition to primary osteoblasts and bone precursor cells as described above, various cell lines can be used as a starting point for ex vivo bone spheroid formation as described by the methods in the present invention. Cell lines can be from a number of species, including human, bovine, equine, canine, feline and murine origin. Exemplary cell lines as described in the examples included in this invention are MG-63 cells (ATCC #CRL-1427), C3/H10T1/2 cells (ATCC # CCL-226) and SAOS-2 cells (ATCC # HTB-85). Other cell lines, also available through the American Type Culture Collection, include HOS cells (ATCC# CRL-1543) and various derivatives thereof, G-292 (ATCC# CRL-1423), SJSA-1 cells (ATCC# CRL-2098), Hs 3.T cells (ATCC# CRL-7005), TE 415.T cells (ATCC# CRL-7764), TE 418.T cells (ATCC# CRL-7766), Hs 755(A).T cells (ATCC# CRL-7877), 143B cells (ATCC# CRL-8303), U-2 OS cells (ATCC# HTB-96) and T1-73 cells (ATCC# CRL-7943). These cell lines are all derived from human osteosarcomas. Similar osteosarcoma cell lines from several other species are available from ATCC.

D. Chondrocytes

Chondrocytes are the only cells found in cartilage. They produce and maintain the cartilagenous matrix. From least- to terminally-differentiated, the chondrocytic lineage is (a) colony-forming unit-fibroblast (CFU-F), (b) mesenchymal stem cell/marrow stromal cell (MSC), (c) chondrocyte, an (d) hypertrophic chondrocyte. When referring to bone or cartilage, mesenchymal stem cells (MSC) are commonly known as osteochondrogenic (or osteogenic, chondrogenic, osteoprogenitor, etc.) cells since a single MSC has shown the ability to differentiate into chondrocytes or osteoblasts, depending on the medium. In vivo, differentiation of a MSC in a vascularized area (such as bone) yields an osteoblasts, whereas differentiation of a MSC in a non-vascularized area (such as cartilage) yields a chondrocyte. Chondrocytes undergo terminal differentiation when they become hypertrophic during endochondral ossification. This last stage is characterized by major phenotypic changes in the cell. Although chondroblast is still commonly used to describe an immature chondrocyte, use of the term is discouraged, for it is technically inaccurate, since the progenitor of chondrocytes (which are mesenchymal stem cells) can also differentiate into osteoblasts.

V. Cellular Markers

A. Bone Cells and Precursors

Various cellular markers are used to define and/or purify osteogenic precursor cells for use in the present invention. Bone precursor cells, such as those described in U.S. Pat. No. 5,972,703, herein incorporated in its entirety by reference, are immunoreactive with bone precursor cell antibody. A bone precursor cell antibody is used to enrich the population of bone precursor cells. Bone precursor cell antibodies include anti-osteocalcin, anti-osteonectin, and anti-bone alkaline phosphatase. Anti-osteocalcin, anti-osteonectin, and anti-bone alkaline phosphatase were described in Shull et al. (1984). As bone precursor cells are further characterized, other antibodies which immunoreact with a bone precursor cell may be generated by one of ordinary skill in the art. The use of these other antibodies immunoreactive with a bone precursor cell are contemplated as well. In a particular embodiment, a bone precursor cell antibody is conjugated to a solid substrate. The solid substrate is preferably a tissue culture or petri dish. The use of solid surfaces such as tissue culture plastic or glass is well known in the art. Tissue culture plastic and glass can be treated (e.g., silicone, nitrocellulose, nickel, etc.) to promote or inhibit protein adhesion. Treated and untreated surfaces are available commercially. Antibody coated tissue culture dishes can be utilized to "pan" for bone precursor cells. Briefly, bone marrow cells containing bone precursor cells are incubated on antibody coated dishes. Bone precursor cells adhere to the antibodies while all other cells do not adhere to the dish. After incubation, the dish non-adherent cells are removed by gently washing the dish with media. Bone precursor cells were removed from the dish and further analyzed, purified or differentiated into osteoblasts.

In another embodiment, a second antibody immunoreactive with a bone precursor cell antibody can be used to enrich the population of bone precursor cells. The use of a secondary antibody is generally known in the art. Typically, secondary antibodies are antibodies immunoreactive with the constant regions of the first antibody. Preferred secondary antibodies include anti-rabbit, anti-mouse, anti-rat, anti-goat, and anti-horse and are available commercially. In a preferred embodiment, secondary antibodies are conjugated to a solid substrate including tissue culture dish, agarose, polyacrylamide, and magnetic particles. In this embodiment, a bone precursor cell antibody is first immunoreacted to a bone precursor cell. The bone precursor cell with the attached antibody is next exposed to the secondary antibody that is conjugated to a solid substrate. Enrichment of precursor cells is achieved because only cells that present a bone precursor cell antibody immunoreact with the secondary antibody. A commercially available kit provides secondary antibodies conjugated to magnetic particles. In this system, bone precursor cells that present a bone precursor cell antibody are purified by exposure to a magnetic field.

The preparation of bone antibodies (i.e., to osteonectin, osteocalcin and alkaline phosphatase) was reported in Shull et al., 1989, incorporated herein by reference. Both polyclonal and monoclonal antibodies are contemplated by the present invention. Means for preparing and characterizing antibodies are well known in the art (see, e.g., Harlow and Lane, 1988).

Cell surface antigens on normal cells of the osteogenic lineage have been reported for avian and rodent species (Bruder and Caplan, 1989; 1990; Turksen et al., 1992). Some of these antibodies reported also react with cells other than those found in bone. Monoclonal antibodies have been raised against intracellular antigens in normal human osteoblasts and against the surface of transformed human osteogenic cell lines (Embleton et al., 1981; Hosoi et al., 1982; Heiner et al., 1987; Bruland et al., 1988; Tsai et al., 1990; Walsh et al., 1994). Examples of osteogenic cell markers, production of antibodies and hybridomas, as well as methods of using these markers are described in U.S. Pat. No. 5,643,736. An example of a monoclonal antibody against a cell surface epitope capable of identifying human osteogenic cells is one directed against alkaline phosphatase (Lawson et al., 1985). This well-characterized cell surface enzyme has served as the historical standard for identifying a large family of osteogenic cells, and is readily demonstrated by a simple histochemical stain.

Other preferred antigens include osteocalcin and osteonectin. Osteocalcin is a vitamin K-dependent bone calcium binding protein also called bone gla protein (BGP). Particularly, human osteocalcin is a relatively small protein composed of 49 amino acids and having a molecular weight of 5800. This protein is produced from osteoblast, and occupies about 20% of the constituent components of non-collagen protein of the bones. This protein contains gamma-carboxyglutamic acid residues and has a strong affinity for hydroxyapatite, and it is therefore presumed to have an important role in the formation of the bone matrices. Osteonectin, also termed BM40 or SPARC (secreted protein, acidic and rich in cysteine) is a multifunctional glycoprotein involved in tissue mineralization, cell-extracellular matrix interactions as well as angiogenesis. Non-collagenous, calcium-binding glycoprotein of developing bone. It links collagen to mineral in the bone matrix.

The monoclonal antibodies against precursor cells can be labeled with suitable radioactive, enzymatic, fluorescent or other labels by conventional methods and/or bound to suitable solid carriers, which will be apparent to those skilled in the art. For example, monoclonal antibodies can be used in combination with, or coupled to, an immunochemical such as fluorescein isothiocyanate, peroxidase, biotin and its analogs (e.g., iminobiotin), avidin and its analogs (streptavidin), or other such markers. Moreover, monoclonal antibodies can be bound or attached to certain substrates and utilized to capture osteogenic cells when tissue samples such as bone cell isolates, periosteal biopsies, or cultured cells are brought in contact with the attached monoclonal antibodies. The bound cells may then be separated from the solid phase by known methods depending essentially upon the nature of the solid phase and the antibody. The bound cells can be recovered and used for various therapeutic purposes such as for the regeneration of bone, etc., depending upon the various external and internal factors.

As a result, the present invention contemplates any method of employing monoclonal antibodies to separate normal osteogenic cell subsets from other cells such as fibroblastic or hemopoietic cells. For example, a further embodiment of the present invention is directed to a method of producing a population of normal human osteogenic cell subsets comprising the steps of providing a cell suspension of tissue containing such cells; contacting the cell suspension with monoclonal antibodies which recognize an epitope on the osteogenic cells but do not recognize an epitope on the fibroblastic or hemopoietic cells; and separating and recovering from the cell suspension the cells bound by the monoclonal antibodies.

B. Cartilage Cells and Precursors

Chondrocytes are cells found in cartilage. They produce and maintain the cartilaginous matrix. From least- to terminally-differentiated, the chondrocytic lineage starts with colony-forming unit-fibroblasts (CFU-F), which develop into mesenchymal stem cells/marrow stromal cells (MSC), continues to develop into chondrocytes, and then hypertrophic chondrocytes. In the context of bone or cartilage, mesenchymal stem cells (MSC) are commonly known as osteochondrogenic (or osteogenic, chondrogenic, osteoprogenitor, etc.) cells since a single MSC can differentiate into chondrocytes or osteoblasts, depending on the medium. In vivo, differentiation of a MSC in a vascularized area (such as bone) yields an osteoblast, whereas differentiation of a MSC in a non-vascularized area (such as cartilage) yields a chondrocyte. Chondrocytes undergo terminal differentiation when they become hypertrophic, which occurs during endochondral ossification. This last stage is characterized by major phenotypic changes on the cellular level.

The classic markers of the chondrocytic phenotype are Sox9, collagen II, and aggrecan (Sive et al., 2002). Sox9 is known to play a major role in chondrocyte differentiation and maintenance of the chondrocytic phenotype. The product of the collagen II (Col2a1) gene is an early and practically unique marker of chondrocyte differentiation, and aggrecan is the characteristic proteoglycan produced by chondrocytes.

VI. Bone/Cartilage Growth Factors

The use of growth factors from the TGF-β gene superfamily to produce bone ex vivo is an important aspect of the present invention. The following section details attributes of the TGF-β gene superfamily. Of particular use are growth factors that induce the formation of a bone cell spheroid, as defined in the previous section.

The transforming growth factor-β superfamily is a well-characterized family of proteins involved in cellular proliferation and differentiation of cells into various tissues. Members of the TGF-β superfamily are generally dimeric in structure, comprising two monomeric units which are produced by proteolytic cleavage from a larger precursor protein, of which the processed monomer represents the carboxyl terminal portion. The dimeric TGF-β proteins generally have molecular weights of approximately 20,000 to 35,000 and share a common cysteine pattern in the mature protein region. See, for example, Sporn et al. (1986) and the papers cited therein. The TGF-β superfamily includes several subgroups beside TGF-β1 through -β5. These are the bone morphogenetic proteins (BMPs), growth and differentiation factors (GDFs), the inhibins, as well as GDNF and Mullerian inhibitory substance and other structurally related proteins. The TGF-β superfamily also includes proteins from other species, which have been characterized and are highly conserved compared to the mammalian TGF-βs, including Vg1 (*Xenopus*), (Weeks and Melton, 1987); Dpp, Screw and 60A (*Drosophila*), (Padgett et al., 1987; Doctor et al., 1992); and more recently identified proteins including Univin (sea urchin), Dorsalin-1 (chicken) and Radar (Zebrafish). Other factors which may be effectively used in the composition include synthetic molecules or fragments of a TGF-β superfamily member which are able to bind to a TGF-β receptor molecule.

The transforming growth factor-β (TGF-β) family of proteins consists of a number of related, but functionally distinct, proteins (Barnard, 1990; Roberts and Sporn, 1990). One member of the TGF-β family of proteins, TGF-β1, is a multifunctional cytokine with both growth promoting and inhibiting activities. Recently, TGF-β1 has been found to play a role in modulating repair of vascular injuries such as restenosis lesions (Nikol et al., 1992) and atherosclerotic plaques (Kojima et al., 1991).

Members of the TGF-β family of proteins initiate cell signaling by binding to heteromeric receptor complexes of type I (TβRI) and type II (TβRII) serine/threonine kinase receptors (reviewed by Massague et al., 1994; Miyazono et al., 1994). Activation of this heteromeric receptor complex occurs when TGF-β binds to TβRII, which then recruits and phosphorylates TβRI. Activated TβRI then propagates the signal to downstream targets (Chen and Weinberg, 1995; Wrana et al., 1994).

Until now, three distinct types of TGF-βs designated as TGF-β1, TGF-β2 and TGF-β3 which are functionally closely related and share a high degree of receptor cross-reactivity have been cloned and characterized by sequence analysis. All TGF-βs are synthesized as 390 to 412 amino acid precursors that undergo proteolytic cleavage to produce the monomeric forms, which consist of the C-terminal 112 amino acids. In their mature, biologically active forms, TGF-βs are acid- and heat-stable disulfide-linked homodimers of two polypeptide chains of 112 amino acids each. The complete amino acid sequences of human (Derynck et al., 1985), murine (Derynck et al., 1986) and simian TGF-β1 (Sharples et al., 1987) show remarkable sequence conservation, differing only in a single amino acid residue. Comparison of the amino acid sequence of human TGF-β1, human TGF-β2 (de Martin et al., 1987; Marquardt et al., 1987) and human TGF-β3 (Ten Dijke et al. 1988) has demonstrated that the three proteins exhibit in their mature forms about 70-80% sequence identity. A heterodimeric TGF-β1.2 has been isolated from porcine platelets and consists of one subunit of TGF-β1 disulfide-linked to one subunit of TGF-β2 (Cheifetz et al., 1987).

The search for the molecule or molecules responsible for formation of bone, cartilage, tendon and other tissues present in bone and other tissue extracts has led to the discovery of a novel set of molecules called the Bone Morphogenetic Proteins (BMPs), which are also members of the TGF-β gene family. The structures of several proteins, designated BMP-1 through BMP-15, have previously been elucidated. The unique inductive activities of these proteins, along with their presence in bone, cartilage and/or other vital tissues, suggests that they are important regulators of bone and other tissue repair processes, and may be involved in tissue formation, maintenance and repair. There is a need to identify improved methods and compositions for formation, maintenance and repair of such tissues.

Members of the bone morphogenetic protein family have been shown to be useful for induction of cartilage and bone formation. For example, BMP-2 has been shown to be able to induce the formation of new cartilage and/or bone tissue in vivo in a rat ectopic implant model, see U.S. Pat. No. 5,013, 649; in mandibular defects in dogs (Toriumi et al., 1991); in femoral segmental defects in sheep (Gerhart et al., 1991). Other members of the BMP family have also been shown to have osteogenic activity, including BMP-4, -6 and -7 (Wozney, 1993). BMP proteins have also been shown to demonstrate inductive and/or differentiation potentiating activity on a variety of other tissues, including cartilage, tendon, ligament, neural tissue.

Other factors that are useful in accordance with the present invention include the following: BMP-3 (Vukicevic et al., 1989); growth factors, such as basic fibroblast growth factor (bFGF); glucocorticoids, such as dexamethasone (Cheng et al., 1994); and prostaglandins, such as prostaglandin E1

(Chen et al., 1991). Further, ascorbic acid and its analogs, such as ascorbic acid-2-phosphate (Tennenbaum et al., 1982) and glycerol phosphates, such as β-glycerophosphate (Bruder et al., 1991) are effective adjunct factors for advanced differentiation, although alone they do not induce osteogenic differentiation. Other factors include Inhibin A (Chen et al., 1993), chondrogenic stimulatory activity factor (CSA) (Syftestad et al., 1985), collagenous extracellular matrix molecules, including type I collagen, particularly as a gel (Kimura et al., 1984), and vitamin A analogs, such as retinoic acid (Langille et al., 1989).

Also of interest in the present invention are insulin-like growth factors. IGF-I and IGF-II each have a molecular weight of about 7,500 daltons. Each of IGF-I and IGF-II possesses A and B domains that are highly homologous to the corresponding domains of proinsulin. A and B domains are connected to each other by a C domain. A carboxy-terminal extension, the D domain, is present in IGF, but is not found in proinsulin. Both IGF-I and IGF-II are single-chain polypeptides each with 3 disulfide bridges and have a sequence identity of 49% and 47%, respectively, to human insulin A chain and B chain. Like insulin, IGFs stimulate phosphorylation of specific tyrosine residues within the cytoplasmic domain of the receptors to which they bind, as described in WO 93/98826. The designation "insulin-like growth factor" was chosen to express the insulin-like effects and the insulin-like structure of these polypeptides which act as mitogens on a number of cells, as described in EP 128 733. IGF-I is a 70 amino acid peptide, while IGF-II is a 67 amino acid peptide, as described in Rinderknecht (1978a) and (1978b). IGF-I and IGF-II have 62% structural homology to each other. Both have been isolated from human serum.

Insulin-like growth factors are also known under the class name somatomedins, and have been identified in various animal species as polypeptides that act to stimulate growth of cells in a variety of tissues and cell types, particularly during development. Growth promoting effects of somatomedins include enhancement of cell multiplication and stimulation of cartilage proliferation, stimulation of transport of amino acids, stimulation of synthesis of RNA, DNA and protein, and stimulation of incorporation of sulfate into proteoglycan and of proline into collagen. Much mammalian postnatal growth is due to stimulation of cartilage growth by somatomedins and growth in utero may also be somatomedin-dependent.

Yet another important growth factor that can be utilized according to the present invention is vascular endothelial growth factor/vascular permeability factor (VEGF/VPF). This protein is an endothelial cell-specific mitogen which has been shown to be stimulated by hypoxia and required for tumor angiogenesis. Sanger et al. (1986); Kim et al. (1993); Schweiki et al. (1992); Plate et al. (1992). It is a 34-43 kDa (with the predominant species at about 45 kDa) dimeric, disulfide-linked glycoprotein synthesized and secreted by a variety of tumor and normal cells. VEGF appears to play a principle role in many pathological states and processes related to neovascularization VII. Ex Vivo Culturing of Bone and Cartilage Cells The present invention calls for the use of serum-free media for growth and differentiation of the bone and cartilage cells and precursors thereof. The use of serum-free culture for the manufacture of recombinant biopharmaceuticals from mammalian cells has been thoroughly reviewed (Barnes, 1987; Barnes and Sam, 1980; Broad et al., 1991; Jayme, 1991). The list of the main additives which are used as supplements for serum-free media is summarized by Barnes (1987) and Barnes & Sam (1980). Most commercially available serum-free media contain a carrier protein such as albumin. The presence of carrier protein might be required for protection of the cell viability.

An example of serum free culture medium can be found in U.S. Pat. No. 5,063,157, herein incorporated by reference. The media described is for non-adherent mammalian cells comprises, in addition to the base medium, transferrin, insulin, a peptone, a β-D-xylopyranose derivative, selenite and a biological polyamine. Another serum free cell growth medium for mammalian cells is disclosed in U.S. Pat. No. 4,443,546. This growth medium, in addition to the basic medium, contains seven ingredients. European Patent Application 481,791 discloses a culture medium for CHO cells comprising water, an osmolality regulator, a buffer, an energy source, amino acids, an iron source, a growth factor and other optional components. The two media exemplified contain 19 and 17 components, respectively. Other additives are disclosed below.

A. Albumin

Albumin is preferably supplied in the form of bovine (BSA) or human serum albumin (HSA) in an effective amount for the growth of cells. Albumin provides a source of protein in the media. Albumin is thought to act as a carrier for trace elements and essential fatty acids. Preferably, the albumin used in the present formulations is free of pyrogens and viruses, and when necessary, is approved regulatory agencies for infusion into human patients. The HSA may be deionized using resin beads prior to use. The concentration of human serum albumin is 1-8 mg/ml, more particularly 3-5 mg/ml, and specifically 4 mg/ml.

B. Soluble Carrier/Fatty Acid Complex

The albumin mentioned above could be substituted by a soluble carrier/essential fatty acid complex and a soluble carrier cholesterol complex which can effectively deliver the fatty acid and cholesterol to the cells. An example of such a complex is a cyclodextrin/linoleic acid, cholesterol and oleic acid complex. This is advantageous as it would allow for the replacement of the poorly characterized albumin with a well defined molecule. The use of cyclodextrin removes the need for the addition of human/animal serum albumin, thereby eliminating any trace undesired materials which the albumin would introduce into the media. The use of cyclodextrin simplifies the addition of specific lipophilic nutrients to a serum-free culture.

The lipophilic substances which can be complexed with cyclodextrin include unsaturated fatty acids such as linoleic acid, cholesterol and oleic acid. The linoleic acid, cholesterol and oleic acid are present in effective amounts and can be present in equal proportions such that the total amount is 0.001 to 100 μg/ml, particularly 0.1 to 10 μg/ml. The preparation of such complexes is known in the art and is described, for example, in U.S. Pat. No. 4,533,637, the entire contents of which is hereby incorporated by reference.

C. Iron Source

A source of iron in an effective amount and in a form that can be utilized by the cells can be added to the media. The iron can be supplied by saturating transferrin, its carrier molecule, in an effective amount. The transferrin may be derived from animal sera or recombinantly synthesized. It is understood that when transferrin is derived from an animal source, it is purified to remove other animal proteins, and thus is usually at least 99% pure. The transferrin concentration is usually between 80 and 500 μg/ml, in particular between 120 and 500 μg/ml, more particularly between 130 and 500 μg/ml, even more particularly between 275 and 400 μg/ml and specifically 300 μg/ml. An iron salt, preferably a water soluble iron salt, such as iron chloride (e.g., $FeCl_3.6H_2O$) dissolved in an aqueous solution such as an organic acid solution (e.g., citric acid) is used to supply the iron to transferrin. One mole of iron chloride is usually used for every mole of citric acid. The concentration of iron chloride is 0.0008 to 8 μg/ml, more particularly 0.08 to 0.8 μg/ml, and specifically 0.08 μg/ml.

D. Insulin Growth Factor

Insulin also may be added to the media of the present invention in an effective amount. The insulin concentration is between 0.25 and 2.5 U/ml, more preferably 0.4-2.1 U/ml, most preferably 0.48 U/ml. In the conversion of Units to mass, 27 U=1 mg. Therefore, incorporating the conversion, the insulin concentration is approximately between 9.26 μg/ml and 92.6 μg/ml, more particularly between 14.8 μg/ml and 77.8 μg/ml, and specifically 17.7 μg/ml. It is again understood that human insulin is more desirable than animal insulin. Highly purified recombinant insulin is most preferred. An insulin like growth factor such as insulin like growth factor 1 and insulin like growth factor 2 may be used in place of or in addition to insulin in an amount which provides substantially the same result as a corresponding amount of insulin. Thus, the term "insulin growth factor" includes both insulin and insulin like growth factors.

E. Additional Components

The addition of other lipids to the above essential reagents could enhance the proliferative potential of precursor cells. These components, however, are preferably not added unless they are necessary for a particular experiment or to grow a particular type of cell. Optionally, triglycerides and/or phospholipids may be included as additional sources of lipid. A preferable source of lipid contains a mixture of neutral triglycerides of predominantly unsaturated fatty acids such as linoleic, oleic, palmitic, linolenic, and stearic acid. Such a preparation may also contain phosphatidylethanolamine and phosphatidylcholine. Another source of lipid is a human plasma fraction precipitated by ethanol and preferably rendered virus free by pasteurization.

Other ingredients which can optionally be added to the media are cited in the following references: WO 95/06112, U.S. Pat. Nos. 4,533,637, 5,405,772. The entire contents of all of these references are incorporated by reference.

F. Undesired Components

When the media is to be used to grow cells for introduction into a human patient, the media preferably does not contain ingredients such as bovine serum albumin, mammalian serum, and/or any natural proteins of human or mammalian origin (as explained above). It is preferable that recombinant or synthetic proteins, if they are available and of high quality, are used. Most preferably, the amino acid sequences of the recombinant or synthetic proteins are identical to or highly homologous with those of humans. Thus, the most preferable serum-free media formulations herein contain no animal-derived proteins and do not have even a non-detectable presence of animal protein.

In the most ideal system, optional components which are not necessary are preferably not added to the medium. Such optional components are described in the prior art cited above and may be selected from the group consisting of meat extract, peptone, phosphatidylcholine, ethanolamine, antioxidants, deoxyribonucleosides, ribonucleosides, soy bean lecithin, corticosteroids, myoinositol, monothioglycerol, and bovine or other animal serum albumin.

VIII. Pharmaceutical Formulations and Routes of Administration

The compounds of the present invention may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

Active compounds are administered at a therapeutically effective dosage sufficient to treat a condition associated with a condition in a patient. A "therapeutically effective amount" preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the examples and drawings.

IX. Diseases and Conditions Requiring Bone Repair

The following is a brief discussion of several conditions to exemplify the variety of diseases and disorders that would benefit from the development of new technology to improve bone/cartilage repair and healing processes. In addition to the following, several other conditions, such as vitamin D deficiency, may also benefit from such treatments.

A. Fracture

The first example is the otherwise healthy individual who suffers a fracture. Often, clinical bone fracture is treated by casting to alleviate pain and allow natural repair mechanisms to repair the wound. There has been progress in the treatment of fracture in recent times, however, even without considering the various complications that may arise in treating fractured bones, any new procedures to increase bone healing in normal circumstances would be represent a great advance.

B. Osteogenesis Imperfecta

A second example which may benefit from new treatment methods is osteogenesis imperfecta (OI). OI encompasses various inherited connective tissue diseases that involve bone and soft connective tissue fragility in humans (Byers & Steiner, 1992; Prockop, 1990). About one child per 5,000-14,000 born is affected with OI and the disease is associated with significant morbidity throughout life. A certain number of deaths also occur, resulting from the high propensity for bone fracture and the deformation of abnormal bone after fracture repair (OI types II-IV; Bonadio & Goldstein, 1993). The relevant issue here is quality of life; clearly, the lives of affected individuals would be improved by the development of new therapies designed to stimulate and strengthen the fracture repair process.

OI type I is a mild disorder characterized by bone fracture without deformity, blue sclerae, normal or near normal stature, and autosomal dominant inheritance (Bonadio & Goldstein, 1993). Osteopenia is associated with an increased rate of lone bone fracture upon ambulation (the fracture frequency decreases dramatically at puberty and during young adult life, but increases once again in late middle age). Hearing loss, which often begins in the second or third decade, is a feature of this disease in about half the families and can progress despite the general decline in fracture frequency. Dentinogenesis imperfecta is observed in a subset of individuals.

In contrast, OI types II-VI represent a spectrum of more severe disorders associated with a shortened life-span. OI type II, the perinatal lethal form, is characterized by short stature, a soft calvarium, blue sclerae, fragile skin, a small chest, floppy appearing lower extremities (due to external rotation and abduction of the femurs), fragile tendons and ligaments, bone fracture with severe deformity, and death in the perinatal period due to respiratory insufficiency. Radiographic signs of bone weakness include compression of the femurs, bowing of the tibiae, broad and beaded ribs, and calvarial thinning.

OI type III is characterized by short stature, a triangular facies, severe scoliosis, and bone fracture with moderate deformity. Scoliosis can lead to emphysema and a shortened life-span due to respiratory insufficiency. OI type IV is characterized by normal sclerae, bone fracture with mild to moderate deformity, tooth defects, and a natural history that essentially is intermediate between OI type II and OI type I.

More than 150 OI mutations have been characterized since 1989 (reviewed in Byers & Steiner, 1992; Prockop, 1990). The vast majority occur in the COL1A1 and COL1A2 genes of type I collagen. Most cases of OI type I appear to result from heterozygous mutations in the COL1A1 gene that decrease collagen production but do not alter primary structure, i.e., heterozygous null mutations affect COL1A1 expression.

C. Osteoporosis

A third, important example is osteoporosis. The term osteoporosis refers to a heterogeneous group of disorders characterized by decreased bone mass and fractures. An estimated 20-25 million people are at increased risk for fracture because of site-specific bone loss. Risk factors for osteoporosis include increasing age, gender (more females), low bone mass, early menopause, race (Caucasians), low calcium intake, reduced physical activity, genetic factors, environmental factors (including cigarette smoking and abuse of alcohol or caffeine), and deficiencies in neuromuscular control that create a propensity to fall.

More than a million fractures in the USA each year can be attributed to osteoporosis, and in 1986 alone the treatment of osteoporosis cost an estimated 7-10 billion health care dollars. Demographic trends (i.e., the gradually increasing age of the U.S. population) suggest that these costs may increase to $62 billion by the year 2020. Clearly, osteoporosis is a significant health care problem.

Clinically, osteoporosis is segregated into type I and type II. Type I osteoporosis occurs predominantly in middle aged women and is associated with estrogen loss at the menopause, while osteoporosis type II is associated with advancing age. Much of the morbidity and mortality associated with osteoporosis results from immobilization of elderly patients following fracture.

Current therapies for osteoporosis patients focus on fracture prevention, not fracture repair. This remains an important consideration because of the literature, which clearly states that significant morbidity and mortality are associated with prolonged bed rest in the elderly, particularly those who have suffered hip fractures. Complications of bed rest include blood clots and pneumonia. These complications are recognized and measures are usually taken to avoid them, but these is hardly the best approach to therapy thus, the osteoporotic patient population would benefit from new therapies designed to strengthen bone and speed up the fracture repair process, thus getting these people on their feet before the complications arise.

D. Osteoarthritis

Current estimations suggest that 40 million Americans of all ages are affected by osteoarthritis and that 70 to 90 percent of Americans older than 75 years have at least one involved joint. Estimates of the prevalence of osteoarthritis based on radiographic evidence range from 30 to 90 percent. Men and women are equally affected, but symptoms occur earlier and appear to be more severe in women. Common synonyms for osteoarthritis include osteoarthrosis and degenerative joint disease. Osteoarthritis is not an inevitable consequence of aging. It is an acquired degenerative process that can be managed effectively by family physicians.

The exact etiology of osteoarthritis is unknown. Multiple factors (e.g., heredity, trauma, and obesity) interact to cause this disorder. Any event that changes the environment of the chondrocyte has the potential to cause osteoarthritis. Although usually occurring as a primary disorder, osteoarthritis can occur secondary to other processes. Although the term "osteoarthritis" is often used, "osteoarthrosis" may be more appropriate. Degenerative changes are the predominant factor contributing to disability. In joints with osteoarthritis, inflammation may be present; however, it is usually mild and involves only the periarticular tissues.

The pathophysiology involves a combination of mechanical, cellular, and biochemical processes. The interaction of these processes leads to changes in the composition and mechanical properties of the articular cartilage. Cartilage is composed of water, collagen, and proteoglycans. In healthy cartilage, continual internal remodeling occurs as the chondrocytes replace macromolecules lost through degradation. This process becomes disrupted in osteoarthritis, leading to increased degenerative changes and an abnormal repair response.

Joint use provides physiologic stimulation through the noncellular matrix that helps direct chondrocyte synthetic activity and internal tissue remodeling. Prolonged decreased joint use leads to changes in the matrix composition, resulting in subsequent loss of tissue function. The resumption of joint use can help restore the properties of the joint toward normal.

The strong association between age and osteoarthritis may be best explained by age-related changes in the matrix composition and a decrease in chondrocyte function and responsiveness to stimuli. These changes can interfere with continued internal remodeling, maintenance of the tissue, and loss of cartilage. This leads to an increased risk for cartilage degradation and injury to include surface defects in the articular cartilage. The abnormal repair process leads to the formation of osteophytes and subchondral cysts as the disease progresses. These changes are evident on radiographs.

Primary and secondary prevention should be emphasized in the management of patients with osteoarthritis. Maintaining appropriate body weight may be the single most important factor in preventing osteoarthritis from occurring in weight-bearing joints.[8] A relationship has been shown between weight loss and a reduction in the risk of developing osteoarthritis.

The role of exercise in the development of osteoarthritis has been difficult to ascertain for a variety of reasons. Results of studies have demonstrated radiographic evidence of osteoarthritis in former athletes. In some of these studies, the symptoms were greater in the athletes than in the control subjects, while in other studies, the athletes were either asymptomatic or had symptoms similar to those of the control subjects. However, results from case-control and long-term prospective studies of runners have demonstrated that distance running does not increase the risk for osteoarthritis. Nevertheless, it is clear that a history of significant injury, particularly of the knee or hip, is a risk factor for the development of osteoarthritis. A history of menisectomy is also considered a risk factor; therefore, sports that have a high risk for injury may lead to a greater risk for the development of osteoarthritis. High-risk sports include collision sports and those with a high-loading or torsional impact.

In general, mild-to-moderate activity is not likely to lead to osteoarthritis in normal joints. Persons with previous joint injury or surgery, or abnormal joint alignment, are likely to be at a higher risk for developing osteoarthritis.

Vitamin D intake may also affect osteoarthritis. Low dietary intake or serum levels of vitamin D are associated with increased rates of progression.

The diagnosis of osteoarthritis is largely made by obtaining a detailed history and conducting a complete physical examination. Ancillary diagnostic tests may occasionally be necessary when the diagnosis remains uncertain. The usual presenting symptom is pain involving one or only a few joints. Joint involvement is usually symmetric. Morning joint stiffness that usually resolves within 30 minutes or occurs with mild-to-moderate activity is also common. As the disease progresses, prolonged joint stiffness and joint enlargement are evident. Crepitus, or a grating sensation in the joint, is a late manifestation. Limitation of joint movement may be due to flexion contractures or mechanical obstructions.

Secondary causes should be considered when making decisions about having ancillary tests performed. Further evaluation is indicated when the diagnosis remains uncertain, response to therapy is not as expected, or significant clinical changes occur. Clinically indicated laboratory work may include tests for erythrocyte sedimentation rate and rheumatoid factor. Synovial fluid analysis may be conducted to help exclude other diagnoses. In osteoarthritis, the white blood cell count is usually less than 500 cells per $mm^2$ (0.5 3 $10^9$ per L) and is composed predominantly of mononuclear cells. In inflammatory aspirates, the white blood cell count is usually greater than 2,000 cells per $mm^2$ (2.0 3 $10^9$ per L), and the predominant cell type is usually the neutrophil.

Radiographs can provide objective evidence of the disease. Findings consistent with osteoarthritis include presence of joint space narrowing, osteophyte formation, pseudocyst in subchondral bone, and increased density of subchondral bone. The absence of radiographic changes, however, does not exclude the diagnosis of osteoarthritis. Many patients with radiographic changes consistent with osteoarthritis are asymptomatic or do not exhibit any disability, suggesting that the presence of radiographic changes in the absence of symptoms should not lead to the diagnosis of osteoarthritis. In large joints, radiographs can exclude other causes of joint pain.

Radiographs are not required for every person who presents with symptoms consistent with osteoarthritis. Patients whose clinical history or course suggests other etiologies should undergo radiographic evaluation. This includes patients with trauma, joint pain at night, progressive joint pain (without prior radiography), significant family history of inflammatory arthritis, and children younger than 18 years.

The primary goals of treatment are improved function and quality of life. Treatment should be tailored to the needs of the individual patient. Patient education, rehabilitation, exercise, modification of activities of daily living, pharmacotherapy, alternative medicine and surgery are all treatment modalities that should be considered.

Patients should be thoroughly educated about the natural course of osteoarthritis. Their role in the management of the disease is critical, and a proper understanding will allow appropriate expectations of treatment to be established. Family physicians should be familiar with pharmacologic and nonpharmacologic treatment modalities to maximize effective utilization and a thorough understanding of the short- and long-term complications and cost. Some treatment modalities (e.g., heat, ice, and electrical stimulation) may make the patient feel better but may not be sufficient alone. Most modalities and therapies do not change the outcome.

Combinations of treatment modalities for symptom control are better than isolated therapy for symptom relief. The proper mix of modalities and exercises is based on individualized treatment goals agreed on by the family physician and the patient.

Patients with osteoarthritis often demonstrate significant disability. The symptoms and disability may limit their ability to participate in regular physical activity, and they may also be reluctant to exercise for fear that it will exacerbate their symptoms. It has been shown that aerobic and resistance exercises do not exacerbate symptoms in patients with osteoarthritis and do not appear to produce or exacerbate joint symptoms in persons without osteoarthritis. Results of randomized studies have demonstrated that aerobic and resistance exercises produce only modest gains in measures of improving disability, physical performance, and symptoms. Participation in regular exercise appears to be safe and effective in managing the symptoms and disability associated with osteoarthritis. Exercise programs such as those sponsored by the Arthritis Foundation should be recommended to patients with osteoarthritis. It is important for patients to note that any lifestyle changes they make are not curative and must be continued throughout life.

Pain is the primary symptom of osteoarthritis, and multiple medications are available to relieve pain and improve function. The choice of a pain-control medication must be individualized, prescribing medications with the best side effect profile first and adding other pain-control medications as indicated. In comparison with nonsteroidal anti-inflammatory drugs (NSAIDs), acetaminophen, in a dosage of 1 g four times daily, is considered an initial drug of choice. NSAIDs and aspirin have analgesic and anti-inflammatory properties but also have adverse effects on the stomach and kidney, especially in elderly patients. The cyclooxygenase-2 (COX-2) inhibitors celecoxib (Celebrex) and rofecoxib (Vioxx) cause fewer gastrointestinal side effects and, while thought to be no more effective then other NSAIDs, can be considered for use in patients with a history of gastrointestinal bleeding or those who may be taking certain medications (e.g., warfarin [Coumadin] or oral steroids). The COX-2 inhibitors have not been shown to be safer than acetaminophen. Cost should be a consideration in treatment decisions. In addition, there is accumulating data about the side effects of the COX-2 inhibitors. Early evidence indicated that side effects might vary between the medications in this class.

Sodium hyaluronate (Synvisc, Hyalgan) is indicated only for the treatment of patients with osteoarthritis of the knee. This treatment is an alternative to consider in patients who do not respond to NSAID therapy or who have a history of gastric ulcer disease, with some evidence suggesting symptomatic and functional improvement following a series of weekly injections.

Intra-articular steroid injections are another treatment option but should not, in most circumstances, be administered more than three to four times per year. Results of a multicenter, randomized study demonstrated that intra-articular knee injections significantly reduced pain for up to four weeks. No functional improvement was noted compared to placebo. Results from this same study revealed that joint lavage significantly relieved pain for up to 24 weeks. The effects of steroid injection and joint lavage on pain relief were additive, but neither procedure significantly improved functional status. Topical capsaicin cream should be considered for adjunctive treatment of focal joint pain.

Alternative medicines (e.g., glucosamine sulfate, chondroitin sulfate) in the prevention and treatment of osteoarthritis continue to receive coverage in the media; however, research evaluating their efficacy and potential benefits is incomplete. Glucosamine sulfate, a popular treatment for osteoarthritis, is an amino-monosaccharide and a substrate of glycosaminoglycans and proteoglycans. These are substrates of hyaluronic acid, a major component of joint fluid. Glucosamine is often taken alone or in combination with chondroitin sulfate. Results from some studies have shown glucosamine to be as effective as ibuprofen in relieving the pain of osteoarthritis. Chondroitin sulfate also has demonstrated efficacy in improving the symptoms of osteoarthritis. A full review of alternative treatment modalities is beyond the scope of this article.

Family physicians should be aware of commonly used alternative treatments. This allows monitoring of potential benefits and possible interactions with other medications. An awareness of the medical literature also permits physicians to provide evidence-based recommendations for individual patient therapeutic trials. Alternative care should be critically assessed like any other medical care. It is through such assessments that a medication such as capsaicin, which is derived from the red pepper plant, has become part of conventional medicine.

E. Bone Reconstruction

A fourth example is related to bone reconstruction and, specifically, the ability to reconstruct defects in bone tissue that result from traumatic injury; as a consequence of cancer or cancer surgery; as a result of a birth defect; or as a result of aging. There is a significant need for more frequent orthopedic implants, and cranial and facial bone are particular targets for this type of reconstructive need. The availability of new implant materials, e.g., titanium, has permitted the repair of relatively large defects. Titanium implants provide excellent temporary stability across bony defects. However, experience has shown that a lack of viable bone bridging the defect can result in exposure of the appliance, infection, structural instability and, ultimately, failure to repair the defect.

Autologous bone grafts are another possibility, but they have several demonstrated disadvantages in that they must be harvested from a donor site such as iliac crest or rib, they usually provide insufficient bone to completely fill the defect, and the bone that does form is sometimes prone to infection and resorption. Partially purified xenogeneic preparations are not practical for clinical use because microgram quantities are purified from kilograms of bovine bone, making large scale commercial production both costly and impractical. Allografts and demineralized bone preparations are therefore often employed.

Microsurgical transfers of free bone grafts with attached soft tissue and blood vessels can close bony defects with an immediate source of blood supply to the graft. However, these techniques are time consuming, have been shown to produce a great deal of morbidity, and can only be used by specially trained individuals. Furthermore, the bone implant is often limited in quantity and is not readily contoured. In the mandible, for example, the majority of patients cannot wear dental appliances using presently accepted techniques (even after continuity is established), and thus gain little improvement in the ability to masticate. Toriumi et al. 1991 have written the "Reconstructive surgeons should have at their disposal a bone substitute that would be reliable, biocompatible, easy to use, and long lasting and that would restore mandibular continuity with little associated morbidity."

In connection with bone reconstruction, specific problem areas for improvement are those concerned with treating large defects, such as created by trauma, birth defects, or particularly, following tumor resection; and also the area of artificial joints. The success of orthopedic implants, interfaces and artificial joints could conceivably be improved if the surface of the implant, or a functional part of an implant, were to be coated with a bone stimulatory agent. The surface of implants could be coated with one or more appropriate materials in order to promote a more effective interaction with the biological site surrounding the implant and, ideally, to promote tissue repair.

X. Polymers for Implanting of Bone Cell Spheroids

Over the last decade there has been a tremendous increase in applications for polymeric materials. These materials are well suited to implantation as they can serve as a temporary scaffold to be replaced by host tissue, degrade by hydrolysis to non-toxic products, and be excreted, as described by Kulkarni et al. (1971) and Hollinger and Battistone (1986).

Either natural or synthetic polymers can be used to form the matrix, although synthetic polymers are preferred for reproducibility and controlled release kinetics. Synthetic polymers that can be used include bioerodible polymers such as poly(lactide) (PLA), poly(glycolic acid) (PGA), poly(lactide-co-glycolide) (PLGA), and other poly(alpha-hydroxy acids), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolifins, polyethylene oxide, polyvinyl alcohol, and nylon. Although non-degradable materials can be used to form the matrix or a portion of the matrix, they are not preferred. Examples of natural polymers include proteins such as albumin, fibrin or fibrinogen, collagen, synthetic polyamino acids, and prolamines, and polysaccharides such as alginate, heparin, and other naturally occurring biodegradable polymers of sugar units.

Four polymers widely used in medical applications are poly(paradioxanone) (PDS), poly(lactic acid) (PLA), poly(glycolic acid) (PGA), and PLAGA copolymers. Copolymerization enables modulation of the degradation time of the material. By changing the ratios of crystalline to amorphous polymers during polymerization, properties of the resulting material can be altered to suit the needs of the application. These polymers, including poly(lactide-co-glycolic) acid (PLGA), have been used as polymer composites for bone replacement as reported by Elgendy et al. (1993). Substituted polyphosphazenes have been shown to support osteogenic cell growth, as reported by Laurencin et al. (1993). Poly(organophosphazenes) are high molecular weight polymers containing a backbone of alternating phosphorus and nitrogen atoms. There are a wide variety of polyphosphazenes, each derived from the same precursor polymer, poly(dichlorophosphazene). The chlorine-substituted species can be modified by replacement of the chlorine atoms by different organic nucleophiles such as o-methylphenoxide along with amino acids. The physical and chemical properties of the polymer can be altered by adding various ratios of hydrolytic sensitive side chains such as ethyl glycinate, as described by Wade et al. (1978) and Allcock and Fuller (1981). This will affect the degradation of the polymer as an implantable and biodegradable material as well as vary the support of osteogenic cells for bone and tissue implants, as shown by Laruencin et al. (1993).

PLA, PGA and PLA/PGA copolymers are particularly useful for forming the biodegradable matrices. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. patents, the teachings of which are hereby incorporated by reference, describe in detail suitable polylactides, their properties and their preparation: U.S. Pat. Nos. 1,995,970; 2,703,316; 2,758,987; 2,951,828; 2,676,945; 2,683,136; and 3,531,561. PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in "Cyanamid Research Develops World's First Synthetic Absorbable Suture," Chemistry and Industry, 905 (1970).

The erosion of the matrix is related to the molecular weights of PLA, PGA or PLA/PGA. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives. Poly(lactide-co-glycolide) (50:50), degrades in about six weeks following implantation.

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

These polymers are particularly useful in forming fibrous or sponge type matrices for implantation. Polymers can also be used to form hydrogels in which the cells are suspended and then implanted.

A. Other Matrix Materials

Another class of materials for making the matrix is hydroxyapatite, or a similar ceramic formed of tricalcium phosphate (TCP) or calcium phosphate (CaPO$_4$). Calcium hydroxyapatites occur naturally as geological deposits and in normal biological tissues, principally bone, cartilage, enamel, dentin, and cementum of vertebrates and in many sites of pathological calcifications such as blood vessels and skin. Synthetic calcium hydroxyapatite is formed in the laboratory either as pure $Ca_{10}(PO_4)_6(OH)_2$ or hydroxyapatite that is impure, containing other ions such as carbonate, fluoride, chloride for example, or crystals deficient in calcium or crystals in which calcium is partly or completely replaced by other ions such as barium, strontium and lead. Essentially none of the geological and biological apatites are "pure" hydroxyapatite since they contain a variety of other ions and cations and may have different ratios of calcium to phosphorous than the pure synthetic apatites.

In general, the crystals of pure synthetic apatites, geological apatites and many impure synthetically produced apatites are larger and more crystalline than the biological crystals of bone, dentin, cementum and cartilage. The crystals of bone, dentin and cementum are very small, irregularly shaped, very thin plates whose rough average dimensions are approximately 10 to 50 angstroms in thickness, 30 to 150 angstroms in width, and 200 to 600 angstroms in length. The synthetic materials are highly diverse, as reported in the literature. For example, the characterization of four commercial apatites was reported by Pinholt et al. (1992); Marden et al. (1990) reports on a protein, biodegradable material; Pinholt et al. (1991) reports on the use of a bovine bone material called Bio-Oss™; Friedman et al. (1991) and Costantino et al. (1991) report on a hydroxyapatite cement; Roesgen (1990) reports on the use of calcium phosphate ceramics in combination with autogenic bone; Ono et al. (1990) reports on the use of apatite-wollastonite containing glass ceramic granules, hydroxyapatite granules, and alumina granules; Passuti et al. (1989) reports on macroporous calcium phosphate ceramic performance; Harada (1989) reports on the use of a mixture of hydroxyapatite particles and tricalcium phosphate powder for bone implantation; Ohgushi et al. (1989) reports on the use of porous calcium phosphate ceramics alone and in combination with bone marrow cells; Pochon et al. (1986) reports on the use of beta-tricalcium phosphate for implantation; and Glowacki et al. (1985), reports on the use of demineralized bone implants.

As used herein, all of these materials are generally referred to as "hydroxyapatite." In the preferred form, the hydroxyapatite is particles having a diameter between approximately ten and 100 microns in diameter, most preferably about 50 microns in diameter.

Calcium phosphate ceramics can be used as implants in the repair of bone defects because these materials are non-toxic, non-immunogenic, and are composed of calcium and phosphate ions, the main constituents of bone (Frame, 1987; Parsons et al., 1988). Both tricalcium phosphate (TCP) $Ca_3(PO_4)_2$ and hydroxyapatite (HA) $Ca_{10}(PO_4)_6(OH_2)$ have been widely used. Calcium phosphate implants are osteoinductive, and have the apparent ability to become directly bonded to bone. As a result, a strong bone-implant interface is created.

Calcium phosphate ceramics have a degree of bioresorbability which is governed by their chemistry and material structure. High density HA and TCP implants exhibit little resorption, while porous ones are more easily broken down by dissolution in body fluids and resorbed by phagocytosis. However, TCP degrades more quickly than HA structures of the same porosity in vitro. HA is relatively insoluble in aqueous environments. However, the mechanical properties of calcium phosphate ceramics make them ill-suited to serve as a structural element under load bearing circumstances. Ceramics are not preferred since they are brittle and have low resistance to impact loading.

B. Polymers for Forming Hydrogels

Polymers that can form ionic hydrogels which are malleable can also be used to support the cells. Injecting a suspension of cells in a polymer solution may be performed to improve the reproducibility of cell seeding throughout a device, to protect the cells from shear forces or pressure induced necrosis, or to aid in defining the spatial location of cell delivery. The injectable polymer may also be utilized to deliver ells and promote the formation of new tissue without the use of any other matrix. In a preferred embodiment, the hydrogel is produced by cross-linking the ionic salt of a polymer with ions, whose strength increases with either increasing concentrations of ions or polymer. The polymer solution is mixed with the cells to be implanted to form a suspension, which is then injected directly into a patient prior to polymerization of the suspension. The suspension subsequently polymerizes over a short period of time due to the presence in vivo of physiological concentrations of ions such as calcium in the case where the polymer is a polysaccharide such as alginate.

A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazenes, and polyacrylates such as hydroxyethyl methacrylate (HEMA), which are crosslinked ionically, or block copolymers such as Pluronics™ or Tetronics™, polyethylene oxide-polypropylene glycol block copolymers which are crosslinked by temperature or pH, respectively. Other materials include proteins such as fibrinogin, collagen, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly (phosphazenes), poly(acrylic acids), poly(methacrylic acids), copolymers of acrylic acid and methacrylic acid, poly (vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups. Examples of polymers with basic side groups that can be reacted with anions are poly (vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883. Described therein is an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolyrically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol and glucosyl.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005M have been demonstrated to cross-link the polymer. Higher concentrations are limited by the solubility of the salt. The preferred anions for cross-linking of the polymers to form a hydrogel are divalent and trivalent anions such as low molecular weight dicarboxylic acids, for example, terephthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine), examples of synthetic polyamines are: polyethyleneimine, poly(vinylamine), and poly(allyl amine). There are also natural polycations such as the polysaccharide, chitosan. Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

XI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials And Methods

Neonatal murine calvarial bone formation assay. The technique for studying organ cultures of neonatal murine calvarial bones has been described in detail previously (Traianedes et al., 1999, Mundy et al., 1999). The bones were removed from the calvaria of 4-5 day old ICR Swiss mice, and then cultured in BGJ medium with 0.1% BSA for 7 Days using 4 calvarial bones per group triterpenoids in differing amounts were added for 7 days. Alkaline phosphatase was determined at 4 and 7 days and expressed as arbitrary units of alkaline phosphatase activity. At the end of the experiment the media was saved and assayed for the presence of alkaline phosphatase and the calvaria bones were then fixed overnight in 10% formalin, decalcified in 14% EDTA overnight and were then embedded in paraffin wax. Sections were cut, using a standard microtome, along the midline suture to reveal the sagittal suture and the region posterior to this suture. Four micrometer sections were taken initially and at two sequential 400 nm depths. Sections were placed on coated glass slides (Superfrost plus, Fisher Scientific, Pittsburgh, Pa.) and stained with hematoxylin and eosin. The effects on bone formation were evaluated by morphologic assessment.

Imaging. Digital images across sections of the neonatal murine calvaria were taken from each group. Histomorphometric analysis was performed on these calvarial images using the Osteomeasure System (Osteometrics Inc., Atlanta, Ga.). The total and new bone area (expressed as $mm^2 \times 10^{-3}$) was determined on all images across the calvarial section.

Bovine calf stifle joint SZP assay. Bovine calf stifle joints were dissected under aseptic conditions. The superficial zone of articular cartilage of femoral condyles (approximately 100 μm thickness) was harvested using a dermatome. The cartilage slices were digested with 0.2% collagenase P in culture medium. Isolated chondrocytes were plated in monolayer at a density of $1 \times 10^5$ cells/well (approximately $2.5 \times 10^4$ cells/$cm^2$) in 12-well culture plates and incubated at 37° C. in a moist atmosphere of 5% carbon dioxide and 95% air. Chondrocytes were cultured in D-MEM/F-12 containing 10% fetal bovine serum over night, and then the media were changed in serum-free D-MEM/F-12 supplemented with ITSL (insulin, transferrin, selenious acid, and linoleic acid). Both media contain 100 U/ml penicillin, 100 μg/ml streptomycin, 50 μg/ml ascorbate-2-phosphate, and 0.1% bovine serum albumin. After changing the media with serum into the serum-free chemically defined media, various concentration of synthetic triterpenoids were added into the cell culture.

As most of SZP is secreted into the culture medium, supernatants were harvested as samples and the SZP synthesis was analyzed by SDS-PAGE and Western blotting using a monoclonal antibody S6.79, obtained from Rush Medical College, Chicago, Ill. SZP accumulation into the culture medium was also quantified by ELISA using purified SZP as standard.

The accumulation of SZP into the culture media increased in a time-dependent manner (Day 1<Day 2<Day 3). Therefore the culture of media of Day 3 was used for all the studies.

Example 2

Calvarial Bone Formation Results

Experimental groupings for FIGS. 1-12 are shown below (The alphabet at the end of each compound number denotes synthesis batch of each one.):

| Gp1 - Control | |
|---|---|
| Gp2 - TP-151F | 40 Nm |
| Gp3 - TP-151F | 200 nM |

-continued

| | |
|---|---|
| Gp4 - TP-151F | 1000 nM |
| Gp5 - Control | |
| Gp6 - TP-155C | 40 nM |
| Gp7 - TP-155C | 200 nM |
| Gp8 - TP-155C | 1000 nM |
| Gp9 - Control | |
| Gp10 - TP-235H | 40 nM |
| Gp11 - TP-235H | 200 nM |
| Gp12 - TP-235H | 1000 nM |
| Gp13 - Control | |
| Gp14 - TP-319A | 40 nM |
| Gp15 - TP-319A | 200 nM |
| Gp16 - TP-319A | 100 nM |

Figure 2:
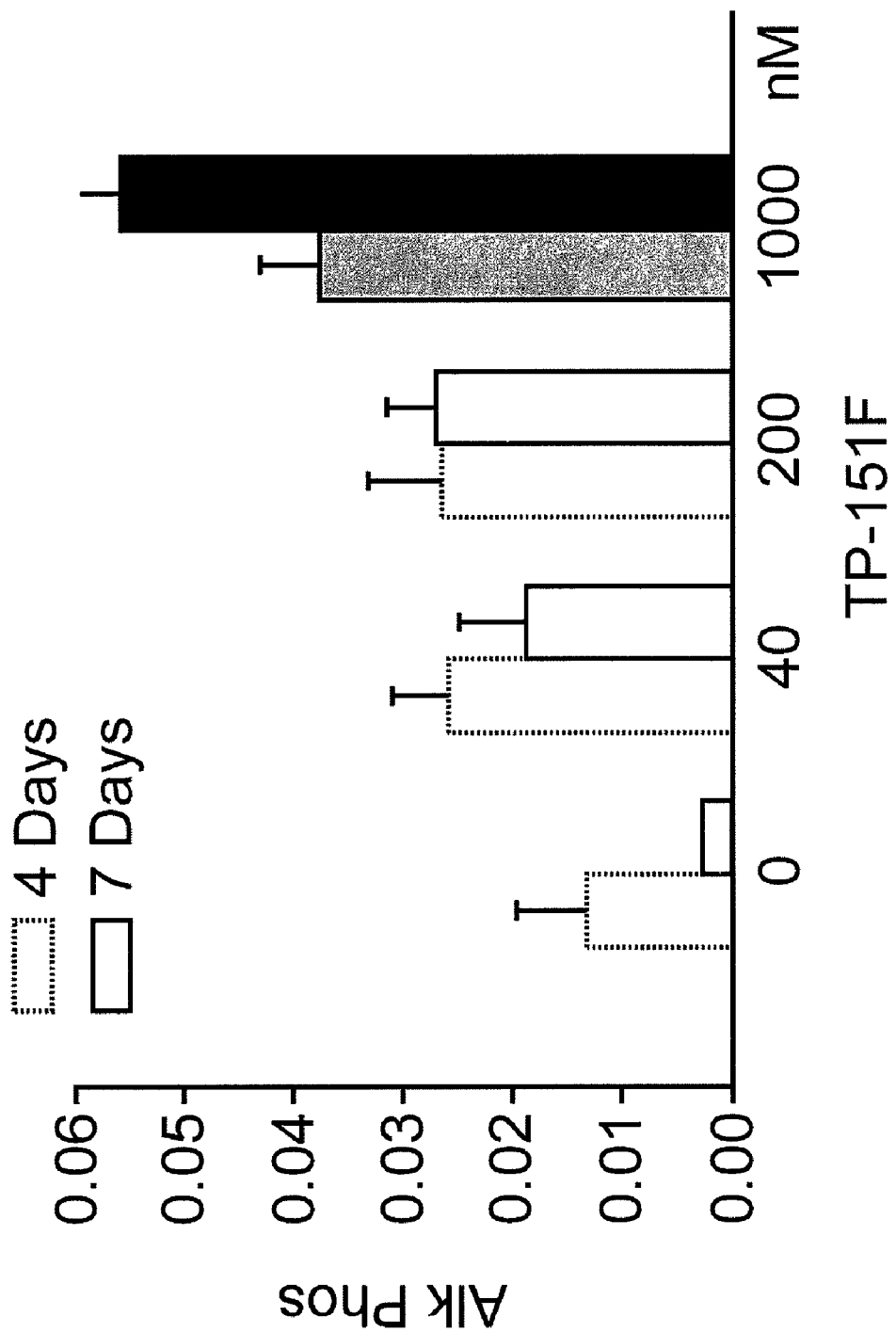
FIGS. 2, 5, 8 and 11—Alkaline phosphatase activity in cultures following treatment with varying concentrations of drug. AkPh activity was measured in vitro at 4 and 7 days at concentrations of 0, 40, 200 and 100 nM for each of TP-151F (FIG. 2), TP-155C (FIG. 5), TP-235H (FIG. 8) and TP-319A (FIG. 11). (The alphabet at the end of each compound number denotes the synthesis batch of each one.)
Figure 3:
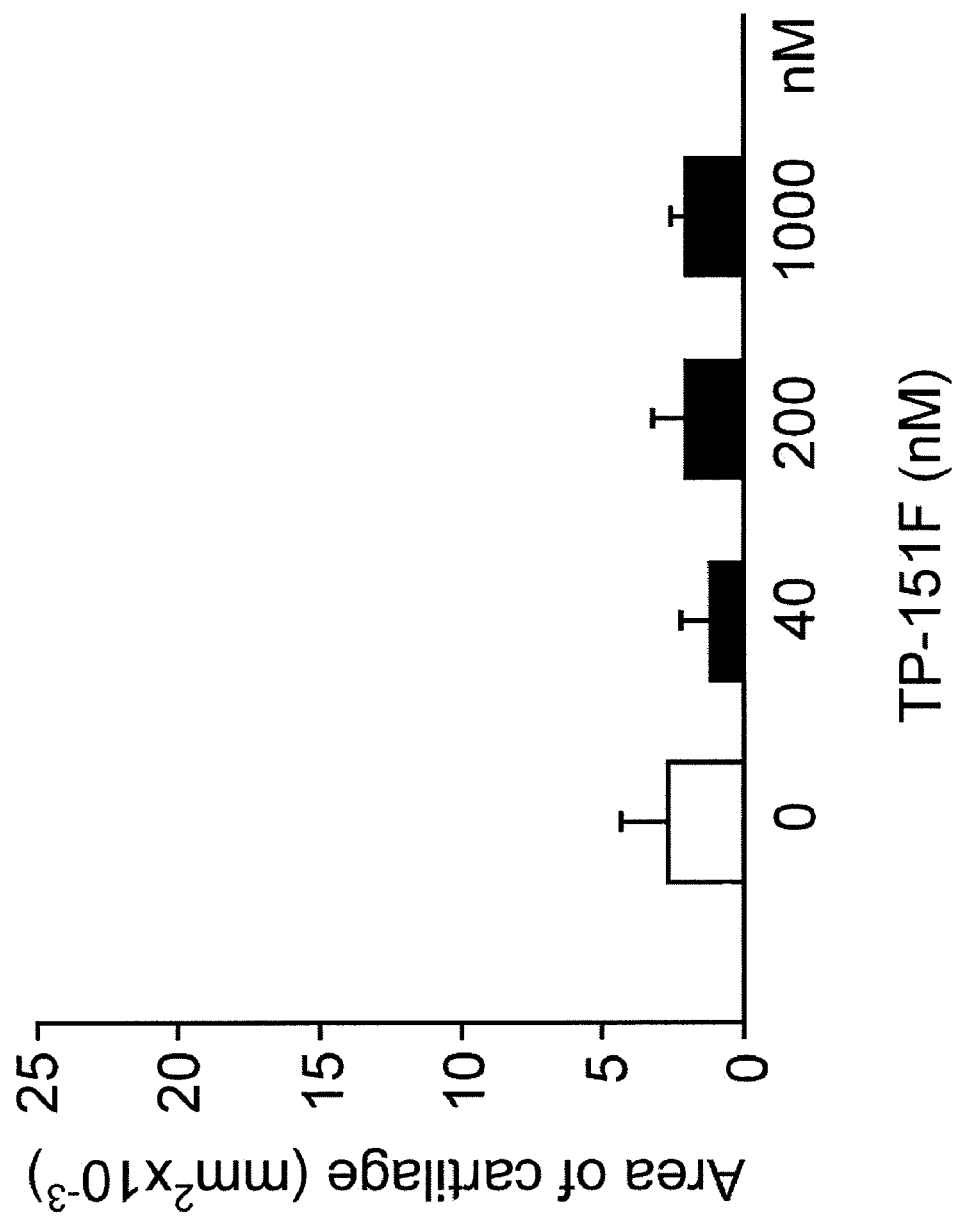
FIGS. 3, 6, 9 and 12—New cartilage growth following treatment with varying concentrations of drug. Cartilage formation was measured in vitro at 7 days at concentrations of 0, 40, 200 and 100 nM for each of TP-151F (FIG. 3), TP-155C (FIG. 6), TP-235H (FIG. 9) and TP-319A (FIG. 12). (The alphabet at the end of each compound number denotes the synthesis batch of each one.)
Figure 4:
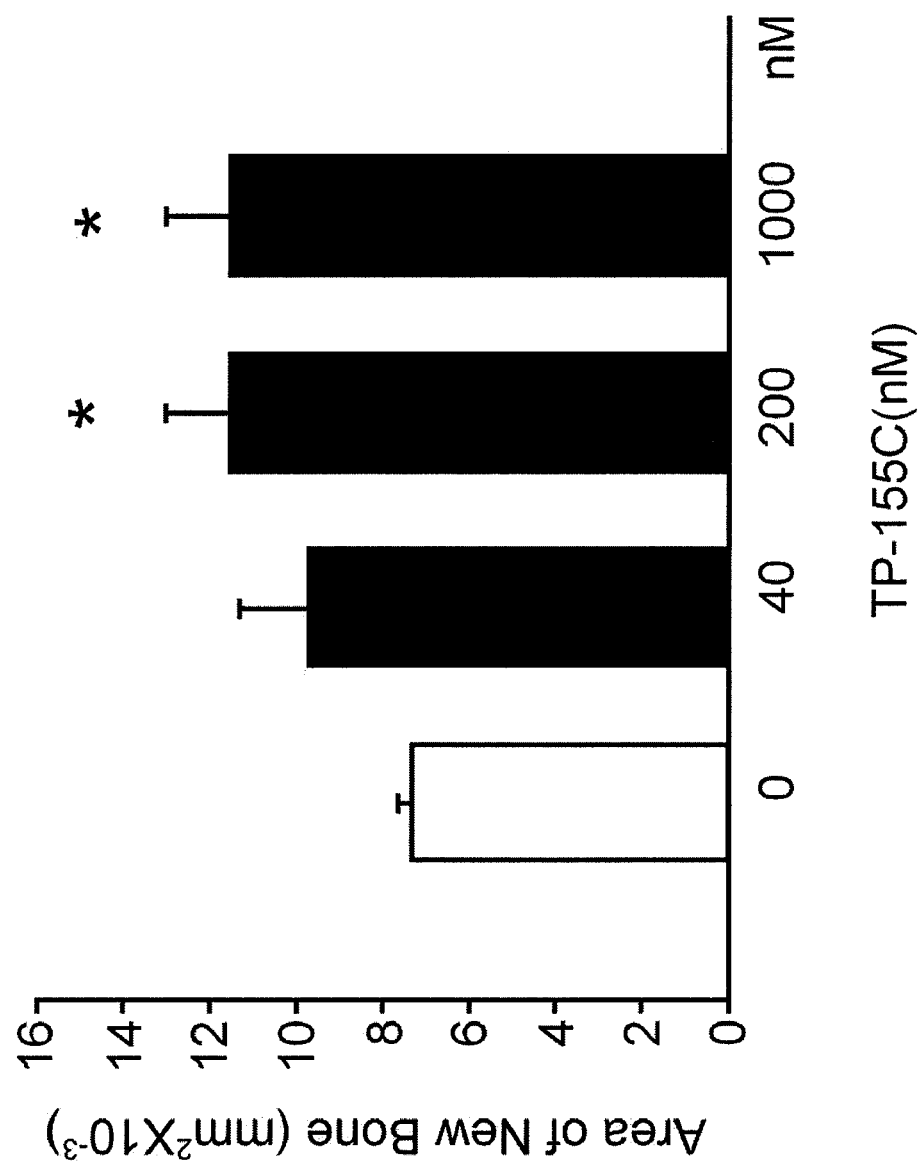

Results were expressed as new bone formation and alkaline phosphatase in the media at 4 and 7 days. Midshaft transverse fractures were induced in all animals. Fractures were tolerated and remained immobilized without surgical complications. Animals were freely mobile after recovery from anesthesia. Callus formation was observed on radiographic examination by 2 weeks in all animals. The animals were euthanized at 3 weeks and callus formation and the biomechanical strength of the bones assessed TP-151. Significant increase in new bone formation (FIG. 1) with increases in alkaline phosphatase in the calvarial culture media (FIG. 2). No evidence of cartilage formation was seen in these cultures (FIG. 3). This indicates this agent is capable of stimulating bone formation, however no cartilage formation was seen.

Figure 5:
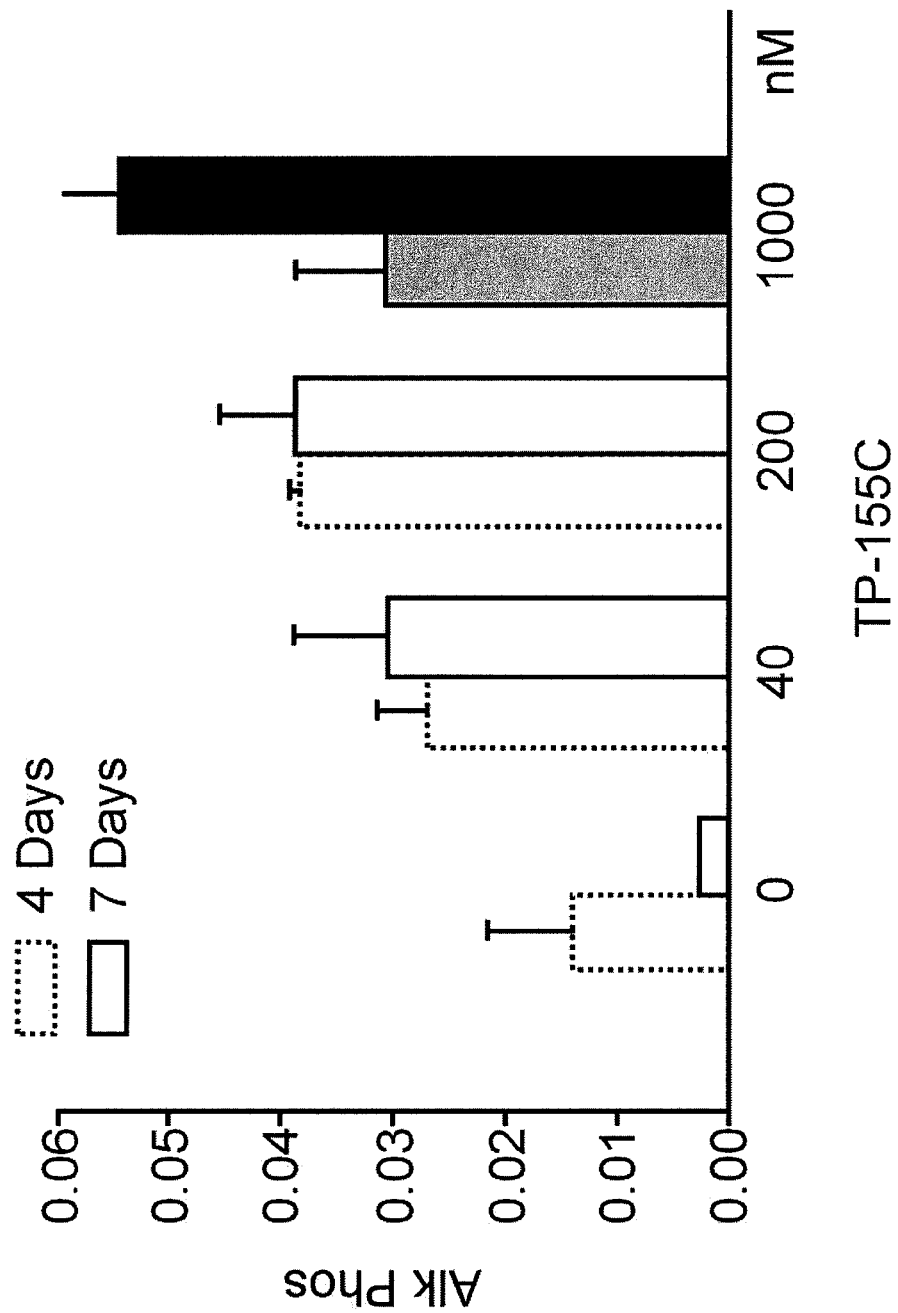
Figure 6:
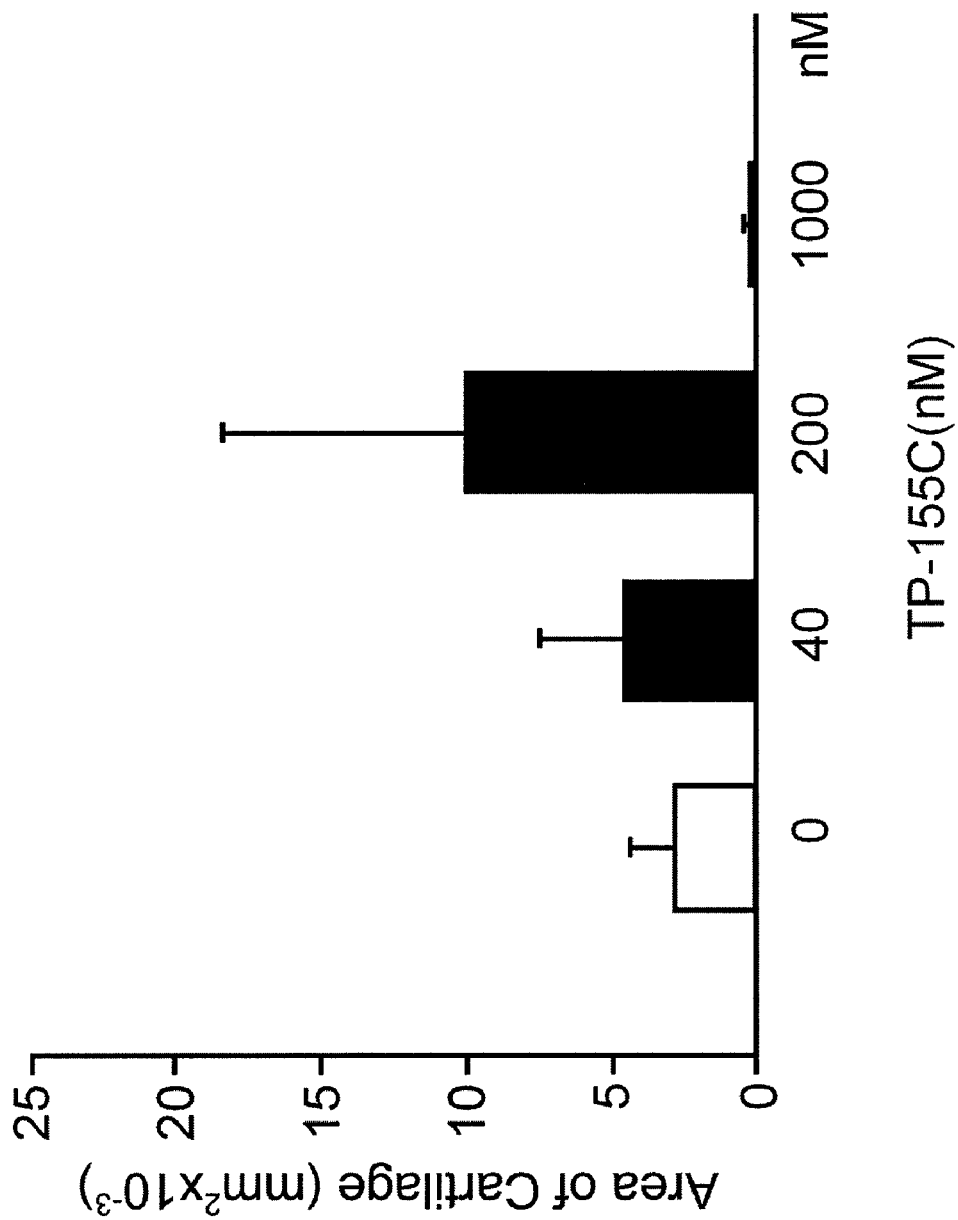
Figure 7:
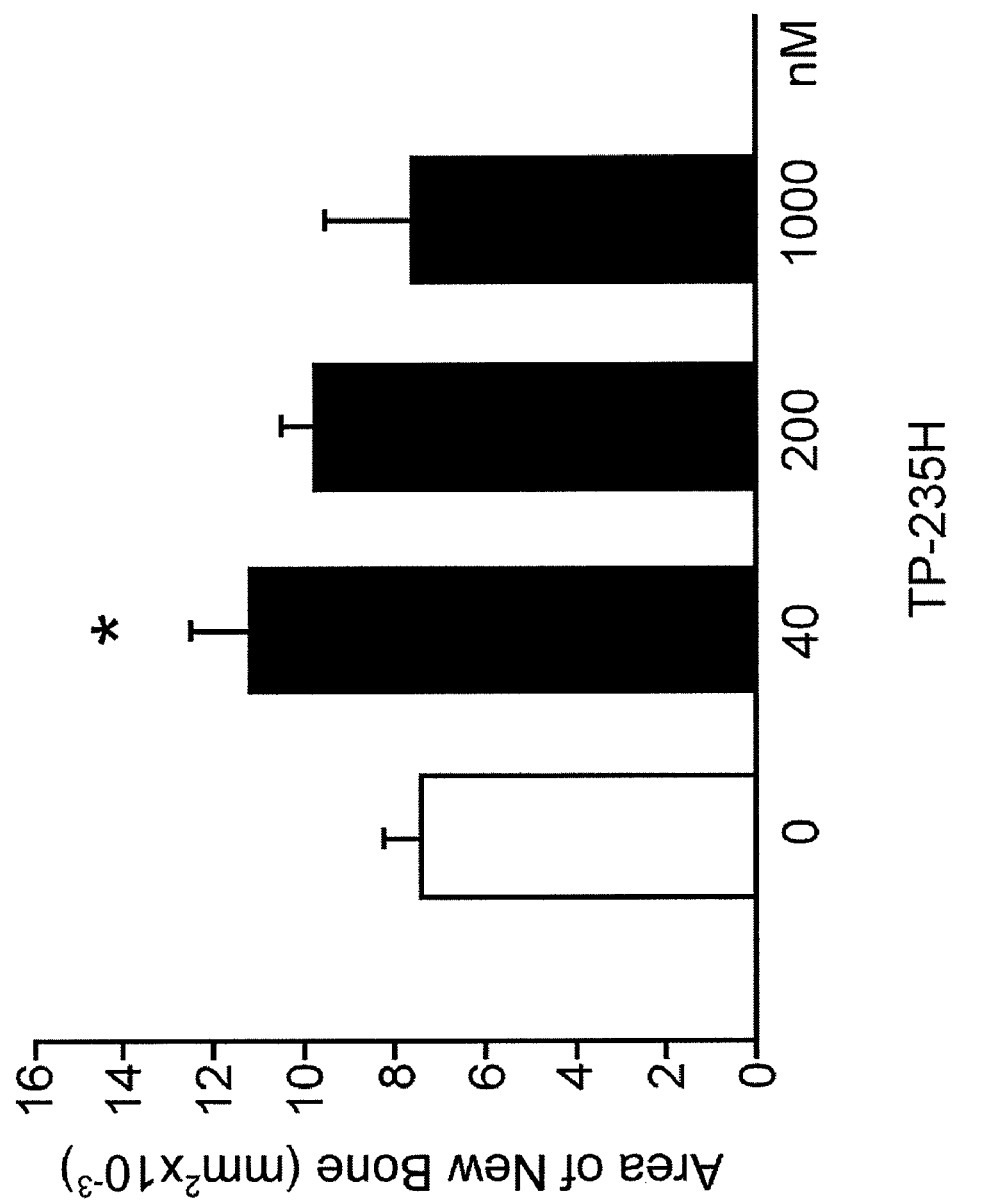

TP-155. Significant increase in new bone formation (FIG. 4) with increases in alkaline phosphatase in the calvarial culture media (FIG. 5). Some evidence of cartilage formation was seen in these cultures (FIG. 3) however this was not significant. This indicates this agent is capable of stimulating bone formation and possibly cartilage formation.

Figure 8:
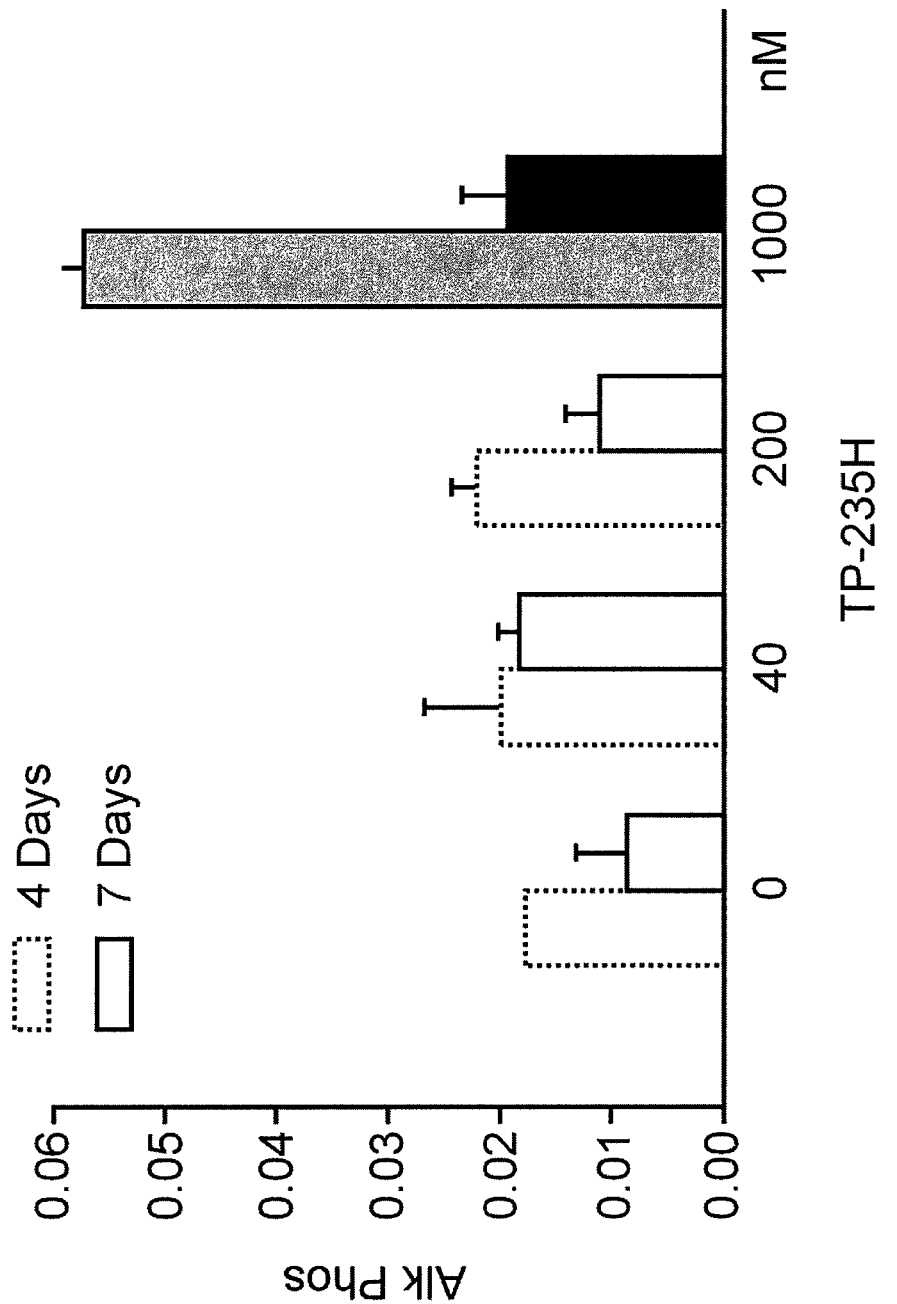
Figure 9:
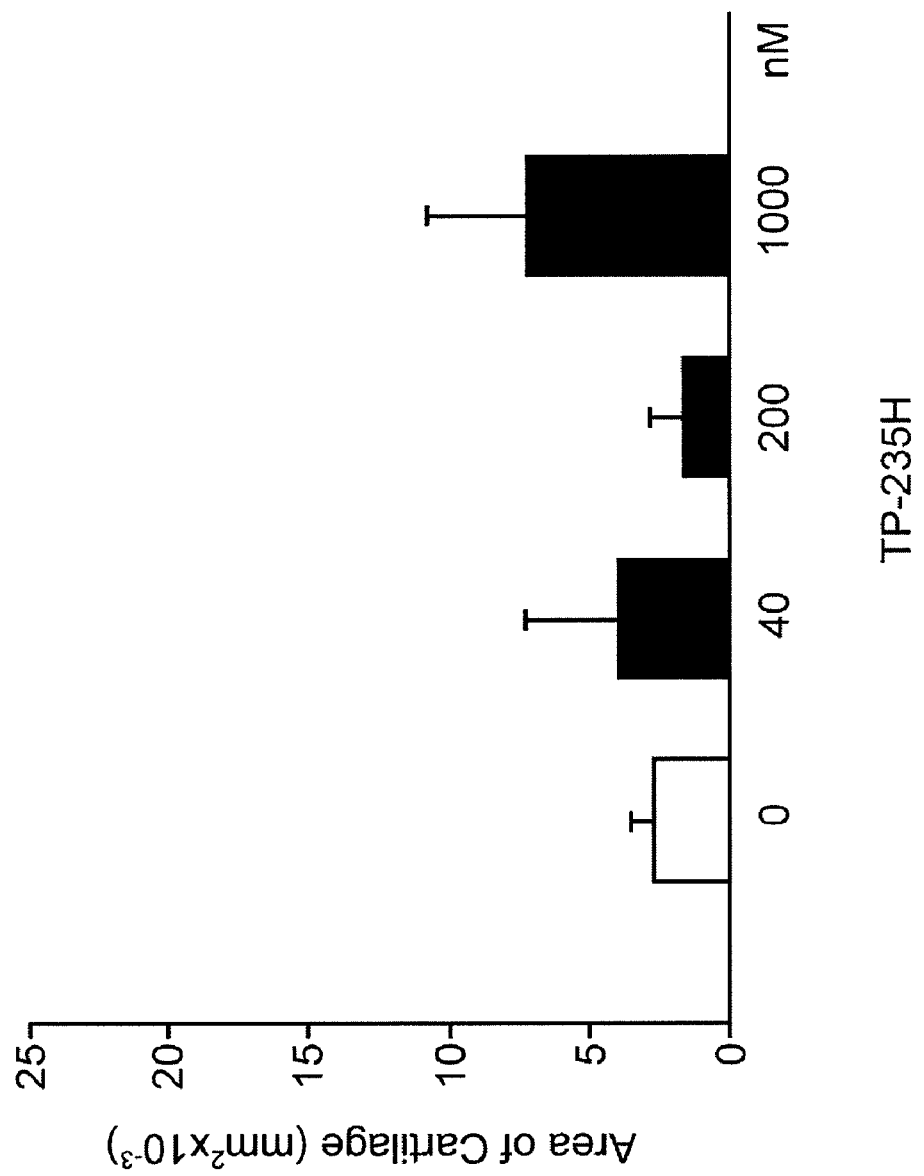
Figure 10:
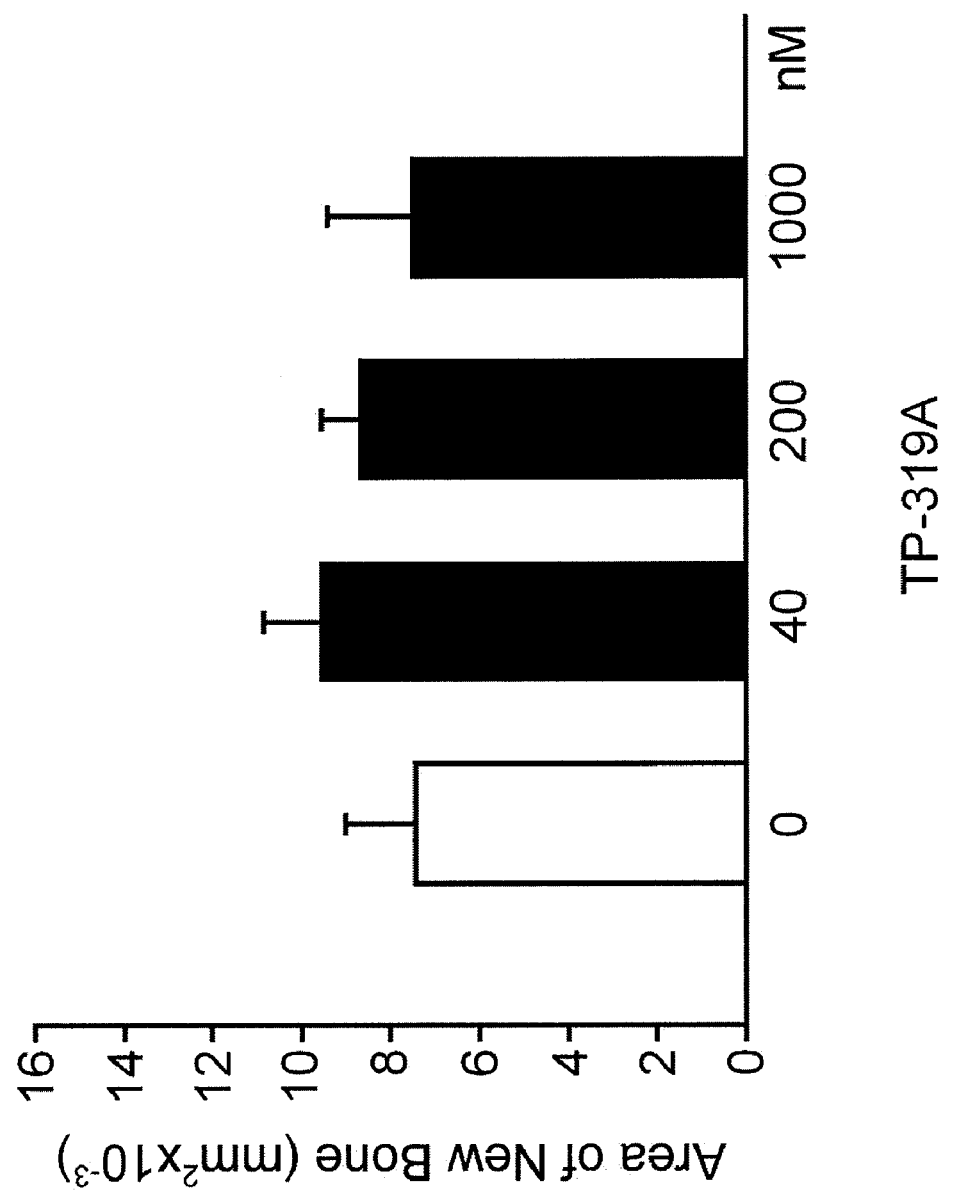

TP-235. Significant increase in new bone formation at 40 nM (FIG. 7) however really no convincing change in alkaline phosphatase in the calvarial culture media (FIG. 8). No evidence of cartilage formation was seen in these cultures (FIG. 9) however this was not significant.

Figure 11:
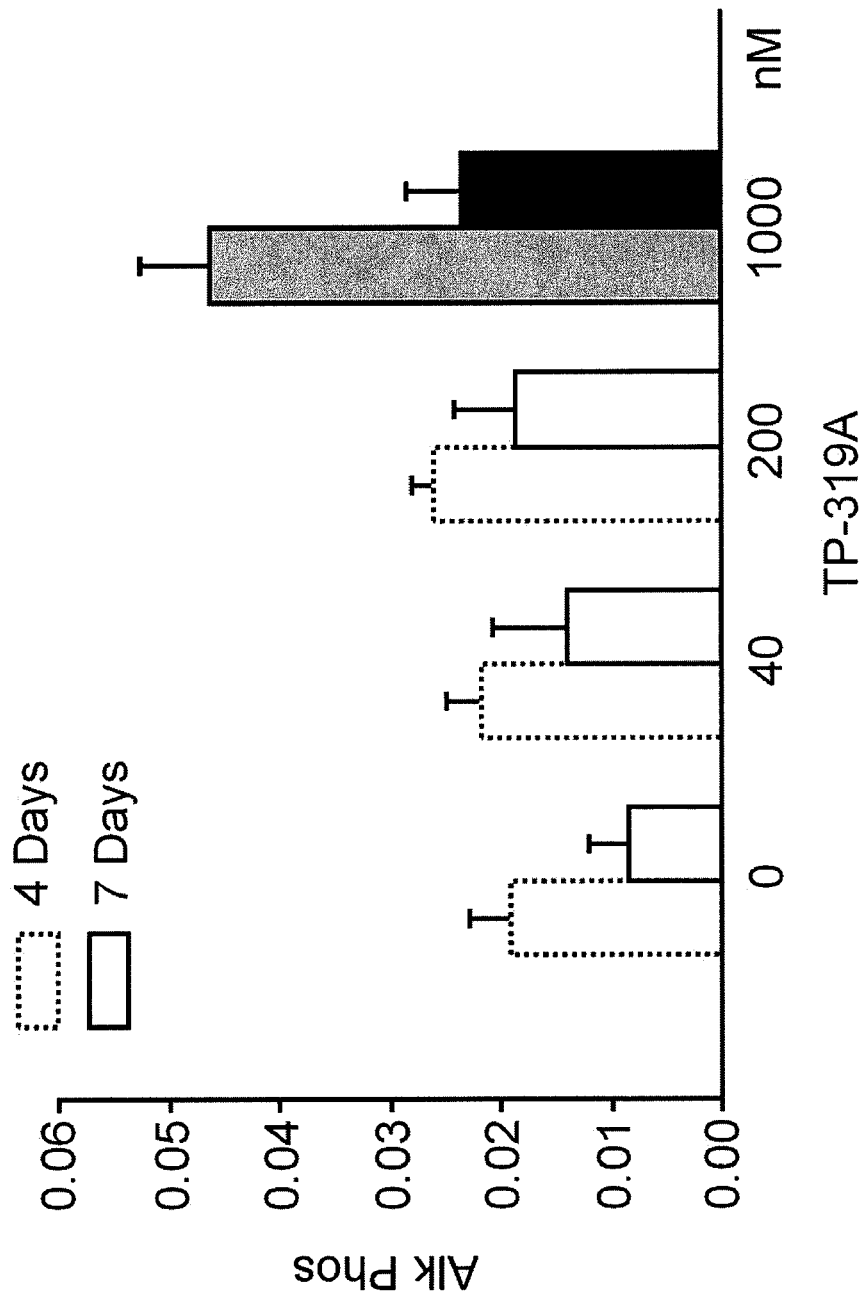
Figure 12:
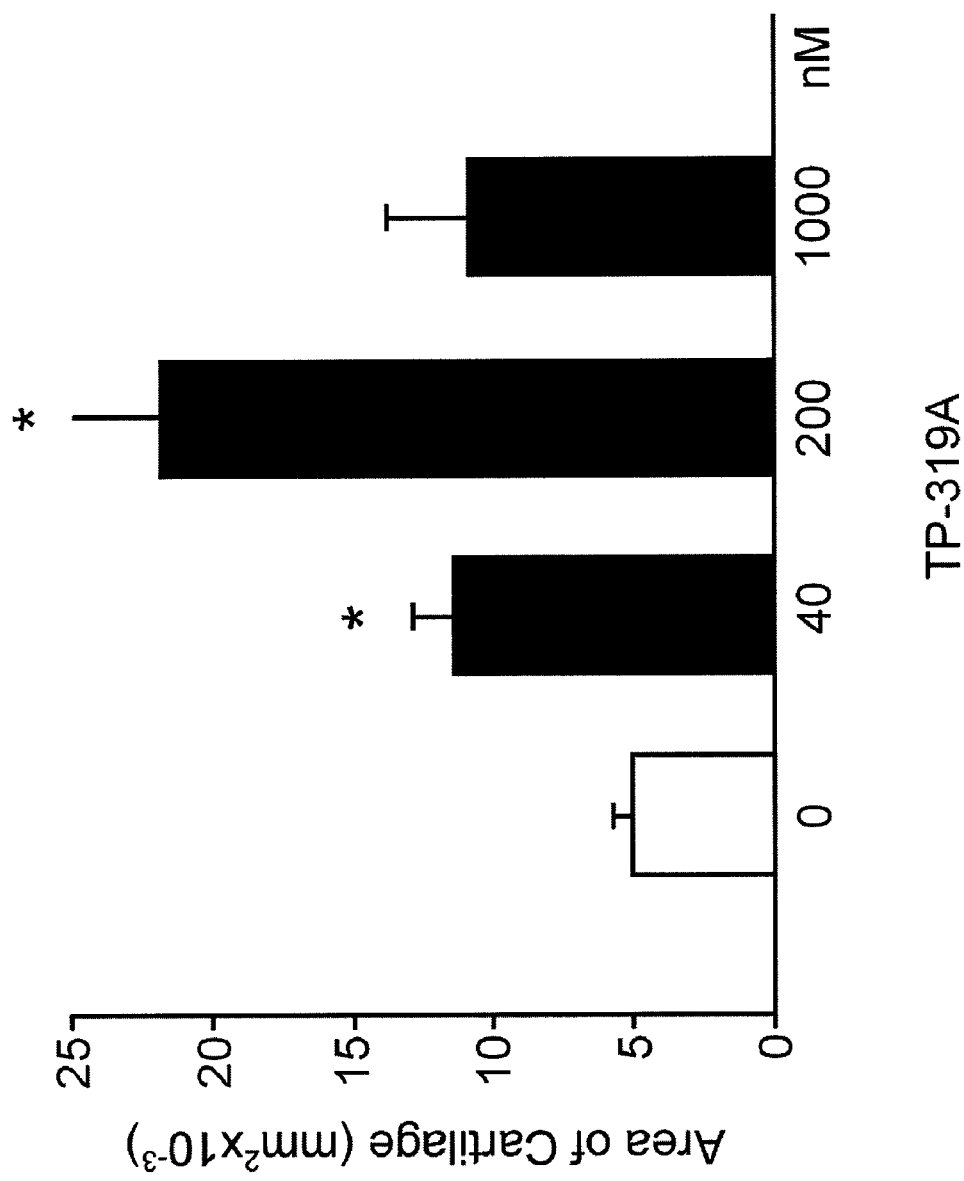

TP-319. Some increases in new bone formation (FIG. 10) and there was also dose responsive increases in alkaline phosphatase in the calvarial culture media (FIG. 11). There was clear evidence increases in cartilage formation was seen in these cultures (FIG. 12).

Example 3

Articular Cartilage Results

TGF-β1. Recombinant human TGF-β1 was found to up-regulate SZP synthesis in a dose-dependent manner (0.4-120 pM).

Triterpenoids at higher concentrations. All four triterpenoids tested, TP-151, TP-155, TP-235, and TP-319, down-regulated SZP synthesis in a dose-dependent manner at high concentrations (100-1000 nM). Concurrent treatment with TGF-β1 (4 pM) also demonstrated the same trend.

Triterpenoids at lower concentrations. TP-151 and TP-155 up-regulated SZP synthesis at lower concentrations, with SZP synthesis increasing as the concentration of these two triterpenoids was increased from 0.01 to 1 nM. TP-235 and TP-319 had no obvious effects in this range.

The results suggest that sub-nanomolar concentrations concentration were optimal for articular cartilage.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 1,995,970
U.S. Pat. No. 2,676,945
U.S. Pat. No. 2,683,136
U.S. Pat. No. 2,703,316
U.S. Pat. No. 2,758,987
U.S. Pat. No. 2,951,828
U.S. Pat. No. 3,531,561
U.S. Pat. No. 4,352,883
U.S. Pat. No. 4,443,546
U.S. Pat. No. 4,533,637
U.S. Pat. No. 5,013,649
U.S. Pat. No. 5,643,736
U.S. Pat. No. 5,972,703
U.S. Patent Publn. US2003/0232786
EP 128 733
EP 273 085
EP 481 791
WO 93/98826
WO 95/06112
Allcock & Fuller, *J. Am. Chem. Soc.*, 103:2250-2256, 1981.
Amstutz et al., *Helv. Chim. Acta.*, 70:2232-2244, 1987.
Aubin et al., *J. of Cell Biol.*, 92:452-461, 1982.
Baichwal and Sugden, In: *Gene Transfer*; Plenum Press, NY, 117-148, 1986.
Barnard et al., *Biochim. Biophys. Acta.*, 1032:79-87, 1990.
Barnes and Sam, *Cell* 22: 649-655, 1980.
Barnes, *Bio Techniques* 5: 534-542, 1987.
Benvenisty and Neshif, *Proc. Nat'l Acad. Sci. USA*, 83:9551-9555, 1986.
Bonadio and Goldstein, In: *Molecular and Cellular Biology of Bone*; Academic Press, San Diego, 169-189, 1993.
Bonewald & Mundy, *Clin. Orthop.*, 250:261-276, 1990.
Bourrin et al., *Endocrin.*, 141:3149-3155, 2000.
Broad, Boraston, and Rhodes, *Cytotechnology* 5:47-55, 1991.
Bruder and Caplan, *Bone*, 10:359-375, 1989.
Bruder and Caplan, *Bone*, 11:189-198, 1990.
Bruder et al., *Trans. Ortho. Res. Soc.*, 16:58, 1991.
Bruland et al., *Cancer Res*, 48:5302-5308, 1988.
Byers and Steiner, *Annu. Rev. Med.* 43:269-289, 1992.
Cai et al., *Helv. Chim. Acta.*, 78:732-757, 1995.
Cassady and Suffness, In: *Anticancer Agents Based on Natural Product Models*; Academic Press, New York, 254-269, 1980

Centrella, *J. Biol. Chem.* 262:2869-2874, 1987.
Charney, E. In: *The Molecular Basis of Optical Activity*; Wiley Interscience, New York, 167-191, 1979.
Chatterjee, et al., *Ann. N.Y. Acad. Sci.,* 770:79-90, 1995.
Chaudhary & Avioli, *Mol Cell Biochem* 178:59-68, 1998.
Cheifetz et al., *Cell* 48, 409-415, 1987.
Chen and Okayama, *Mol. Cell. Biol.,* 7:2745-2752, 1987.
Chen and Weinberg, *Proc. Natl. Acad. Sci. USA,* 92:1565-1569, 1995.
Chen et al., *Exp. Cell Res.,* 195:509, 1991.
Chen et al., *Exp. Cell Res.,* 206:199, 1993.
Cheng et al., *Endocrinology,* 134:277, 1994.
Chung and Wasicak, *Tetrahedron Lett.,* 31:3957-3960, 1990.
Clinton et al., *J. Am. Chem. Soc.,* 83:1478-1491, 1961.
Coffin, In: *Virology,* Raven Press, New York, 1437-1500, 1990.
Conover & Bale, *Exp. Cell Res.,* 238:122-127, 1998.
Conover, In: Principles of Bone Biology, Academic Press, New York, 607-626, 1996.
Corey and Ruden, *Tetrahedron Lett.,* 1495-1499, 1973.
Costantino et al., *Arch. Otolaryngol. Head Neck Surg.* 117(4), 379-384, 1991.
Coupar et al., *Gene,* 68:1-10, 1988.
"Cynamid Research Develops World's First Synthetic Absorbable Suture," *Chemistry and Industry,* 905, 1970.
de Martin et al., *EMBO J.* 6, 3673-3677, 1987.
Denker et al., *Differentiation* 59:25-34, 1995.
Denker, *Differentiation* 59:25-34, 1995.
Derynck et al., *J. Biol. Chem.* 261, 4377-4379, 1986.
Derynck et al., *Nature* 316,701-705, 1985.
Doctor et al., *Dev. Biol.* 151:591-505, 1992.
Dubensky et al., *Proc. Nat'l Acad. Sci. USA,* 81:7529-7533, 1984.
Dunlop and Hall, *Int. J. Dev. Biol.,* 39:357-371, 1995.
Elgendy et al., *Biomaterials,* 14, 263-269, 1993.
Elias, In: *Principles and Techniques in Diagnostic Histopathology*, Noyes Publication, Park Ridge, 248-250, 1982.
Embleton et al., *Br J Cancer,* 43:582-587, 1981.
Farley et al., *Calc. Tiss. Res.,* 67:247-254, 2000.
Favaloro et al., *J. Med. Chem.,* 45:4801-4805, 2002.
Fawthrop et al., *J. Bone Miner. Res.* 7:1363-1371, 1992.
Fechheimer et al., *Proc. Nat'l Acad. Sci. USA,* 84:8463-8467, 1987.
Ferkol et al., *FASEB J.,* 7:1081-1091, 1993.
Ferrari et al., *J. Virol.,* 70:3227-3234, 1996.
Feyen et al., *J. Biol. Chem.,* 266:19469-19474, 1991.
Finkbeiner and Stiles, *J. Am. Chem. Soc.,* 85:616-622, 1963.
Fisher et al., *J. Virol.,* 70:520-532, 1996.
Flotte et al., *Proc. Nat'l Acad. Sci. USA,* 90:10613-10617, 1993.
Fraley et al., *Proc. Nat'l Acad. Sci. USA,* 76:3348-3352, 1979.
Frame, *Int J Oral Maxillofac Surg.* 16(6):642-55, 1987.
Franceschi, *J. Biol. Chem.* 263:18938-18945, 1988.
Franceschi, *J. Cell Physiol.,* 123:401-409, 1985.
Friedman et al., *Arch. Otolaryngol. Head Neck Surg.* 117(4), 386-389, 1991.
Gasmi et al., *J. Virol.,* 73(3):1828-34, 1999.
Gerhart et al., *Trans. Orthop. Res. Soc.,* 16:172, 1991.
Ghosh and Bachhawat, In: *Liver diseases, targeted diagnosis and therapy using specific receptors and ligands*, Marcel Dekker, New York, 87-104, 1991.
Glowacki et al., *Clin. Plast. Surg.* 12(2), 233-241, 1985.
Gomori, *Am. J. Clin. Pathol.,* 20:661, 1950.
Goodman et al., *Blood,* 84:1492-1500, 1994.
Gopal, *Mol. Cell. Biol.,* 5:1188-1190, 1985.
Graham and Van Der Eb, *Virology,* 52:456-467, 1973.
Grieco and Speake, *J. Org. Chem.,* 63:5929-5936, 1998.
Hall and Miyake, *Anat. Embryol.,* 186:107-124, 1992.
Hall and Miyake, *Int. J. Dev. Biol.,* 39:881-893, 1995.
Harada, *Shikwa-Gakuho* 89(2), 263-297, 1989.
Harlow & Lane, In: *Using Antibodies: A Laboratory Manual*, Cold Spring Harbor Laboratory, 1988.
Hay et al., *J. Mol. Biol.,* 175:493-510, 1984.
Hayat, In: *Principles and Techniques of Electron Microscopy: Biological Applications*, CRC Press, Boca Raton, 1989.
Hearing and Shenk, *J. Mol. Biol.* 167:809-822, 1983.
Hearing et al., *J. Virol.,* 67:2555-2558, 1987.
Heiner et al., *Cancer Res,* 47:5377-5384, 1987.
Hidvegi et al., *Osteoarthr. Cartil.,* 14(1):89-93, 2006.
Hollinger and Battistone, *Clin. Orthopedics and Related Res.,* 207:290-305, 1986.
Honda et al., *Bioorg. Med. Chem. Lett.,* 12:1027-1030, 2002.
Honda et al., *Bioorg. Med. Chem. Lett.,* 19:2711-2714, 1998.
Honda et al., *Bioorg. Med. Chem. Lett.,* 7:1623-1628, 1997.
Honda et al., *Bioorg. Med. Chem. Lett.,* 9:3429-3434, 1999.
Honda et al., *J. Med. Chem.,* 43:1866-1877, 2000a.
Honda et al., *J. Med. Chem.,* 43:4233-4246, 2000b.
Honda et al., *Org. Biomol. Chem.,* 1:4384-4391, 2003.
Honda et al., *Org. Prep. Proced. Int.,* 37:546-550, 2005.
Hosoi et al., *Cancer Res,* 42:654-661, 1982.
Huang et al., *Cancer Res.,* 54:5841-5847, 1994.
Huang et al., *Cancer Res.,* 54:701-708, 1994.
Ignotz & Massague, *J. Biol. Chem.* 261:4337-4345, 1986.
Iguchi et al, *J. Appl. Toxicol.,* 13(4):269-275, 1993.
Jayme, *Cytotechnology* 5(1):15-30, 1991.
Johnson et al. *J. Am. Chem. Soc.,* 67:1745-1754, 1945.
Kahne, *Tetrahedron Lett.,* 22:5011-5014, 1981.
Kaneda et al., *Science,* 243:375-378, 1989.
Kaplitt et al., *Nat. Genet.,* 8:148-153, 1994.
Kato et al, *J. Biol. Chem.,* 266:3361-3364, 1991.
Kerwin et al., *J. Org. Chem.,* 52:1686-1695, 1987.
Kessler et al., *Proc. Nat'l Acad. Sci. USA,* 93:14082-14087, 1996.
Kim et al., *Calcif Tissue Int.,* 59:58-63, 1996.
Kim et al., *Nature,* 362:841-844, 1993.
Kimura et al., *Biomed. Res.,* 5:465, 1984.
Klein et al., *Nature,* 327:70-73, 1987.
Koeberl et al., *Proc. Nat'l Acad. Sci. USA,* 94:1426-1431, 1997.
Kojima et al., *J. Cell Biol.,* 113(6):1439-1445, 1991.
Komori et al., *Cell* 89:755-764, 1997.
Kowalski et al., *J. Org. Chem.,* 57:7194-7208, 1992.
Kulkarni et al., *J. Biomedical Materials Research,* 5, 169-81, 1971.
Langille et al., *Differentiation,* 40:84, 1989.
Laurencin et al., *J. Biom. Mater. Res.,* 27, 1993.
Lawson et al., *Clin Chem,* 31:381-385, 1985.
Levrero et al., *Gene,* 101: 195-202, 1991.
Liby et al., *Cancer Res.,* 65(11):4789-4798, 2005.
Lillie, *Stain Technol.,* 15:17, 1940.
Liotta et al., *J. Org. Chem.,* 46:2920-2923, 1981.
Long, *J. Clin. Invest.,* 86:1387-1395, 1990.
Long, *J. Clin. Invest.,* 95:881-887, 1995.
Malpe et al., *J. Bone Min. Res.,* 12:423-430, 1997.
Mann et al., *Cell,* 33:153-159, 1983.
Marden et al., *J. Craniofac. Surg.,* 1(3):154-160, 1990.
Marquardt et al., *J. Biol. Chem.,* 262:12127-12131, 1987.
Massague et al., *Trends Cell Biol.,* 4:172-178, 1994.
McCown et al., *Brain Res.,* 713:99-107, 1996. McGee-Russell, *J. Histochem.,* 6:22-42, 1958.
Mella et al., *Tetrahedron,* 44:1673-1678, 1988.
Mendelsohn, *Calcif Tissue Int* 44:20-24, 1989.
Minns et al., *Gastroenterology* 127:119-26, 2004.

Mix et al., *Mol Pharmacol* 65:309-318, 2004.
Miyake et al., *J. Craniofacial Gen. Dev. Biol.*, 16:32-47, 1996.
Miyazono et al., *Adv. Immunol.* 55:181-220, 1994.
Mizukami et al., *Virology*, 217:124-130, 1996.
Mohan, *Growth Regulation* 3:67-70, 1993.
Murray and Zweifel, *Synthesis*, 150-151, 1980.
Muzart, *Tetrahedron Lett.*, 28:4665-4668, 1987.
Nicolas and Rubenstein, In: *Vectors: A Survey of Molecular Cloning Vectors and Their Uses*, Butterworth, Stoneham, 493-513, 1988.
Nicolau and Sene, *Biochim. Biophys. Acta*, 721:185-190, 1982.
Nicolau et al., *Methods Enzymol.*, 149:157-176, 1987.
Nikol et al., *J. Clin. Invest.* 90:1582-1592, 1992.
Nishino et al., *Cancer Res.*, 48:5210-5215, 1988.
Oberlender and Tuan, *Cell Adhesion & Communication*, 2:521-537, 1994.
Ohgushi et al., *Acta Orthop. Scand.* 60(3), 334-339, 1989.
Omura and Swem, *Tetrahedron* 1978, 34, 1651-1660.
Ono et al., *Biomaterials* 11(4), 265-271, 1990.
Padgett et al., *Nature* (London), 325:81-84, 1987.
Palcy et al., *Biochem. J.*, 343:21-27, 1999.
Parsons et al., *Ann NY Acad. Sci.* 523:190-207, 1988.
Paschalis et al., *Bone* 19:151-156, 1996. Paskind et al., *Virology*, 67:242-248, 1975.
Passuti et al., *Clin. Orthop.* 248, 169-176, 1989.
Paul et al., *Nature Biotechnol.*, 20:505-508, 2002.
Perales et al., *Proc. Nat'l Acad. Sci. USA* 91:4086-4090, 1994.
Ping et al., *Microcirculation*, 3:225-228, 1996.
Pinholt et al., *J. Oral Maxillofac. Surg.* 50(8), 859-867, 1992.
Pinholt et al., *Scand. J. Dent. Res.* 99(2), 154-161, 1991.
Place et al., *Clin. Cancer Res.*, 9(7):2798-2806, 2003.
Plate et al., *Nature* 359:845-848, 1992.
Pochon et al., *Z-Kinderchir.* 41(3), 171-173, 1986.
Potter et al., *Proc. Nat'l Acad. Sci. USA*, 81:7161-7165, 1984.
Prockop, *J. Biol. Chem.* 265:15349-15352, 1990.
Radler et al., *Science*, 275:810-814, 1997.
Renan, *Radiother. Oncol.*, 19:197-218, 1990.
Rey, *Connective Tiss Res* 35:397-403, 1996.
Rey, *J Bone Miner Res* 10: 1577-1588, 1995.
Richman et al., *Endocrin* 140:4699-4705, 1999.
Ridgeway, In: *Vectors: A survey of molecular cloning vectors and their uses*, Butterworth, Stoneham, 467-492, 1988.
Rinderknecht, *FEBS Lett.*, 89:283, 1978b.
Rinderknecht, *J. Biol. Chem.*, 253:2769, 1978a.
Rippe et al., *Mol. Cell. Biol.*, 10:689-695, 1990.
Roberts and Sporn, eds., *The Transforming Growth Factor-βs in Peptide Growth Factors and Their Receptors. L Handbook of Experimental Pharmacology*, vol. 95/I, Springer-Verlag, Berlin, 419-472, 1990.
Robey and Termine, *Calcif. Tissue Int.*, 37:453-460, 1985.
Roesgen, *Unfallchirurgle*, 16(5):258-265, 1990.
Roux et al., *Proc. Nat'l Acad. Sci. USA*, 86:9079-9083, 1989.
Ruest et al., *Syn. Comm.*, 6:169-174, 1976.
Sambrook et al., In: *Molecular Cloning: A Laboratory Manual*, 2d Ed., Cold Spring Harbor Laboratory Press, Cold Spring Harbor, N.Y., 1989.
Samulski et al., *J. Virol.*, 61(10):3096-3101, 1987.
Sanger et al., *Cancer* 46:5629-5632, 1986.
Schweiki et al., *Nature* 359:843-845, 1992.
Sharples et al., *DNA* 6, 239-244, 1987.
Shull et al. *Am. J. Pathol.*, 114(3):487-495, 1984.
Shull et al., *Proc. Nat'l Acad. Sci. USA*, 86:5405-5410, 1989.
Sive et al., *Mol. Pathol.*, 55(2):91-97, 2002.
Smith, *Anal. Biochem.*, 150:76-85, 1985.

Sonogashira et al., *Tetrahedron Lett.*, 4467-4470, 1975.
Sporn et al., *Science*, 233:532-534, 1986.
Sterzycki, R *Synthesis*, 724-725, 1979.
String a et al., *Exp. Cell Res.*, 232:287-294, 1997.
Suh et al., *Cancer Res* 63:1371-1376, 2003.
Suh et al., *Cancer Res.*, 58:717-723, 1998.
Suh et al., *Cancer Res.*, 59(2):336-341, 1999.
Syftestad et al., *Differentiation*, 29:230, 1985.
Sykes, *Biochem. Biophys. Res. Commun.*, 72:1472-1480, 1976.
Temin, In: *Gene Transfer*, Plenum Press, New York, 149-188, 1986.
Ten Dijke et al., *Proc. Nat'l Acad. Sci. USA*, 85:4715-4719, 1988.
Tenenbaum et al., *Calcif. Tissue Int.*, 34:76, 1982.
Thomas et al., *Endocrinology* 140:5036-5044, 1999.
Tibbetts *Cell*, 12:243-249, 1977.
Toriumi et al., *Arch. Otolaryngol Head Neck Surg.*, 117:1101-1112, 1991.
Towbin, *Proc. Nat'l Acad. Sci. USA*, 76:4350-4354, 1979.
Tsai et al., *Cancer Res.*, 50:152-161, 1990.
Tur-Kaspa et al., *Mol. Cell. Biol.*, 6:716-718, 1986.
Turksen et al., *J Histochem Cytochem*, 40:1339-1352, 1992.
Vukicevic et al., *Proc. Nat'l Acad. Sci. USA*, 86:8793, 1989.
Wade et al., In: *Organometallic Polymers*, Academic Press, New York, 283-288, 1978.
Wagner et al., *Proc. Nat'l Acad. Sci. USA* 87(9):3410-3414, 1990.
Walsh et al., *J. Bone Miner Res.*, 9:1687-1696, 1994.
Watt et al., *Proc. Nat'l Acad. Sci. USA*, 83(2): 3166-3170, 1986.
Weeks and Melton, *Cell*, 51:861-867, 1987.
White et al., *J. Virol.*, 73(4):2832-40, 1999.
Wong and Tuan, *Dev. Biol.*, 167:130-147, 1995.
Wong et al., *Gene*, 10:87-94, 1980.
Woodward and Tuan, *Dev. Gen.*, 24:178-187, 1999.
Wozney, In: *Cellular and Molecular Biology of Bone*, Academic Press, 131-167, 1993.
Wrana et al., *Nature*, 370:341-347, 1994.
Wu and Wu, *Adv. Drug Delivery Rev.*, 12:159-167, 1993.
Wu and Wu, *Biochem.*, 27:887-892, 1988.
Wu and Wu, *J. Biol. Chem.*, 262:4429-4432, 1987.
Xiao et al., *J. Virol.*, 70:8098-8108, 1996.
Yang et al., *Proc. Nat'l Acad. Sci. USA*, 87:9568-9572, 1990.
Zambonin et al., *Acta Orthop. Scand.*, 70:217-220, 1999.

What is claimed is:

1. A method for stimulating a bone-forming or osteochondrogenic cell comprising:
   a) providing a bone-producing or osteochondrogenic cell;
   b) contacting said cell with an effective amount of a compound having the structure:

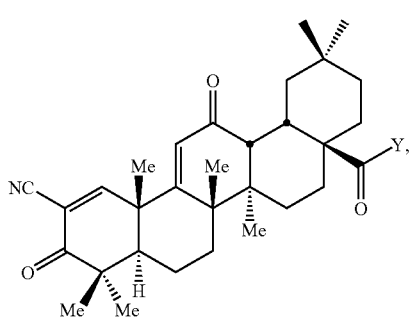

wherein Y is hydroxy, methoxy, ethyl-amino, or

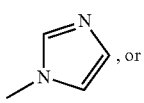, or a pharmaceutically acceptable salt or tautomer thereof; and
c) culturing the cell.

2. The method of claim 1, wherein the cell is of human origin.

3. The method of claim 1, wherein the cell is of bovine, equine, canine, feline, murine, rat or chick origin.

4. The method of claim 1, further comprising incubating said cell with a growth factor.

5. The method of claim 4, wherein the growth factor is TGF-β1, TGF-β2, TGF-β1.2, VEGF, insulin-like growth factor I or II, BMP2, BMP4, or BMP7.

6. The method of claim 4, wherein the growth factor is parathyroid hormone, calcitonin, interleukin-6, or interleukin-11.

7. The method of claim 1, further comprising purifying said cell after step (b).

8. The method of claim 1, further comprising implanting said cell in vivo after step (b) and/or step (c).

9. The method of claim 1, wherein bone is formed by said cell.

10. The method of claim 1, wherein the cell is an osteoblast.

11. A method of providing bone tissue to a mammal comprising:
 a) providing a bone-producing cell;
 b) contacting said cell with an effective amount of a compound having the structure:

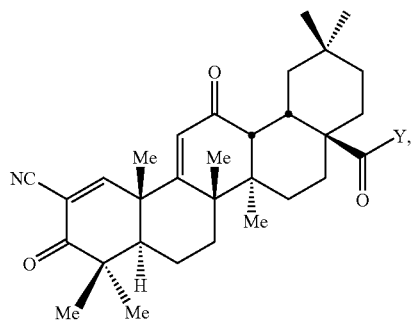

wherein Y is hydroxy, methoxy, ethyl-amino, or

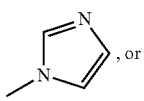, or a pharmaceutically acceptable salt or tautomer thereof;
c) culturing the cell to form bone; and
d) implanting said bone to said subject.

12. The method of claim 11, wherein the bone formed in step (c) is part of a three-dimensional matrix.

13. The method of claim 12, wherein the three-dimensional matrix is one or more of alginate gels, collagen gels, or fibrin gels.

14. The method of claim 12, wherein the three-dimensional matrix comprises one or more of polylactic acid, polyglycolic acid or PGLA.

15. The method of claim 12, wherein the three-dimensional matrix comprises one or more of hydroxyapatite or other apatitic compounds, devitalized animal bone, devitalized human bone, or porous ceramic structures.

16. The method of claim 11, wherein the mammal has cancer bone disease, localized osteolysis due to cancer and to myeloma, degenerative cartilage conditions, osteoarthritis, osteoporosis, Vitamin D deficiency, Osteotitis deformans, or Von Recklinghausen's Disease.

17. The method of claim 11, wherein the cell is of human origin.

18. The method of claim 11, wherein the cell is of bovine, equine, canine, feline, murine, rat or chick origin.

19. A method for producing bone ex vivo comprising:
 a) providing a bone-producing cell;
 b) contacting said cell with an effective amount of a compound having the structure:

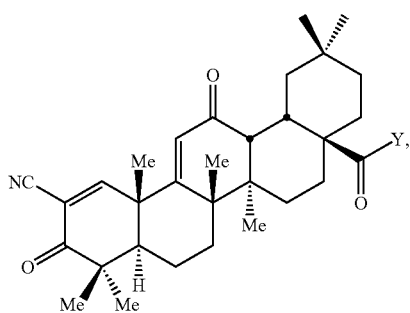

wherein Y is hydroxy, methoxy, ethyl-amino, or

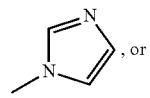, or a pharmaceutically acceptable salt or tautomer thereof; and
c) culturing the cell to form bone.

20. A method of repairing bone damage in a patient having a bone defect, bone trauma, osteoarthritis, osteoporosis, or Vitamin D deficiency, comprising administering to said patient an amount of a compound effective to repair bone damage, said compound having the structure:

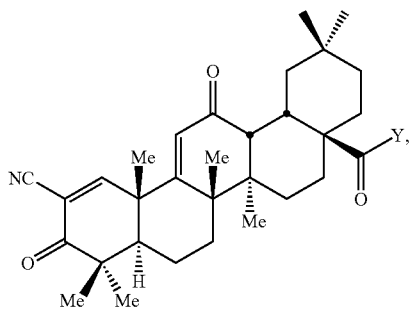

wherein Y is hydroxy, methoxy, ethyl-amino, or

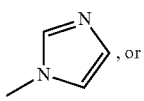, or a pharmaceutically acceptable salt or tautomer thereof.

21. A method for stimulating a cartilage-forming cell comprising:
 a) providing a cartilage-producing or osteochondrogenic cell;
 b) contacting said cell with an effective amount of a compound having the structure:

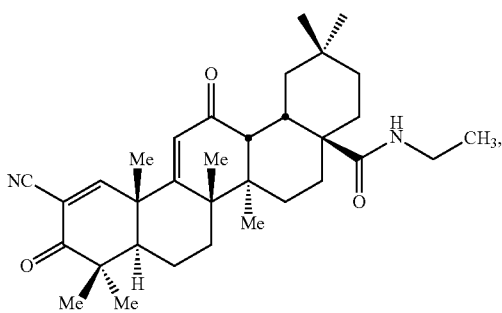

or a pharmaceutically acceptable salt or tautomer thereof; and
 c) culturing the cell.

22. A method of repairing cartilage damage in a patient having cartilage disease or cartilage trauma comprising administering to said patient an amount of a compound effective to repair cartilage damage, said compound having the structure:

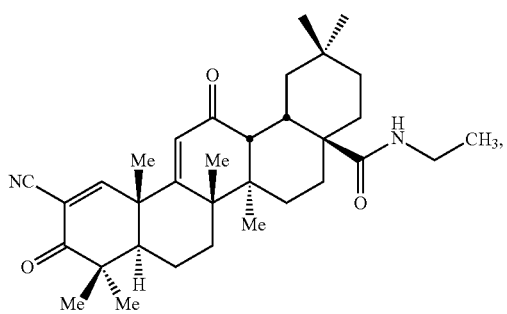

or a pharmaceutically acceptable salt or tautomer thereof.

23. The method of claim 22, wherein the patient is human.
24. The method of claim 22, wherein cartilage is formed.
25. The method of claim 20, wherein the compound is administered to a wound.
26. The method of claim 20, wherein the compound is administered to a bone disease site.
27. The method of claim 20, wherein the patient has bone trauma.
28. The method of claim 20, wherein the patient has a bone defect.
29. The method of claim 28, wherein the bone defect is the result of a birth defect.
30. The method of claim 20, wherein the patient is human.
31. The method of claim 20, wherein bone is formed.
32. The method of claim 27, wherein the bone trauma is a fracture.
33. The method of claim 28, wherein the bone defect is the result of cancer surgery.
34. The method of claim 20, wherein the patient has osteoarthritis.
35. The method of claim 20, wherein the patient has osteoporosis.
36. The method of claim 20, wherein the patient has Vitamin D deficiency.

* * * * *